(12) United States Patent
Newman et al.

(10) Patent No.: US 10,722,482 B2
(45) Date of Patent: Jul. 28, 2020

(54) METHOD OF AND IMPROVED COMPOSITION FOR TREATING TRITERPENE-RESPONSIVE CONDITIONS, DISEASES OR DISORDERS

(71) Applicant: PHOENIX BIOTECHNOLOGY, INC., San Antonio, TX (US)

(72) Inventors: Robert A. Newman, Surry, ME (US); Otis C. Addington, San Antonio, TX (US); Donald C. Lo, Chapel Hill, NC (US); Linda S. Kaltenbach, Hillsborough, NC (US)

(73) Assignee: PHOENIX BIOTECHNOLOGY, INC., San Antonio, TX (US)

( * ) Notice: Subject to any disclaimer, the term of this patent is extended or adjusted under 35 U.S.C. 154(b) by 0 days.

(21) Appl. No.: 16/184,628

(22) Filed: Nov. 8, 2018

(65) Prior Publication Data

US 2019/0076381 A1   Mar. 14, 2019

Related U.S. Application Data

(63) Continuation of application No. PCT/US2018/059818, filed on Nov. 8, 2018, which is a continuation-in-part of application No. PCT/US2018/049358, filed on Sep. 4, 2018, said application No. 16/184,628 is a continuation-in-part of application No. PCT/US2018/049358, filed on Sep. 4, 2018.

(60) Provisional application No. 62/558,631, filed on Sep. 14, 2017.

(51) Int. Cl.
| | |
|---|---|
| A61K 31/19 | (2006.01) |
| A61P 11/00 | (2006.01) |
| A61K 45/06 | (2006.01) |
| A61P 25/28 | (2006.01) |
| A61P 25/16 | (2006.01) |
| A61P 31/14 | (2006.01) |
| A61P 33/02 | (2006.01) |
| A61P 1/00 | (2006.01) |
| A61P 9/00 | (2006.01) |
| A61P 1/16 | (2006.01) |
| A61P 19/00 | (2006.01) |
| A61P 17/02 | (2006.01) |
| A61P 13/12 | (2006.01) |
| A61P 3/00 | (2006.01) |
| A61K 31/57 | (2006.01) |
| A61K 31/56 | (2006.01) |

(52) U.S. Cl.
CPC ............. *A61K 31/19* (2013.01); *A61K 31/56* (2013.01); *A61K 31/57* (2013.01); *A61K 45/06* (2013.01); *A61P 1/00* (2018.01); *A61P 1/16* (2018.01); *A61P 3/00* (2018.01); *A61P 9/00* (2018.01); *A61P 11/00* (2018.01); *A61P 13/12* (2018.01); *A61P 17/02* (2018.01); *A61P 19/00* (2018.01); *A61P 25/16* (2018.01); *A61P 25/28* (2018.01); *A61P 31/14* (2018.01); *A61P 33/02* (2018.01)

(58) Field of Classification Search
CPC ..................................................... A61K 31/19
See application file for complete search history.

(56) References Cited

U.S. PATENT DOCUMENTS

| | | | |
|---|---|---|---|
| 5,977,174 A | 11/1999 | Bradley | |
| 6,217,874 B1 | 4/2001 | Johannsen | |
| 7,402,325 B2 | 7/2008 | Addington | |
| 8,187,644 B2 | 5/2012 | Addington | |
| 8,394,434 B2 | 3/2013 | Addington | |
| 8,481,086 B2 * | 7/2013 | Addington | ......... A61K 31/7048 424/725 |
| 9,011,937 B2 * | 4/2015 | Addington | ............... A61P 25/00 424/725 |
| 9,220,778 B2 * | 12/2015 | Addington | ......... A61K 31/7048 |
| 9,358,293 B2 * | 6/2016 | Addington | ............... A61P 25/00 |
| 2002/0068098 A1 | 6/2002 | Babish | |
| 2002/0077350 A1 | 6/2002 | Babish | |
| 2006/0135443 A1 | 6/2006 | Khodadoust | |
| 2006/0234955 A1 | 10/2006 | Pollard | |
| 2007/0154573 A1 | 7/2007 | Rashan | |
| 2007/0249711 A1 | 10/2007 | Choi | |
| 2008/0200401 A1 | 8/2008 | Addington | |
| 2011/0022956 A1 | 9/2011 | Cain | |
| 2012/0128798 A1 | 5/2012 | Addington | |
| 2013/0267475 A1 | 10/2013 | Addington | |

(Continued)

FOREIGN PATENT DOCUMENTS

| | | |
|---|---|---|
| CN | 1301774 A1 | 2/2016 |
| EP | 2260851 A1 | 12/2010 |

(Continued)

OTHER PUBLICATIONS

Razboršek et al. ("Determination of oleanolic, betulinic and ursolic acid in Lamiaceae and mass spectral fragmentation of their trimethylsilylated derivatives." Chromatographia 67.5-6 (2008): 433-440.*

(Continued)

*Primary Examiner* — Svetlana M Ivanova
(74) *Attorney, Agent, or Firm* — Innovar, L.L.C.; Rick Matos

(57) ABSTRACT

A method of treating a triterpene-responsive condition, disease or disorder in a subject by administration of an improved triterpene-based composition is provided. An improved triterpene-based composition comprising at least two or at least three triterpenes present at a molar ratio as described herein is also provided.

15 Claims, 13 Drawing Sheets

(56) References Cited

U.S. PATENT DOCUMENTS

| | | | |
|---|---|---|---|
| 2015/0011627 A1 | 1/2015 | Gribble | |
| 2015/0283191 A1* | 10/2015 | Park | H04W 36/165 370/331 |
| 2016/0243143 A1* | 8/2016 | Addington | A61P 25/14 |
| 2017/0196890 A1* | 7/2017 | Yu | C07J 9/005 |
| 2017/0274031 A1 | 9/2017 | Addington | |

FOREIGN PATENT DOCUMENTS

| | | |
|---|---|---|
| EP | 1852105 B1 | 8/2015 |
| WO | 9932097 A2 | 7/1999 |
| WO | 0064921 A2 | 11/2000 |
| WO | 03099011 A1 | 12/2003 |
| WO | 2009/064657 A1 | 5/2009 |
| WO | 2018053123 A1 | 3/2018 |

OTHER PUBLICATIONS

Van Kanegan et al., Nature Scientific Reports (May 2016), 6:25626.*

Stack et al. ("Triterpenoids CDDO-ethyl amide and CDDO-trifluoroethyl amide improve the behavioral phenotype and brain pathology in a transgenic mouse model of Huntington's Disease" in Free Radic. Biol. Med. (2010), 49(2), 147-158).

Bai et al. ("Studies on Chemical Constituents of Japanese Nerium indicum Mill and Their Cytotoxicity in vitro" in J. Anhui Agri. Sci. (2009), 37(20), 9480-9488).

Wang et al. ("LC/MS/MS Analyses of an Oleander Extract for Cancer Treatment" in Anal. Chem. (2000), 72, 3547-3552).

Wang et al. ("Cardiac glycosides provide neuroprotection against ischemic stroke: discovery by a brain slice-based compound screening platform"). Proc. Natl. Acad. Sci. (Jul. 5, 2006), 103:27, pp. 10461-10466.

Yu et al. ("New Polysaccharide from Nerium indicum protects neurons via stress kinase signaling pathway") Brain Research, (2007), 1153, pp. 221-230.

Rodan et al. ("Stroke recurrence in children with congenital heart disease", Annals of Neurology (Jul. 2012), 72(1), 103-111).

Riikonen et al. ("Hereditary and acquired risk factors for childhood stroke", Neuropediatrics (Oct. 1994), 25(5), 227-233).

Dominiczak et al. ("Genetics of common polygenic stroke". Nature Genetics (Oct. 2003), 35(2), 116-117).

Grubb et al. ("Risks of stroke and current indications for cerebral revascularization in patients with carotid occlusion", Neurosurgery Clinics of North America (Jul. 2001), 12(3), 473-487).

Jensen et al. ("The promise and potential pitfalls of serum biomarkers for ischemic stroke and transient ischemic attack", The Neurologist (Jul. 2008), 14(4), 243-6).

Lasek-Bal et al. ("Cardiogenic stroke in the young", Postepy w Kardiologii Inerwencyjnej (2012), 8(2), 131-137).

Rizos et al. ("Evolution of stroke diagnosis in the emergency room—a prospective observational study", Cerebrovascular diseases (Basel, Switzerland), (2009), 28(5), 448-453).

Siddiqui et al. ("Oleanderol, a new pentacyclic triterpene from the leaves of Nerium oleander", J. Natur. Prod. (1988), 51(2), 229-233).

Jaeger et al. ("Pentacyclic triterpene distribution in various plants—rich sources for a new group of multi-potent plant extracts", Molecules (2009), 14(6), 2016-2031).

Karawya et al. ("Phytochemical study of Nerium oleander growing in Egypt. Preliminary investigation", United Arab Republic J. Pharm. Sci. (1970), 11(2), 193-209.

Lo et al. ("Dual activities of the anti-cancer drug candidate PBI-05204 provide neuroprotection in brain slice models for neurodegenerative diseases and stroke", Scientific Reports (2016), 6, 25626; doi:10.1038/srep25626).

Rong et al. ("Protective effects of oleanolic acid on cerebral ischemic damage in vivo and $H_2O_2$-induced injury in vitro"; Pharm. Bio. (2011), 49(1), 78-85) (abstract).

So et al. ("Anti-ischemic activities of aralia cordata and its active component, oleanolic acid"; Arch. Pharm. Res. (2009), 32(6), 923-932) (abstract).

Li et al. ("Ursolic acid promotes the neuroprotection by activating Nrf2 pathway after cerebral ischemia in mice"; Brain Res. (2013), 1497, 32-39) (abstract).

Garcia-Morales et al. ("Anti-inflammatory, antioxidant and anti-acetylcholinesterase activities of Bouvardia ternifolia: potential implications in Alzheimer's disease"; Arch. Pharm. Res. (2015), 38(7), 1369-1379).

Zhang et al. ("Ursolic acid reduces oxidative stress to alleviate early brain injury following experimental subarachnoid hemorrhage"; Neuroscience Letters (2014), 579, 12-17) (abstract).

Qian et al. ("Maslinic acid, a natural triterpenoid compound from Olea europaea, protects cortical neurons against oxygen-glucose deprivation-induced injury"; Eur. J. Pharmacol. (2011), 670(1), 148-153).

Yoo et al. ("Terpenoids as potential anti-Alzheimer's disease therapeutics"; Molecules (2012), 17(3), 3524-3538) (abstract).

Heo et al. ("Ursolic acid of Origanum majorana L. reduces Abeta-induced oxidative injury"; Mol. Cells (2002), 13(1), 5-11).

Chung et al. ("Inhibitory effect of ursolic acid purified from Origanum majoma L on the acetylcholinesterase"; Mol. Cells (2001), 11(2), 137-143).

Alqahtani et al. ("The Pentacyclic Triterpenoids in Herbal Medicines and Their Pharmacological Activities in Diabetes and Diabetic Complications", in Curr. Med. Chem. (2013), 20, 908-931).

Ayatollahi et al. ("Pentacyclic Triterpenes in Euphorbia microsciada with Their T-cell Proliferation Activity" in Iran. J. Pharm. Res. (2011), 10(2), 287-294).

Castellano et al. ("Biochemical Basis of the Antidiabetic Activity of Oleanolic Acid and Related Pentacyclic Triterpenes" in Diabetes (2013), 62, 1791-.

Caunii et al. ("Effects of Ursolic and Oleanolic Acid on SK-MEL-2 Melanoma Cells: In Vitro and In Vivo Assays" in Inter. J. Onc. (2017), 51, 1651-1660).

Choi et al. ("Betulinic acid synergistically enhances BMP2-induced bone formation via stimulating Smad 1/5/8 and p38 pathways" in J. Biomed. Sci. (2016), 23:45, 1-9).

Domingues et al. ("Supercritical Fluid Extraction of Eucalyptus globulus Bark—A Promising Approach for Triterpenoid Production" in Int. J. Mol. Sci. (2012), 13, 7648-7662).

Ebeling et al. ("From a Traditional Medicinal Plant to a Rational Drug: Understanding the Clinically Proven Wound Healing Efficacy of Birch Bark Extract" in PLOSONE (2014), 9(1), 1-18).

Ebert et al. ("Identification and Small Molecule Inhibition of an Activating Transcription Factor 4 (ATF4)-dependent Pathway to Age-related Skeletal Muscle Weakness and Atrophy" in J. Biol. Chem. (2015), 290(42), 25497-25511).

Feng et al. ("Inhibition of Human Neutrophil Elastase by Pentacyclic Triterpenes" in PLOSONE (2013), 8(12), 1-11).

Filomena ("Oleanolic, Ursolic and Betulinic Acids as Food Supplements or Pharmaceutical Agents for Type 2 Diabetes: Promise or Illusion?" in J. Agri. Food. Chem. (2016), 64, 2991-3008).

Fumiko et al. ("Ursolic Acid as a Trypanocidal Constituent in Rosemary" in Biol. Pharm. Bull. (2002), 25(110, 1485-1487).

Jager et al. ("Pentacyclic Triterpene Distribution in Various Plants—Rich Sources for a New Group of Multi-potent Plant Extracts" in Molec. (2009), 14, 2016-2031).

Jesus et al. ("Antimicrobial Activity of Oleanolic and Ursolic Acids: an Update" in Evidence-based Complementary and Alternative Medicine (2015), Article ID 620472, 14 pages, http://dx.doi.org/10.1155/2015/620472).

Jimenez-Arellanes et al. ("Ursolic and oleanolic acids as antimicrobial and immunomodulatory compounds for uberculosis treatment" in BMC Complem. Alter. Med. (2013), 13:258, 1-11).

Lee et al. ("Effects of Hydroxy Pentacyclic Triterpene Acids from Forsythia viridissima on Asthmatic Responses to Ovalbumin Challenge in Conscious Guinea Pigs" in Biol. Pharm. Bull. (2010), 33(2), 230-237).

Lopez et al. ("Phytochemical composition, antiparasitic and alpha-glucosidase inhibition activities from Pelliciera rhizophorae" in Chem. Centr. J. (2015), 9:53, 1-11).

(56) References Cited

OTHER PUBLICATIONS

Mishra et al. ("Isolation, Characterization, and Anticancer Potential of Cytotoxic Triterpenes from Betula utilis Bark" in PLOSONE (2016), DOI:10.1371/journal.pone.0159430, 1-14).

Silva et al. ("Bioactive Oleanane, Lupane and Ursane Triterpene Acid Derivatives" in Molec. (2012), 17, 12197-12205).

Wang et al. ("Antibacterial and Synergistic Activity of Pentacyclic Triterpenoids Isolated from Alstonia scholaris" in Molec. (2016), 21, 139, doi:10.3390/molecules21020139, 1-11).

Wu et al. ("Triterpenoid Contents and Anti-inflammatory Properties of the Methanol Extracts of Ligustrum Species leaves" in Molec. (2011), 16, 1-15, doi:10.3390/molecules16010001).

Yoo et al. ("Terpenoids as Potential Anti-Alzheimer's Disease Therapeutics" in Molec. (2012), 17, 3524-3538, doi:10.3390/molecules17033524).

Takeoka et al. ("Identification of Three Triterpenoids in Almond Hulls" in J. Agri. Food Chem. (2000), 48(8), 3437-3439).

Chen et al. ("Inhibition of *Escherichia coli* heat-labile enterotoxin-induced diarrhea by Chaenomeles speciosa" in J. Ethnopharm. (2007), 113, 233-239).

Furtado et al. ("Pentacyclic Triterpene Bioavailability: An Overview of In Vitro and In Vivo Studies" in Molec. (2017), 22, 400, 1-24; doi:10.3390/molecules22030400).

Fu et al. ("Three New triterpenes from Nerium Oleander and Biological Activity of the Isolated Compounds" in J. Nat. Prod. (2005), 68, 198-206).

\* cited by examiner

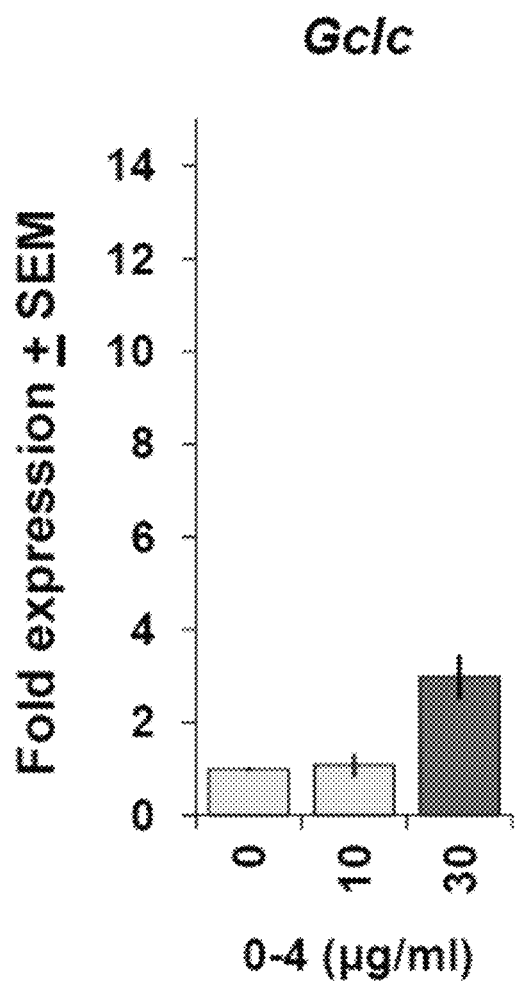
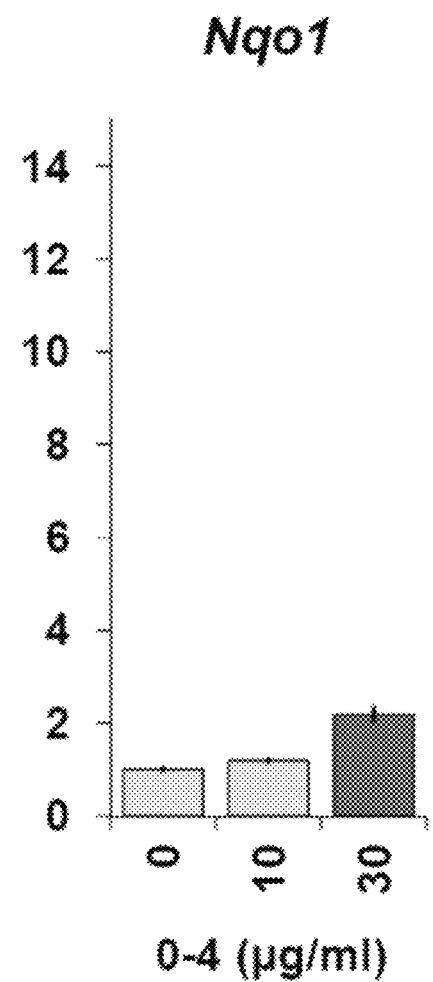
FIG. 2A (PRIOR ART)
FIG. 2B (PRIOR ART)

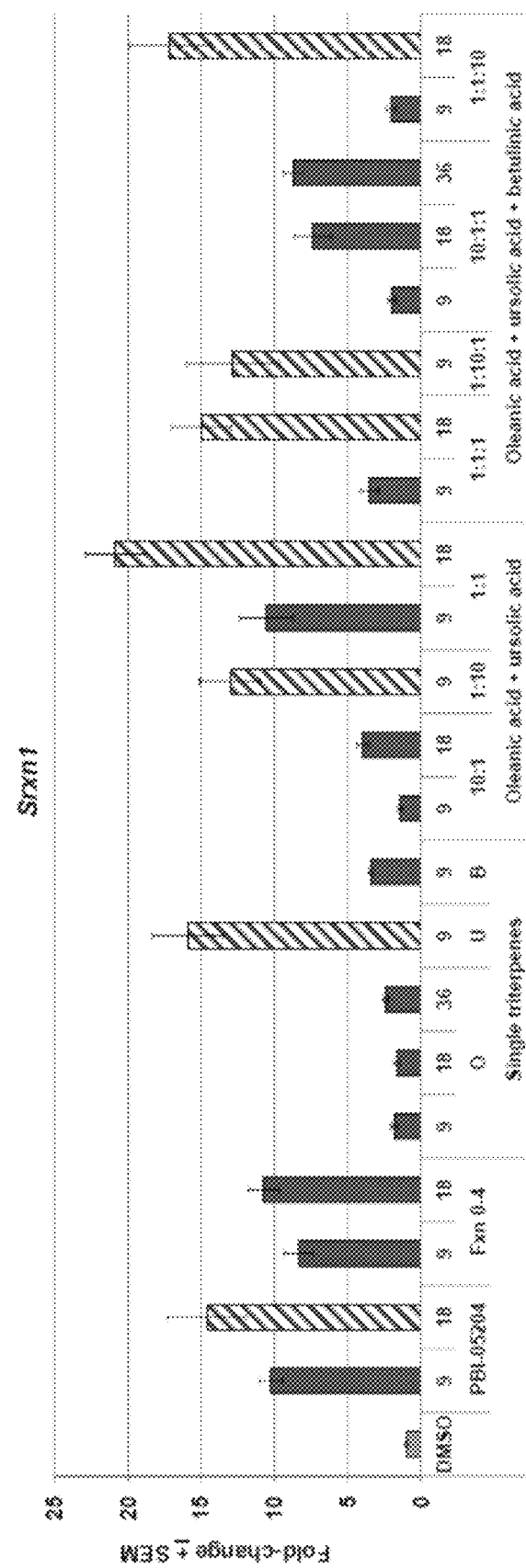

METHOD OF AND IMPROVED COMPOSITION FOR TREATING TRITERPENE-RESPONSIVE CONDITIONS, DISEASES OR DISORDERS

CROSS-REFERENCE TO EARLIER FILED APPLICATIONS

The present application is a continuation of application No. PCT/US2018/059818 filed on Nov. 8, 2018, which is a continuation-in-part of application No. PCT/US2018/049358 filed on Sep. 4, 2018, which claims the benefit of provisional application No. 62/558,631 filed on Sep. 14, 2017, and the present application is continuation-in-part of application No. PCT/2018/049358 filed on Sep. 4, 2018.

FIELD OF THE INVENTION

The present invention concerns a method of treating triterpene-responsive conditions, disease or disorders with an improved composition comprising a combination of triterpenes present at a molar ratio as described herein. In particular, the invention concerns a method of treatment by administration of a triterpene-based composition to a subject in need thereof. The invention also includes pharmaceutical compositions containing the improved composition.

BACKGROUND OF THE INVENTION

Neurological diseases and disorders affect brain function. Many efforts have been made to develop curative or ameliorative therapies for these diseases and disorders; however, no comprehensive or universally curative therapy has been developed, even though there are numerous pharmacotherapeutic approaches that have been proven to be effective against various different diseases and disorders.

Huntington's disease (HD) is an inherited disease of the brain that affects the nervous system. It is caused by a defective gene that is passed from parent to child. The HD gene interferes with the manufacture of a particular protein known as 'Huntington' which appears to be crucial for proper brain development. The classic signs of HD include emotional, cognitive and motor disturbances. Huntington's is characterized by jerky involuntary movements (chorea), but sometimes causes rigidity without abnormal movements, changes in using the limbs (apraxia), loss of control of bodily functions and dementia, including a progressive deterioration of memory, speed of thought, judgment, and lack of awareness of problems and planning. There is no known cure for Huntington's disease. Although there are a number of medications to help control symptoms associated with HD such as emotional and movement problems, there is no treatment to stop or reverse the course of the disease. Huntington's disease has been recognized as a disease with a general membrane abnormality. A significantly elevated level and activity (10 fold increase) of Na,K-ATPase has been observed in membranes of erythrocytes and basal ganglia of Huntington's patients compared to that of normal (Butterfield D A, Oeswein J Q, Prunty M E, Hisle K C, Markesbery W R). Increased sodium, potassium adenosine triphosphatase activity in erythrocyte membranes in Huntington's disease. Ann Neurology, 4:60-62, 1978) fibroblast membranes obtained from the skin of Huntington's disease patients (Schroeder F, Goetz I E, Roberts E, Membrane anomalies in Huntington's disease fibroblasts. J. Neurochem. 43: 526-539, 1984).

Alzheimer's disease is a form of dementia—a neurodegenerative disease that damages the brain's intellectual functions (memory, orientation, calculation, etc.), but usually preserves its motor functions. In Alzheimer's disease, the mind gradually deteriorates, causing memory loss, confusion, disorientation, impaired judgment and other problems that may affect a person's ability to perform normal daily activities. The type, severity, sequence and progression of mental changes vary greatly. There is no known cure for Alzheimer's disease and no known way to slow its progression. For some people in the early or middle stages of the disease, medication such as tacrine may alleviate some cognitive symptoms. Aricept (donepezil) and Exelon (rivastigmine) are reversible acetylcholinesterase inhibitors that are indicated for the treatment of mild to moderate dementia of the Alzheimer's type. These drugs (called cholinesterase inhibitors) work by increasing the brain's levels of the neurotransmitter acetylcholine, helping to restore communication between brain cells. Some medications may help control behavioral symptoms such as sleeplessness, agitation, wandering, anxiety, and depression. These treatments are aimed at making the patient more comfortable. Although no medication is known to cure Alzheimer's disease, cholinesterase inhibitors may improve performance of daily activities, or lessen behavioral problems. Medications for the treatment of Alzheimer's disease currently being tested include estrogens, nonsteroidal anti-inflammatory agents, vitamin E, selegiline (Carbex, Eldepryl) and the botanical product gingko *biloba*.

Triterpenes are known to possess a wide variety of therapeutic activities. Some of the known triterpenes include oleanolic acid, ursolic acid, betulinic acid, bardoxolone, maslinic acid, and others. The therapeutic activity of the triterpenes has primarily been evaluated individually rather than as combinations of triterpenes.

Rong et al. (Pharm. Biol. (January 2011), 49(1), 78-85) suggest oleanolic acid might be suitable for attenuating ischemic stroke. So et al. (Arch. Pharm. Res. (June 2009), 32(6), 923-932) suggest oleanolic acid might be suitable for the prevention and treatment of neurodegeneration in stroke. Li et al. (Brain Res. (February 2013), 1497, 32-39) suggest ursolic acid might provide neuroprotection after cerebral ischemia in mice. Garcia-Morales et al. (Arch. Pharm. Res. (July 2015), 38(7), 1369-1379) suggest that an extract of *Bouvardia ternifolia* should be further studied for treating Alzheimer's disease. Zhang et al. (Neuroscience Letters (2014), 579, 12-17) report that ursolic acid reduces oxidative stress following experimental subarachnoid hemorrhage. Qian et al. (Eur. J. Pharmacol. (2011), 670(1), 148-153) report that maslinic acid protects cortical neurons against oxygen-glucose deprivation-induced injury in rats. EP 2260851 A1 to Consejo Superior de Investigaciones Cientificas (Madrid, E S) suggests the use of oleanolic acid for the treatment of multiple sclerosis. Yoo et al. (Molecules, (May 2012), 17(3), 3524-38) suggest the use of terpenoids as anti-Alzheimer's disease therapeutics. Heo et al. (Mol. Cells (February 2002), 13(1), 5-11) suggest ursolic acid reduces amyloid beta protein-induced oxidative cell death. Chung et al. (Mol. Cells (April 2001), 11(2), 137-143) suggest ursolic acid appears to be a potent inhibitor of acetylcholinesterase in Alzheimer's disease. US 2007/0249711 A1 (Pub. Date. Oct. 25, 2007) to Choi et al. suggests the use of oleanolic acid and ursolic acid for improving brain functions to prevent and treat mild cognitive impairment and dementia.

Oleanolic acid is in a class of triterpenoids typified by compounds such as bardoxolone which have been shown to be potent activators of the innate cellular phase 2 detoxifying pathway, in which activation of the transcription factor Nrf2 leads to transcriptional increases in programs of downstream antioxidant genes containing the antioxidant transcriptional response element (ARE). Bardoxolone itself has been extensively investigated in clinical trials in inflammatory conditions; however, a Phase 3 clinical trial in chronic kidney disease was terminated due to adverse events that may have been related to known cellular toxicities of certain triterpenoids including bardoxolone at elevated concentrations.

Compositions containing triterpenes in combination with other therapeutic components are found as plant extracts. Fumiko et al. (Biol. Pharm. Bull (2002), 25(11), 1485-1487) discloses the evaluation of a methanolic extract of *Rosmarimus officinalis* L. for treating trypanosomiasis. Addington et al. (U.S. Pat. Nos. 8,481,086, 9,220,778, 9,358,293, US 20160243143 A1) disclose a supercritical fluid extract (SCF; PBI-05204) of *Nerium oleander* containing oleandrin and triterpenes for the treatment of neurological conditions. Addington et al. (U.S. Pat. No. 9,011,937, US 20150283191 A1) disclose a triterpene-containing fraction (PBI-04711) of the SCF extract of *Nerium oleander* containing oleandrin and triterpenes for the treatment of neurological conditions. Jager et al. (Molecules (2009), 14, 2016-2031) disclose various plant extracts containing mixtures of oleanolic acid, ursolic acid, betulinic acid and other components. Mishra et al. (PLoS One 2016 25; 11(7):e0159430. Epub 2016 Jul. 25) disclose an extract of *Betula utilis* bark containing a mixture of oleanolic acid, ursolic acid, betulinic acid and other components. Wang et al. (Molecules (2016), 21, 139) disclose an extract of *Alstonia scholaris* containing a mixture of oleanolic acid, ursolic acid, betulinic acid and other components. L. e Silva et al. (Molecules (2012), 17, 12197) disclose an extract of *Eriope blanchetti* containing a mixture of oleanolic acid, ursolic acid, betulinic acid and other components. Rui et al. (Int. J. Mol. Sci. (2012), 13, 7648-7662) disclose an extract of *Eucaplyptus globulus* containing a mixture of oleanolic acid, ursolic acid, betulinic acid and other components. Ayatollahi et al. (Iran. J. Pharm. Res. (2011), 10(2), 287-294) disclose an extract of *Euphorbia microsciadia* containing a mixture of oleanolic acid, ursolic acid, betulinic acid and other components. Wu et al. (Molecules (2011), 16, 1-15) disclose an extract of *Ligustrum* species containing a mixture of oleanolic acid, ursolic acid, betulinic acid and other components. Lee et al. (Biol. Pharm. Bull (2010), 33(2), 330) disclose an extract of *Forsythia viridissima* containing a mixture of oleanolic acid, ursolic acid, betulinic acid and other components. Wozniak et al. (Molecules (2015), 20, 20614-20641) disclose various therapeutic activities of ursolic acid. Liby et al. (Pharmacol. Rev. (2012), 64:972-1003) disclose various therapeutic activities of synthetic oleanane triterpenoids.

Oleanolic acid (O or OA), ursolic acid (U or UA) and betulinic acid (B or BA) are the three major triterpene components found in PBI-05204 (PBI-23; a supercritical fluid extract of *Nerium oleander*) and PBI-04711 (a triterpene-containing fraction 0-4 of PBI-05204). We (two of the instant inventors) previously reported (Van Kanegan et al., in Nature Scientific Reports (May 2016), 6:25626. doi: 10.1038/srep25626) on the contribution of the triterpenes toward efficacy by comparing their neuroprotective activity in a brain slice oxygen glucose deprivation (OGD) model assay at similar concentrations. We found that PBI-05204 (PBI) and PBI-04711 (Fraction 0-4) provide neuroprotective activity (FIG. 1). We then evaluated the neuroprotective activity of the three major individual triterpenes and of uvaol (Uva) individually in the OGD assay on an equimolar basis (FIG. 5). We found that OA provides higher activity than UA; whereas BA and Uva (uvaol) provide little to no activity at the concentrations tested. We found that the activity of UA in this assay exhibited variable activity in a concentration dependent manner. We postulated activation of nuclear factor erythroid 2 related factor (Nrf2)-dependent antioxidant genes as a potential mechanism for the underlying neuroprotective activity of PBI-04711 and the individual triterpenes. Therefore, employing an ARE-luciferase promoter-reporter assay, we determined the ability of those compositions to activate the Nrf2-ARE (antioxidant transcriptional response element) gene pathway in neurons using a corticostriatal primary neuronal co-culture system composed of the neuronal and glial cell types as in the brain slice OGD assay. We found (FIGS. 2A-2D) that PBI-04711 increased expression of canonical target ARE genes (glutamate-cysteine ligase, catalytic subunit (Gclc); NAD(P)H: quinone oxidoreductase 1 (Nqo1); sulfiredoxin antioxidant protein (Srx); and heme oxygenase 1 (Hmox1)) via activation of the transcription factor NRF2 that mediates the cellular antioxidant defense pathway. However, when comparing this activity of the individual triterpenes to that of PBI-04711 (FIG. 3), we found that UA appeared to be considerably more potent, as single agent, in inducing ARE gene expression compared to BA and OA, meaning the induction of Srx and Hmox1 is due more so to the activity of UA than of OA or BA, but UA still exhibits lower activity in the neuroprotection OGD assay. We found that while UA and BA are most active at gene expression, they are also very toxic at concentrations that are just 2-3-fold higher than concentrations required to induce gene expression. This means that UA and BA have narrow therapeutic windows. Our prior results suggested that UA and BA would likely be too toxic to achieve doses that would realize the full ARE-inducing activity in vivo. Our prior results also suggested that OA was relatively inactive on its own, so it would be unlikely that the combination of triterpenes (in PBI-05204 and PBI-04711) at their molar ratios could achieve substantially improved neuroprotective activity at doses that are not toxic at a cellular level.

U.S. Pat. Nos. 8,481,086, 9,220,778 9,358,293, and US 2016-0243143 A1 disclose the use of PBI-05204 for the treatment of neurological conditions. U.S. Pat. No. 9,011,937 and US 2015-0283191 A1 disclose the use of PBI-04711 for the treatment of neurological conditions.

Compositions containing plural triterpenes in certain molar ratios have been reported to be undesirable. Compositions comprising ursolic acid and oleanolic acid were evaluated to determine their impact upon platelet aggregation. Kim et el. ("Enhancement of platelet aggregation by ursolic acid and oleanolic acid" in Biomol. Therap. (2014), 22(3), 254-259) reported that the triterpenes potentiated platelet aggregation and "need to be used with caution, especially in the population with a predisposition to cardiovascular events".

None of the art suggests a composition containing a combination of three different triterpenes selected from oleanolic acid, ursolic acid and betulinic acid, nor use of such a composition for the treatment of triterpene-responsive conditions, diseases, or disorders, wherein the triterpenes are present in the molar ratios as defined herein. None of the art recognizes the improvements provided by administration of such a combination of triterpenes as compared to administration of the individual triterpenes or administration of other combinations of triterpenes.

SUMMARY OF THE INVENTION

The present inventors have discovered that the clinical benefit provided by compositions containing two or more triterpenes, salts thereof, derivatives thereof and/or prodrugs thereof can be improved to reduce adverse events and improve efficacy. Said improvement is achieved by controlling the molar ratio of the triterpenes relative to one another. The invention provides an improved composition comprising a combination of two or more triterpenes or three or more triterpenes, wherein the molar ratio of the triterpenes is as described herein. The instant triterpene-based composition, with the specified molar ratio of triterpenes, exhibits reduced cellular toxicity and increased efficacy as compared to the respective individual triterpenes on a total-triterpene equimolar basis.

It is an object of the invention to provide an improved triterpene-based composition comprising plural triterpenes as the active ingredients thereof, wherein the composition provides increased ARE gene expression, and reduced cellular toxicity as compared to other closely related triterpene-based compositions on an equimolar basis.

It is another object of the invention to provide an improved triterpene-based composition that provides a balanced expression of ARE genes to provide clinical benefit over a wide dosing range without resulting in excessive cellular toxicity.

It is another object of the invention to provide an improved triterpene-based composition that provides a broader dose response curve and a broader (wider) therapeutic window as compared to other closely related triterpene-based compositions on a total equimolar basis. The improved composition provides a broader therapeutic window, meaning a wider dosing range along with lower toxicity especially at the upper limits of the dosing range, as compared to other closely related triterpene-based compositions on an equimolar basis.

The composition of the invention provides a greater than additive clinical benefit, meaning a synergistic clinical benefit, e.g. synergistic efficacy, as compared to the individual triterpenes.

The invention provides an improved method of treating a condition, disease or disorder that is therapeutically responsive to triterpene (free base thereof, salt(s) thereof, derivative(s) thereof, and/or prodrug(s) thereof) and/or metabolite(s) thereof, the method comprising administering to a subject in need thereof a composition comprising at least three triterpenes, wherein the molar ratio of the triterpenes is as described herein. Said condition, disease or disorder can be identified according to the methods described herein or according to methods known in the art for determining, modeling or predicting therapeutic responsiveness. The invention also includes methods of preventing said condition, disease or disorder. The invention excludes conditions, diseases or disorders that are not therapeutically responsive to said triterpenes or metabolite(s) thereof.

An important clinical benefit provided by the improved composition is a substantially expanded therapeutic window as compared to the individual triterpenes administered on a total-triterpene equimolar basis.

Another important clinical benefit provided by the improved composition is substantially improved efficacy as compared to the individual triterpenes administered on a total-triterpene equimolar basis.

Another important clinical benefit provided by the improved composition is substantially reduced adverse events as compared to the individual triterpenes administered on a total-triterpene equimolar basis.

Embodiments of the invention includes those wherein the condition, disease or disorder is selected from the group consisting of: a) autoimmune condition, disease or disorder; b) neurological condition, disease or disorder; c) anti-inflammatory response-related condition, disease or disorder; d) microbial infection; e) viral infection; f) bacterial infection; g) musculoskeletal condition, disease or disorder; h) excessive cell proliferation related condition, disease or disorder; i) protozoal infection; j) oxidative stress-related condition, disease or disorder; k) gastrointestinal condition, disease or disorder; l) angiogenesis-related condition, disease or disorder; m) cyclooxygenase-related condition, disease or disorder; n) cardiovascular condition, disease or disorder; o) hepatic condition, disease or disorder; p) age-related condition, disease or disorder; q) bone-related condition, disease or disorder; r) dermatological condition, disease or disorder; s) parasitic infection; t) renal condition, disease or disorder; u) metabolic condition, disease or disorder; v) gastrointestinal condition, disease or disorder; and w) pulmonary condition, disease or disorder.

Embodiments of the invention includes those wherein: a) the autoimmune condition, disease or disorder is selected from the group consisting of alopecia areata, celiac disease, diabetes mellitus type 1, Graves' disease, inflammatory bowel disease, multiple sclerosis, psoriasis, rheumatoid arthritis, and systemic lupus erythematosus; b) the neurological condition, disease or disorder as defined herein; c) the viral infection is selected from the group consisting of HSV-1 strain 1C, influenza A H7N1, ECHO 6, HIV-1, HEP C, HCV H strain NS5B, HSV-1, HSV-2, ADV-3, ADV-8, ADV-11, HEP B, ENTV CVB1, ENTV EV71, viral hemorrhagic fever (VHF), Arenaviridae infection, Bunyaviridae infection, Filoviridae infection, Flaviviridae infection, Paramyxoviridae infection, Togaviridae infection, Filovirus infection, Flavivirus infection, Henipavirus infection, alphavirus infection, Togavirus infection, Ebolavirus, Marburgvirus, Alphavirus, Flavivirus, Yellow Fever, Dengue Fever, Japanese Enchephalitis, West Nile Viruses, Zikavirus, Venezuelan Equine Encephalomyelitis (encephalitis) (VEE) virus, Chikungunya virus, Western Equine Encephalomyelitis (encephalitis) (WEE) virus, Eastern Equine Encephalomyelitis (encephalitis) (EEE) virus, Tick-borne Encephalitis, Kyasanur Forest Disease, Alkhurma Disease, Omsk Hemorrhagic Fever, Hendra virus, Nipah virus, and species thereof; d) the bacterial infection is selected from the group consisting of *Aeromonas caveae* infection, *Bacillus cereus* infection, *Bacillus sphaericus* infection, *Bacillus subtilis* infection, *Enterococcus faecalis* infection, *Escherichia coli* infection, *Klebisiella pneumoniae* infection, *Listeria monocytogenes* infection, *Mycobacterium tuberculosis* infection, *Pseudomonas aeruginosa* infection, *Pseudomonas syrinagae* infection, *Ralstonia solanacearum* infection, *Shigella flexneri* infection, *Staphylococcus aureus* infection, *Staphylococcus epidermis* infection, *Streptococcus mutans* infection, *Streptococcus pneumoniae* infection, *Streptococcus sobrinus* infection, *Streptomyces* scabies infection, *Vibrio cholerae* infection, vancomycin-resistant enterococci infection, methicillin-resistant *Staphylococcus aureus* infection, and proteobacteria infection; e) the musculoskeletal condition, disease or disorder is selected from the group consisting of skeletal muscle atrophy, muscular atrophy, muscular dysfunction, amyotrophic lateral sclerosis, and sarcopenia; f) the excessive cell proliferation related condition, disease or disorder is selected from the group consisting of cancer, tumor, colorectal cancer, head and neck cancer, adrenal cortical cancer, anal cancer, bile duct cancer, bladder cancer, bone cancer, bone metastasis, sarcomas of bone, brain cancer, breast cancer, cervical cancer, non-Hodgkin's lymphoma, rectal cancer, esophageal cancer, eye cancer, gallbladder cancer, gastrointestinal carcinoid tumor, gestational trophoblastic disease, Hodgkin's disease, Kaposi's sarcoma, kidney cancer, laryngeal and hypopharyngeal cancer, liver cancer, lung cancer (both non-small cell and small cell carcinomas), lung carcinoid tumors, malignant mesothelioma, metastatic cancer, multiple myeloma, myelodysplastic syndrome, nasal cavity and paranasal cancer, nasopharyngeal cancer, neuroblastoma, neoplasms of the central nervous system, oral cavity and oropharyngeal cancer, osteosarcoma, ovarian cancer, pancreatic cancer, penile cancer, pituitary cancer, prostate cancer, retinoblastoma, salivary gland cancer, sarcoma, skin cancer, stomach cancer, testicular cancer, thymus cancer, thyroid cancer, cancer of the ureter; uterine sarcoma, vaginal cancer, vulva cancer or Wilm's tumor; g) the protozoal infection is selected from the group consisting of *Leishmania amazonensis* infection, *Plasmodium falciparum* infection, *Trypanosoma brucei rhodesiense* infection, *Trypanosoma cruzi* infection, and malaria; h) the cardiovascular condition, disease or disorder is selected from the group consisting of myocardial infarction, stroke, atherosclerosis, hypertension, varicose veins, and damage caused by C-reactive protein; i) the hepatic condition, disease or disorder is selected from the group consisting of hepatic lipid accumulation, hepatic steatosis, hepatic fibrosis, and hepatic degeneration (degradation); j) the bone-related condition, disease or disorder is selected from the group consisting of osteoporosis, and particle induced osteolysis; k) the renal condition, disease or disorder is selected from the group consisting of nephrotic syndrome, and focal segmental glomerulosclerosis; or l) the pulmonary condition, disease or disorder is selected from the group consisting of acute lung injury, chronic obstructive pulmonary disorder, and asthma.

In some embodiments, the neurological condition is selected from the group consisting of neurological disease, neurological disorder, tauopathy, and stroke. In some embodiments, the neurological disease is a neurodegenerative disease. In some embodiments, the neurodegenerative disease is selected from the group consisting of Hungtinton's disease, Alzheimer's disease, Parkinson's disease, amyotrophic lateral sclerosis, bovine spongiform encephalopathy, multiple sclerosis, diabetic neuropathy, autism and juvenile neuronal ceroid lipofuscinosis. In some embodiments, stroke is stroke-mediated ischemic injury. In some embodiments, the neurological condition is a tauopathy, which is a neurodegenerative disease having an etiology associated with an imbalance in the Tau3R/Tau4R ratio in a subject. Tauopathies are a class of neurodegenerative diseases resulting from the pathological aggregation of tau proteins in the human brain. In some embodiments, the tauopathy is Down's syndrome, Pick's disease, corticobasal degeneration, some variants of prions disease, Alzheimer's disease, progressive supranuclear palsy or frontotemporal dementia. The individual steps of the methods of the invention can be conducted at separate facilities or within the same facility.

The invention provides an improved method of treating a triterpene-responsive condition, disease or disorder comprising administering to a subject in need thereof an improved composition comprising (consisting essentially of) at least three triterpenes. The molar ratio of triterpenes has been found to impact efficacy and toxicity/safety of the composition(s). Embodiments of the invention include those wherein the molar ratio of triterpenes is as described herein. The molar ratio of triterpenes in the improved composition is different than and improved over that found in PBI-05204 and PBI-04711.

In some embodiments, the composition contains triterpenes as the sole pharmacologically active ingredients (agents). The composition can exclude steroid, cardiac glycoside, biologically/pharmacologically active polysaccharide, and/or non-cardiac glycoside steroid.

In one aspect, the invention provides a method of treating, in a subject in need thereof, a triterpene-responsive condition, disease or disorder with a composition comprising at least two or at least three triterpenes present at a molar ratio as described herein, the method comprising:
determining that the subject has a triterpene-responsive condition, disease or disorder; and
indicating administration of a therapeutically effective amount of said composition to the subject.

The invention also provides a method of treating, in a subject in need thereof, a condition, disease or disorder that is therapeutically responsive to triterpene and/or metabolite thereof with a triterpene-based composition, the method comprising administering to the subject a therapeutically effective amount of said triterpene-based composition, wherein the molar ratio of triterpenes in said composition are as described herein.

In one aspect, the invention provides a method of treating, in a subject in need thereof, a neurological condition, disease or disorder with a neuroprotective composition comprising at least two or at least three triterpenes, the method comprising: determining that the subject has a neurological condition, disease or disorder; and indicating administration of a therapeutically effective amount of the neuroprotective composition to the subject.

The invention also provides a method of treating, in a subject in need thereof, a neurological disease or disorder with a neuroprotective composition, the method comprising administering to the subject a therapeutically effective amount of the neuroprotective composition.

Some embodiments of the invention include those wherein: 1) the subject is prescribed and administered a therapeutically relevant dose of the composition; 2) the subject is administered the composition according to a prescribed dosing regimen; 3) the composition excludes cardiac glycoside; 4) the composition excludes a therapeutically effective amount of cardiac glycoside; 5) the composition excludes oleandrin; 6) the composition excludes a neriifolin; 7) the composition excludes a pharmacologically active polysaccharide obtained from *Nerium* species or *Thevetia* species; 8) the composition comprises a synthetic mixture of at least two or at least three triterpenes present at a molar ratio as described herein; or 9) a combination of any two or more of the above.

The invention also provides a method of treating a neurological condition in a subject in need thereof comprising:
determining whether or not the neurological condition in the subject is Alzheimer's disease, Huntington's disease, stroke, Parkinson's disease or other neurological condition;
indicating administration of a neuroprotective composition;
administering an initial dose of the neuroprotective composition to the subject according to a prescribed initial dosing regimen for a period of time;

periodically determining the adequacy of the subject's clinical response and/or therapeutic response to treatment with the neuroprotective composition; and if the subject's clinical response and/or therapeutic response is adequate, then continuing treatment with the neuroprotective composition as needed until the desired clinical endpoint is achieved; or if the subject's clinical response and/or therapeutic response are inadequate at the initial dose and initial dosing regimen, then escalating or deescalating the dose of the neuroprotective composition until the desired clinical response and/or therapeutic response in the subject is achieved.

The invention also provides a method of preventing or reducing the incidence of occurrence of a triterpene-responsive condition, disease or disorder in a population of subjects at risk thereof, the method comprising:

administering an effective dose of a triterpene-based composition on a recurring basis for an extended period of time to one or more subjects in said population of subjects, thereby preventing or reducing the incidence of said condition, disease or disorder in the population; wherein the composition comprises at least two or at least three triterpenes selected from the group consisting of oleanolic acid, ursolic acid, and betulinic acid, each of said triterpenes being present in a form which is independently selected upon each occurrence from the group consisting of free acid form, salt form, derivative form and prodrug form, and the molar ratio of said triterpenes being as described herein.

The invention also provides a method of preventing or reducing the incidence of occurrence of a neurological condition in a population of subjects at risk thereof, the method comprising:

administering an effective dose of neuroprotective composition on a recurring basis for an extended period of time to one or more subjects in a population of subjects at risk of suffering from a neurological condition such as Alzheimer's disease, Huntington's disease, Parkinson's disease, stroke or other neurological condition, thereby preventing or reducing the incidence of the neurological condition in the population; wherein said neuroprotective composition comprises at least two or at least three triterpenes selected from the group consisting of oleanolic acid, ursolic acid, and betulinic acid, each of said triterpenes being present in a form which is independently selected upon each occurrence from the group consisting of free acid form, salt form, derivative form and/or prodrug form, and the molar ratio of said triterpenes being as described herein.

The invention also includes embodiments wherein: a) the method further comprises indicating administration of the neuroprotective composition to the one or more subjects; b) the method further comprises administering an effective dose of the neuroprotective composition to the subject according to a prescribed dosing regimen for a period of time; c) the method further comprises periodically determining the adequacy of one or more subject's clinical response and/or therapeutic response to treatment with the neuroprotective composition; d) if the subject's clinical response and/or therapeutic response is adequate, then the method further comprises continuing treatment with the neuroprotective composition as needed until the desired clinical endpoint is achieved; e) if the subject's clinical response and/or therapeutic response are inadequate at the initial dose and initial dosing regimen, then the method further comprises escalating or deescalating the dose of neuroprotective composition until the desired clinical response and/or therapeutic response in the subject is achieved; f) the neuroprotective composition is administered to plural subjects in a population; g) the recurring basis is daily, every other day, every second day, every third day, every fourth day, every fifth day, every sixth day, weekly, every other week, every second week, every third week, monthly, bimonthly, semi-monthly, every other month every second month, quarterly, every other quarter, trimesterly, seasonally, semiannually and/or annually; h) the extended period is one or more weeks, one or more months, one or more quarters and/or one or more years; i) the effective dose is administered one or more times in a day; j) the method further comprises identifying a population of subjects at risk of suffering from a neurological condition such as Alzheimer's disease, Huntington's disease, Parkinson's disease, stroke or other neurological condition; k) the population of subjects at risk is characterized by advancing age of the subject, familial history of the neurological condition, genetic predisposition to occurrence of neurological condition, the presence and expression of ApoE4 gene in the subject, female gender (twice as many women get Alzheimer's disease than men), cardiovascular disease (e.g. high blood pressure and high cholesterol levels), diabetes (especially Type 2 or adult onset forms of this disease), Down's Syndrome, head injury, low levels of formal education, smoking, excessive alcohol consumption and/or drug abuse; or l) a combination thereof.

The invention also provides a time-delayed method of treating stroke in a subject comprising:

within a delay period after a subject has suffered the stroke, administering an initial dose of neuroprotective composition according to an initial dosing regimen;

determining the adequacy of subject's clinical response and/or therapeutic response to treatment with the neuroprotective composition; and if the subject's clinical response and/or therapeutic response is adequate, then continuing treatment with neuroprotective composition as needed until the desired clinical endpoint is achieved; or if the subject's clinical response and/or therapeutic response are inadequate at the initial dose and initial dosing regimen, then escalating or deescalating the dose of neuroprotective composition until the desired clinical response and/or therapeutic response in the subject is achieved.

Some embodiments of the invention include those wherein: 1) the delay period is 10 hours or less, 8 hours or less, 6 hours or less, 4 hours or less, 3 hours or less, 2 hours or less, 1 hour or less, 45 minutes or less, 30 minutes or less, 20 minutes or less or 10 min or less; 2) determining the adequacy of a subject's clinical and/or therapeutic response is done by assessments of any weakness of the face, arm and/or leg on one side of the body, numbness in the face, arm, and/or leg on one side of the body, inability to understand spoken language, inability to speak or speak clearly, inability to write, vertigo and/or gait imbalance, double vision and an unusually severe headache; or 3) a combination thereof.

The invention also provides use of a triterpene-based composition in the manufacture of a medicament for the treatment of a triterpene-responsive condition, disease or disorder in a subject. In some embodiments, the manufacture of such a medicament comprises: providing said composition; including a dose of said composition in a pharmaceutical dosage form; and packaging the pharmaceutical dosage form.

The invention also provides a pharmaceutical composition comprising said composition for the treatment of a condition, disease or disorder in a subject. The manufacture can also include one or more additional steps such as: delivering the packaged dosage form to a vendor (retailer, wholesaler and/or distributor); selling or otherwise providing the packaged dosage form to a subject having a neurological condition; including with the medicament a label and a package insert, which provides instructions on use, dosing regimen, administration, content and toxicology profile of the dosage form.

In some embodiments, the treatment of a triterpene-responsive condition, disease or disorder comprises: determining that a subject has a triterpene-responsive condition, disease or disorder; indicating administration of said composition to the subject according to a dosing regimen; administering to the subject one or more pharmaceutical dosage forms containing said composition, wherein the one or more pharmaceutical dosage forms is administered according to the dosing regimen.

In some embodiments, the subject having a neurological condition, i.e. the subject in need thereof, is part of a population of such subjects. The invention provides a method for improving the clinical status of a statistically significant number of subjects of in a population of subjects having a neurological condition, the method comprising: administering to the population of subjects a neuroprotective composition as described herein; and determining the clinical status of the subjects. In some embodiments, the statistically significant number is at least 5% of the population.

In some embodiments, the neurological condition is Alzheimer's disease, Huntington's disease, stroke, Parkinson's disease, a tauopathy or other neurological condition, such as described herein.

Treatment of the subject with said composition is continued as needed. The dose or dosing regimen can be adjusted as needed until the patient reaches the desired clinical endpoint(s) such as a reduction or alleviation of specific symptoms associated with the condition, disease or disorder being treated. Determination of the adequacy of clinical response and/or therapeutic response can be conducted by a clinician familiar with the condition, disease or disorder being treated.

Embodiments of the invention also include a triterpene-based improved composition comprising at least two or at least three triterpenes, wherein: said triterpenes are present at a molar ratio as described herein; and said triterpenes are selected from the group consisting of oleanolic acid, ursolic acid, and betulinic acid, each of said triterpenes being present in a form which is independently selected upon each occurrence from the group consisting of free acid form, salt form, derivative form, and prodrug form.

In some embodiments, the invention provides a triterpene-based improved composition exhibiting therapeutic activity as described herein when administered to a subject. In some embodiments, the methods of the invention employ said composition as described herein.

In each embodiment of the invention, a triterpene is independently upon each occurrence present in native form (unmodified free acid, unmodified salt or combination thereof form), derivative form, prodrug form, or a combination of two or more of said forms. For example, a triterpene can be present as a mixture of free acid form and salt form, or a mixture of free acid form and derivative form, or a mixture of free acid form and prodrug form, or a mixture of two or more forms, or a mixture of three or more forms. The term "triterpene" as used herein refers to each form or any of said forms or any mixture of said forms. The table below specifies various combinations of triterpene forms.

| Sample | Triterpene Form Present (Y/N) | | | |
|---|---|---|---|---|
| | Free acid | Salt | Derivative | Prodrug |
| Combination 1 | Y | Y | N | N |
| Combination 2 | Y | N | Y | N |
| Combination 3 | Y | N | N | Y |
| Combination 4 | N | Y | Y | N |
| Combination 5 | N | Y | N | Y |
| Combination 6 | N | N | Y | Y |
| Combination 7 | N | Y | N | Y |
| Combination 8 | Y | Y | Y | N |
| Combination 9 | Y | N | Y | Y |
| Combination 10 | Y | Y | N | Y |
| Combination 11 | N | Y | Y | Y |
| Combination 12 | Y | Y | Y | Y |

Embodiments of the invention include those wherein the triterpene-based improved composition is a neuroprotective composition comprising (consisting essentially of) at least two triterpenes present at a molar ratio as described herein. In some embodiments, the neuroprotective composition of the invention comprises (consists essentially of) at least three triterpenes present at a molar ratio as described herein.

In some embodiments, the composition of the invention comprises (consists essentially of) oleanolic acid (free acid, salt, derivative, and/or prodrug thereof) and ursolic acid (free acid, salt, derivative, and/or prodrug thereof) and optionally at least one other triterpene, wherein the molar ratio of triterpenes is as described herein. For example, the composition can further comprise betulinic acid (free acid, salt, derivative, and/or prodrug thereof) or at least one other triterpene.

In some embodiments, the composition of the invention comprises (consists essentially of) oleanolic acid (free acid, salt, derivative, and/or prodrug thereof) and betulinic acid (free acid, salt, derivative, and/or prodrug thereof) and optionally at least one other triterpene, wherein the molar ratio of triterpenes is as described herein. For example, the composition can further comprise ursolic acid (free acid, salt, derivative, and/or prodrug thereof) or at least one other triterpene.

Some embodiments of the invention provide a composition comprising (consisting essentially of) at least oleanolic acid (free acid, salt, derivative, and/or prodrug thereof), betulinic acid (free acid, salt, derivative, and/or prodrug thereof), and ursolic acid (free acid, salt, derivative, and/or prodrug thereof), wherein the molar ratio of said triterpenes is as described herein.

Some embodiments of the invention provide an improved composition comprising (consisting essentially of) at least: oleanolic acid (present as free acid and/or salt thereof), betulinic acid (present as free acid and/or salt thereof), and ursolic acid (present as free acid and/or salt thereof), wherein the molar ratio of said compounds is as described herein.

A pharmaceutical dosage form comprises the composition and one or more pharmaceutically acceptable excipients.

In some embodiments, the composition comprises (consists essentially of) the triterpenes oleanolic acid, ursolic acid, and betulinic acid, wherein the molar ratio of triterpenes is as described herein. In some embodiments, the composition is included in a pharmaceutical composition further comprising at least one pharmaceutically acceptable excipient.

In some embodiments, the majority of pharmacologically active component in the composition is oleanolic acid. Oleanolic acid can be present in molar excess over ursolic acid and/or over betulinic acid. Oleanolic acid can be present in molar excess over the combined total moles of ursolic acid and betulinic acid. Oleanolic acid and ursolic acid can together (sum total) or individually be present in molar excess over betulinic acid. Oleanolic acid and betulinic acid can together (sum total) or individually be present in molar excess over ursolic acid. Ursolic acid and betulinic acid can be present at about the same content. Ursolic acid can be present in molar excess over betulinic acid. Betulinic acid can be present in molar excess over ursolic acid.

Embodiments of the invention include those wherein: a) oleanolic acid is present in molar excess over the combined total moles of ursolic acid and betulinic acid, and ursolic acid and betulinic acid are present at about the same molar content; b) oleanolic acid is present in molar excess over the combined total moles of ursolic acid and betulinic acid, and ursolic acid is present in molar excess over betulinic acid; c) oleanolic acid is present in molar excess over the combined total moles of ursolic acid and betulinic acid, and betulinic acid is present in molar excess over ursolic acid; d) oleanolic acid is present in molar excess over ursolic acid, and ursolic acid is present in molar excess over betulinic acid; or e) oleanolic acid is present in molar excess over betulinic acid, and betulinic acid is present in molar excess over ursolic acid.

When oleanolic acid (free acid, salt, derivative, and/or prodrug thereof), ursolic acid (free acid, salt, derivative, and/or prodrug thereof) and betulinic acid (free acid, salt, derivative, and/or prodrug thereof) are present as the primary or sole triterpenes, the molar ratio of oleanolic acid (O):ursolic acid (U):betulinic acid (B) is about 10:about 1:about 1, about 9-11:about 0.5-1.5:about 0.5-1.5, about 9.5-10.5:about 0.75-1.25:about 0.75-1.25, about 9.5-10.5:about 0.8-1.2:about 0.8-1.2, about 9.75-10.5:about 0.9-1.1:about 0.9-1.1, about 9-12:about 0.15-2.5:about 0.15-2.5, about 9-12:about 0.2-2.5:about 0.2-2.5, about 9-12:about 0.25-2.5:about 0.25-2.5, about 9-12:about 0.35-2.5:about 0.35-2.5, about 9-12:about 0.45-2.5:about 0.45-2.5, about 9-12:about 0.5-5:about 0.5-2.5, about 9-12:about 0.16-2:about 0.16-2, about 9-12:about 0.2-2:about 0.2-2, about 9-12:about 0.25-2:about 0.25-2, about 9-12:about 0.25-2, about 9-12:about 0.45-2:about 0.45-2, about 9-12:about 0.5-2:about 0.5-2, about 9-12:about 0.16-1.5:about 0.16-1.5, about 9-12:about 0.2-1.5:about 0.2-1.5, about 9-12:about 0.25-1.5:about 0.25-1.5, about 9-12:about 0.7-1.5:about 0.35-1.5, about 9-12:about 0.45-1.5:about 0.45-1.5, about 9-12:about 0.5-1.5:about 0.5-1.5, about 9-12:about 0.16-1:about 0.16-1, about 9-12:about 0.2-1:about 0.2-1, about 9-12:about 0.25-1:about 0.25-1, about 9-12:about 0.35-1:about 0.35-1, about 9-12:about 0.45-1:about 0.45-1, about 9-12:about 0.5-1:about 0.5-1, about 10-1:about 0.5-2.5:about 0.5-2.5, about 10-1:about 0.1-1.5: about 0.1-1.5, about 9-12:about 0.25-0.75:about 0.25-0.75, about 9.5-10.5:about 0.35-0.7:about 0.35-0.7, about 9.5-10.5:about 0.4-0.6:about 0.4-0.6, or about 9.75-10.5:about 0.45-0.6:about 0.45-0.6.

When oleanolic acid (free acid, salt, derivative, and/or prodrug thereof) and ursolic acid (free acid, salt, derivative, and/or prodrug thereof) are present as the primary or sole triterpenes, the molar ratio of oleanolic acid:ursolic acid is about 9-12:about 0.33-5, about 9-12:about 0.4-5, about 9-12:about 0.5-5, about 9-12:about 0.7-5, about 9-12:about 0.9-5, about 9-12:about 1-5, about 9-12:about 0.33-4, about 9-12:about 0.4-4, about 9-12:about 0.5-4, about 9-12:about 0.7-4, about 9-12:about 0.9-4, about 9-12:about 1-4, about 9-12:about 0.33-3, about 9-12:about 0.4-3, about 9-12:about 0.5-3, about 9-12:about 0.7-3, about 9-12:about 0.9-3, about 9-12:about 1-3, about 9-12:about 0.33-2, about 9-12:about 0.4-2, about 9-12:about 0.5-2, about 9-12:about 0.7-2, about 9-12:about 0.9-2, about 9-12:about 1-2, about 10-1:about 1-5, about 10-1:about 1-3, about 9-12:about 0.5-1.5, about 9-11:about 0.5-1.5, about 9.5-10.5:about 0.75-1.25, about 9.5-10.5:about 0.8-1.2, or about 9.75-10.5:about 0.9-1.1.

When oleanolic acid (free acid, salt, derivative, and/or prodrug thereof) and betulinic acid (free acid, salt, derivative, and/or prodrug thereof) are present as the primary or sole triterpenes, the molar ratio of oleanolic acid:betulinic acid is about 9-12:about 0.33-5, about 9-12:about 0.4-5, about 9-12:about 0.5-5, about 9-12:about 0.7-5, about 9-12: about 0.9-5, about 9-12:about 1-5, about 9-12:about 0.33-4, about 9-12:about 0.4-4, about 9-12:about 0.5-4, about 9-12: about 0.7-4, about 9-12:about 0.9-4, about 9-12:about 1-4, about 9-12:about 0.33-3, about 9-12:about 0.4-3, about 9-12:about 0.5-3, about 9-12:about 0.7-3, about 9-12:about 0.9-3, about 9-12:about 1-3, about 9-12:about 0.33-2, about 9-12:about 0.4-2, about 9-12:about 0.5-2, about 9-12:about 0.7-2, about 9-12:about 0.9-2, about 9-12:about 1-2, about 10-1:about 1-5, about 10-1:about 1-3, about 9-12:about 0.5-1.5, about 9-11:about 0.5-1.5, about 9.5-10.5:about 0.75-1.25, about 9.5-10.5:about 0.8-1.2, or about 9.75-10.5: about 0.9-1.1.

The individual steps of the methods of the invention can be conducted at separate facilities or within the same facility. Any of the methods of the invention described herein can be used in combination with any of the compositions of the invention described herein.

The invention includes all combinations of the aspects, embodiments and sub-embodiments of the invention disclosed herein.

BRIEF DESCRIPTION OF THE FIGURES

The following figures form part of the present description and describe some of the prior art and exemplary embodiments of the claimed invention. The skilled artisan will, in light of these figures and the description herein, be able to practice the invention without undue experimentation.

FIGS. 2A-2D (prior art: Van Kanegan: vide supra) depict the results of ARE gene expression assays for Fraction 0-4 (PBI-04711): a) Gclc expression (FIG. 2A); b) Nqo1 expression (FIG. 2B); c) Srx expression (FIG. 2C); and d) Hmox1 expression (FIG. 2D). Primary mouse corticostriatal co-cultures were treated with Fraction 0-4 at the concentrations indicated for 6 h, then harvested and processed for qPCR analysis of the ARE target genes shown. Quantitative RNA values are normalized to the GAPDH reference control and fold-expression changes are expressed relative to the DMSO-carrier only condition ("0") set to a value of 1.

FIG. 9A); Composition II: molar ratio of O:U:B is 7.8:7.4:1 as in PBI-05204 (FIG. 9B); and Composition III: molar ratio of O:U:B is about 10:1:1 as per the improved composition of the invention (PBI-01011; FIG. 9C)) determined in a brain slice assay for ischemic stroke according to Example 3. Numbers of healthy cortical pyramidal neurons per brain slice are shown relative to the negative control condition set to 100% (second bar in each graph) of brain slices exposed to oxygen-glucose deprivation (OGD) and vehicle (DMSO) only. Values for positive control brain slices not exposed to OGD are shown in the first bar of each graph. Mean values+SEM are shown averaged over 3-5 independent runs for each triterpene mixture; light blue bars denote statistically significant differences with respect to the OGD negative control by ANOVA followed by Dunnett's post hoc comparison test at $p<0.05$.

FIGS. 10A and 10B depict the results of comparative Srx (FIG. 10A) and Hmox1 (FIG. 10B) expression assays for PBI-05204, PBI-04711 (also referred to as Fxn 0-4), oleanolic acid (O), ursolic acid (U), betulinic acid (B) and combinations of the triterpenes present at the specified molar ratios. Quantitative RNA values were normalized to the GAPDH reference control and fold-expression changes are shown relative to the DMSO-carrier only condition set to a value of 1. Dark blue bars denote statistically significant differences with respect to the DMSO-carrier only control by a Student's t-test at $p<0.05$. Striped, red bars denote conditions which induced excessive levels of ARE gene expression, namely, by more than 10-fold.

DETAILED DESCRIPTION OF THE INVENTION

Figure 1:
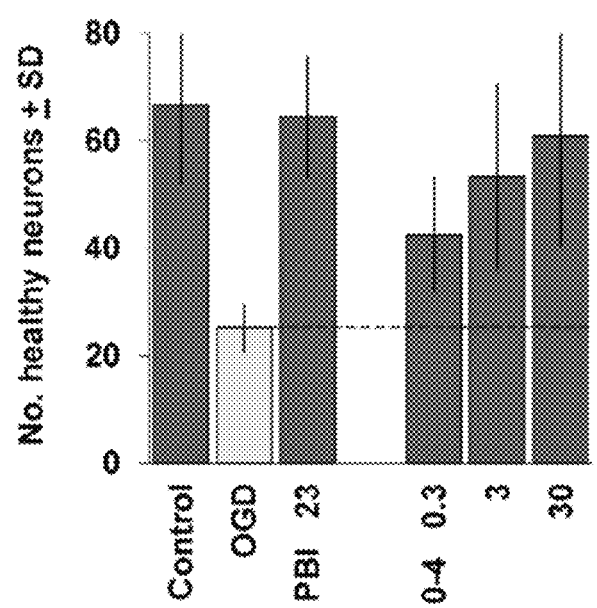
FIG. 1 (prior art; Van Kanegan: vide supra) depicts the results of the comparative evaluation of PBI-05204 (PBI) and PBI-04711 (Fraction 0-4 of PBI-05204) in a brain slice oxygen-glucose deprivation (OGD) assay. Coronal brain slice explants were prepared and subjected to 5.5 min transient OGD. Numbers of healthy cortical pyramidal neurons in each brain slice were scored 24 h later. The first 3 bars in the graph show: control brain slices not subjected to OGD ("Control"); negative-control brain slices subjected to OGD and treated with DMSO carrier only ("OGD"); and positive-control brain slices subjected to OGD and treated with 23 ng/ml of the full PBI-05204 extract ("PBI 23"). The fraction was tested at the concentrations indicated in units of ng/ml. Fraction 0-4 provided significant neuroprotection at the concentrations tested (concentrations of Fraction 0-3 of 10 ng/ml and above exhibited toxicity; data not shown).
Figure 2C:
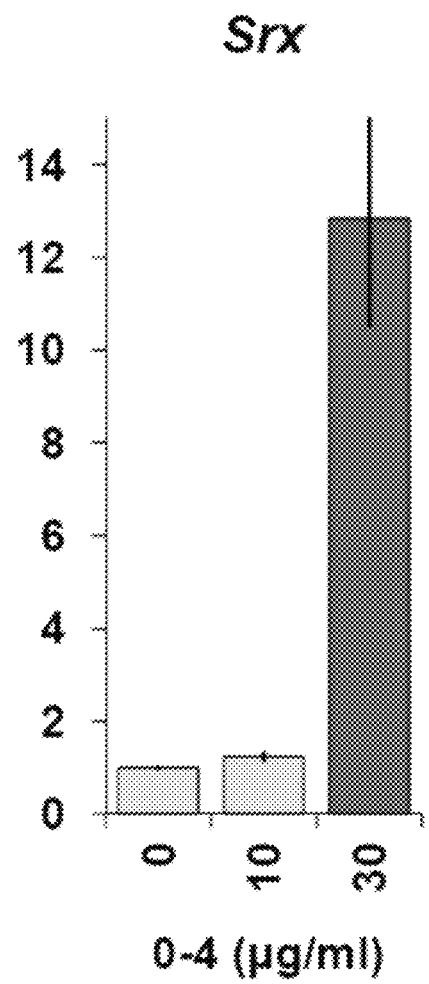
Figure 2D:
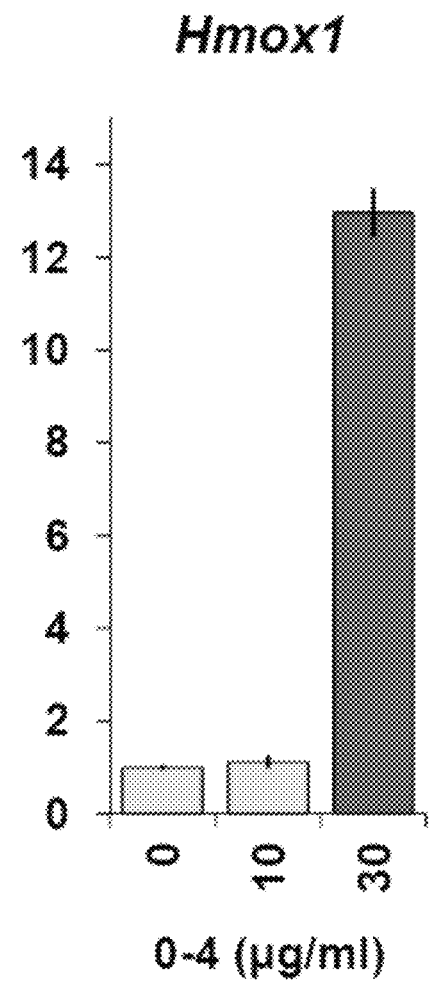
Figure 3:
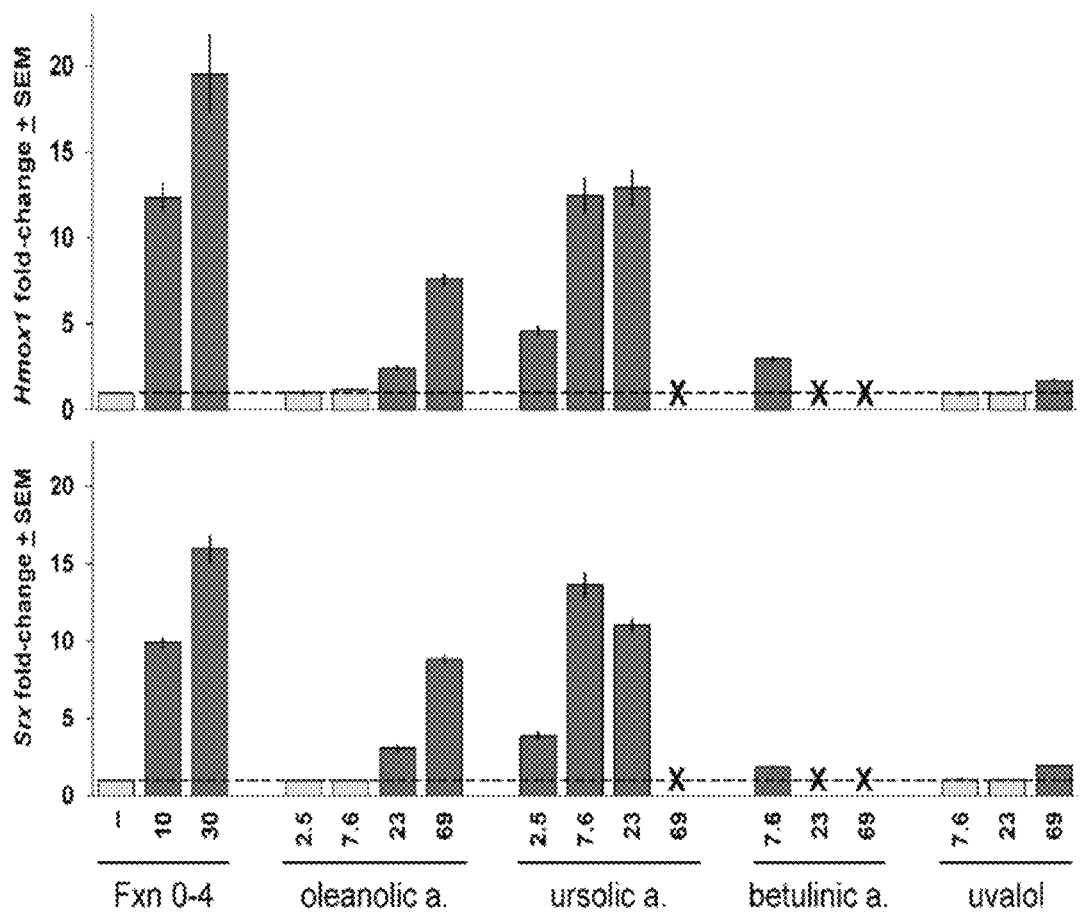
FIG. 3 (prior art: Van Kanegan: vide supra) depicts the results of ARE gene expression assays for Fraction 0-4 and the individual triterpenes oleanolic acid, ursolic acid, betulinic acid and uvaol (also referred to as uvalol). "X" symbols denote concentrations of compounds which induced toxicity and for which recovery of residual mRNA was insufficient to support qPCR analysis. Rat primary corticostriatal co-cultures were treated for 6 h with Fraction 0-4 (in µg/ml) or oleanolic acid, ursolic acid, betulinic acid, or uvaol (all in µM) at the concentrations indicated, then harvested and processed for qPCR analysis of the ARE target genes shown. Quantitative RNA values were normalized to the GAPDH reference control and fold-expression changes are expressed relative to the DMSO-carrier only condition ("--") set to a value of 1. Dark bars denote statistically significant differences with respect to the DMSO-carrier only control by a Student's t-test at $p<0.05$.

As used herein, the individually named triterpenes can independently be selected upon each occurrence in their native (unmodified) free acid form, native salt form, derivative form, prodrug form, or a combination thereof. Compositions containing and methods employing deuterated forms of the triterpenes are also within the scope of the invention. The total moles of a triterpene present in a composition is the sum total of the moles of each form of said triterpene. For example, the total moles of "oleanolic acid" present in a composition is the sum total of moles of native free acid form+native salt form(s)+derivative form(s)+prodrug form(s).

Oleanolic acid derivatives, prodrugs and salts are disclosed in US 20150011627 A1 to Gribble et al. which published Jan. 8, 2015, US 20140343108 A1 to Rong et al which published Nov. 20, 2014, US 20140343064 A1 to Xu et al. which published Nov. 20, 2014, US 20140179928 A1 to Anderson et al. which published Jun. 26, 2014, US 20140100227 A1 to Bender et al. which published Apr. 10, 2014, US 20140088188 A1 to Jiang et al. which published Mar. 27, 2014, US 20140088163 A1 to Jiang et al. which published Mar. 27, 2014, US 20140066408 A1 to Jiang et al. which published Mar. 6, 2014, US 20130317007 A1 to Anderson et al. which published Nov. 28, 2013, US 20130303607 A1 to Gribble et al. which published Nov. 14, 2013, US 20120245374 to Anderson et al. which published Sep. 27, 2012, US 20120238767 A1 to Jiang et al. which published Sep. 20, 2012, US 20120237629 A1 to Shode et al. which published Sep. 20, 2012, US 20120214814 A1 to Anderson et al. which published Aug. 23, 2012, US 20120165279 A1 to Lee et al. which published Jun. 28, 2012, US 20110294752 A1 to Arntzen et al. which published Dec. 1, 2011, US 20110091398 A1 to Majeed et al. which published Apr. 21, 2011, US 20100189824 A1 to Arntzen et al. which published Jul. 29, 2010, US 20100048911 A1 to Jiang et al. which published Feb. 25, 2010, and US 20060073222 A1 to Arntzen et al. which published Apr. 6, 2006, the entire disclosures of which are hereby incorporated by reference.

Ursolic acid derivatives, prodrugs and salts are disclosed in US 20150011627 A1 to Gribble et al. which published Jan. 8, 2015, US 20130303607 A1 to Gribble et al. which published Nov. 14, 2013, US 20150218206 A1 to Yoon et al. which published Aug. 6, 2015, U.S. Pat. No. 6,824,811 to Fritsche et al. which issued Nov. 30, 2004, U.S. Pat. No. 7,718,635 to Ochiai et al. which issued May 8, 2010, U.S. Pat. No. 8,729,055 to Lin et al. which issued May 20, 2014, and U.S. Pat. No. 9,120,839 to Yoon et al. which issued Sep. 1, 2015, the entire disclosures of which are hereby incorporated by reference.

Betulinic acid derivatives, prodrugs and salts are disclosed in US 20150011627 A1 to Gribble et al. which published Jan. 8, 2015, US 20130303607 A1 to Gribble et al. which published Nov. 14, 2013, US 20120237629 A1 to Shode et al. which published Sep. 20, 2012, US 20170204133 A1 to Regueiro-Ren et al. which published Jul. 20, 2017, US 20170096446 A1 to Nitz et al. which published Apr. 6, 2017, US 20150337004 A1 to Parthasaradhi Reddy et al. which published Nov. 26, 2015, US 20150119373 A1 to Parthasaradhi Reddy et al. which published Apr. 30, 2015, US 20140296546 A1 to Yan et al. which published Oct. 2, 2014, US 20140243298 A1 to Swidorski et al. which published Aug. 28, 2014, US 20140221328 A1 to Parthasaradhi Reddy et al. which published Aug. 7, 2014, US 20140066416 A1 tp Leunis et al. which published Mar. 6, 2014, US 20130065868 A1 to Durst et al. which published Mar. 14, 2013, US 20130029954 A1 to Regueiro-Ren et al. which published Jan. 31, 2013, US 20120302530 A1 to Zhang et al. which published Nov. 29, 2012, US 20120214775 A1 to Power et al. which published Aug. 23, 2012, US 20120101149 A1 to Honda et al. which published Apr. 26, 2012, US 20110224182 to Bullock et al. which published Sep. 15, 2011, US 20110313191 A1 to Hemp et al. which published Dec. 22, 2011, US 20110224159 A1 to Pichette et al. which published Sep. 15, 2011, US 20110218204 to Parthasaradhi Reddy et al. which published Sep. 8, 2011, US 20090203661 A1 to Safe et al. which published Aug. 13, 2009, US 20090131714 A1 to Krasutsky et al. which published May 21, 2009, US 20090076290 to Krasutsky et al. which published Mar. 19, 2009, US 20090068257 A1 to Leunis et al. which published Mar. 12, 2009, US 20080293682 to Mukherjee et al. which published Nov. 27, 2008, US 20070072835 A1 to Pezzuto et al. which published Mar. 29, 2007, US 20060252733 A1 to Jansen et al. which published Nov. 9, 2006, and US 2006025274 A1 to O'Neill et al. which published Nov. 9, 2006, the entire disclosures of which are hereby incorporated by reference.

When a derivative or prodrug of a triterpene is used, the moles of each is determined according to the molar equivalents of the parent free acid triterpene. For example, one mole of the methyl ester derivative of oleanolic acid (methyl oleanolate) is the molar equivalent of one mole of oleanolic acid and vice versa.

The invention provides a method of treating a triterpene-responsive condition, disease or disorder by administration of an effective dose (therapeutically effective dose) of a triterpene-based composition of the invention to a subject in need thereof. The composition is administered according to a dosing regimen best suited for the subject, the suitability of the dose and dosing regimen to be determined clinically according to conventional clinical practices and clinical treatment endpoints for the condition, disease or disorder being treated.

In some embodiments, the neurodegenerative disorder or neurological condition being treated has an etiology associated with an over-expression of tau proteins and/or an imbalance in the Tau3R/Tau4R ratio in a subject. Such a condition is termed a tauopathy. Exemplary tauopathies include Down's syndrome, Pick's disease, some variants of prions disease, Alzheimer's disease, progressive supranuclear palsy or frontotemporal dementia, corticobasal degeneration, Guam parkinsonism dementia complex, dementia with argyrophilic grains, Niemann-Pick disease Type C, and dementia pugilistic.

In some embodiments, the neurodegenerative disorder or neurological condition being treated has an etiology associated with abnormal or atypical proteolysis of amyloid beta precursor protein, accumulation of amyloid beta protein in the synapses of the neurons, formation of amyloid fibrils in the synapses of the neurons, or formation of amyloid plaques in the synapses of the neurons. Exemplary of such disorders or conditions is Alzheimer's disease. A subject treated according to the invention will exhibit a therapeutic response.

By "therapeutic response" is meant that a subject suffering from the disease or disorder will enjoy at least one of the following clinical benefits as a result of treatment with the triterpene-based composition: amelioration of the disease or disorder, reduction in the occurrence of symptoms associated with the disease or disorder, partial remission of the disease or disorder, full remission of the disease or disorder, or increased time to progression. In other words, the therapeutic response can be a full or partial therapeutic response. Accordingly, a triterpene-responsive condition, disease or disorder is one against which the triterpene-based composition will provide or exhibit a therapeutic response in a subject.

A therapeutic response can also be described as one in which the quality of life of the patient afflicted with the condition, disease or disorder is improved. Improvement in quality of life may occur, for example, through a reduction in occurrence, frequency or severity of symptoms associated with the condition, disease or disorder. For example, for a neurological condition, improvement in quality of life may be reduced tremors, reduced involuntary muscle movements, reversal of loss or partial loss of nerve-muscle coordination, increased memory retention, etc.

The methods of the invention include methods of treating as well as prophylactic methods of preventing. Methods of treating are those methods wherein the subject receiving the composition of the invention is already suffering from a specified condition, disease or disorder. Methods of preventing are those methods wherein the subject receiving the composition of the invention is not yet suffering from a specified condition, disease or disorder.

"Preventing occurrence of a condition, disease or disorder in a population of subjects at risk" means that said condition, disease or disorder will not occur during a predetermined time period in a demographically predetermined population of subjects that are at risk of suffering from the same. The prevention during the predetermined time period occurs as a result of subjects in that population having been administered a composition according to the invention. A composition of the invention can be administered prophylactically to prevent any of the conditions, diseases or disorders disclosed herein as well as etiologically-related conditions, diseases or disorders.

As one example, when a neuroprotective composition is administered for a predetermined time period to subjects in a population of subjects at risk of suffering from stroke, stroke will not occur in those subjects during the predetermined time period. In particular, a neuroprotective composition is chronically administered over a period of one year to a population of subjects at risk of suffering from Alzheimer's disease or any of the tauopathology related diseases, and the subjects in that population do not exhibit symptoms associated with Alzheimer's during that one-year period.

"Reducing the incidence of occurrence of a condition, disease or disorder in a population of subjects at risk" is related in meaning to "preventing the incidence", except that "reducing the incidence of occurrence" permits the occurrence of the condition, disease or disorder in a demographically predetermined population of subjects but at a rate of occurrence or a level of severity that is reduced as compared to an otherwise demographically similar predetermined population of subjects at risk not being administered the composition according to the invention.

As used herein, "time to progression" is the period, length or duration of time after a disease is diagnosed (or treated) until the disease begins to worsen. It is the period of time during which the level of a disease is maintained without further progression of the disease, and the period of time ends when the disease begins to progress again. Progression of a disease is determined by "staging" a subject suffering from a condition prior to or at initiation of therapy.

For example, the subject's neurological health is determined prior to or at initiation of therapy. The subject is then treated with the neuroprotective composition, and the neurological health monitored periodically. At some later point in time, the symptoms of the neurological condition may worsen, thus marking progression of the disease and the end of the "time to progression". The period of time during which the disease did not progress or during which the level or severity of the disease did not worsen is the "time to progression".

A dosing regimen includes a therapeutically relevant dose (or therapeutically effective dose) of triterpene-based composition administered according to a dosing schedule. A therapeutically relevant dose, therefore, is a therapeutic dose at which a therapeutic response of the condition, disease or disorder to treatment with said composition is observed and at which a subject can be administered said composition without an excessive amount of unwanted or deleterious side effects. A therapeutically relevant dose is non-lethal to a subject, even though it may cause some side effects (adverse events) in the patient. It is a dose at which the level of clinical benefit to a subject being administered said composition exceeds the level of deleterious side effects experienced by the subject due to administration of said composition.

A therapeutically relevant dose will vary from subject to subject according to a variety of established pharmacologic, pharmacodynamic and pharmacokinetic principles. However, a therapeutically relevant dose will typically be in the range of 0.1 to 100 micrograms of said composition, being in either solid, liquid or semisolid form. It is known in the art that the actual amount of a pharmacologically active component/agent required to provide a target therapeutic result in a subject may vary from subject to subject according to the basic principles of pharmacy.

A therapeutically relevant (effective) dose can be administered according to any dosing regimen typically used in the treatment of conditions, diseases or disorders disclosed herein. A therapeutically relevant dose can be administered once, twice, thrice or more daily dosing schedule. It can be administered every other day, every third day, every fourth day, every fifth day, semiweekly, weekly, biweekly, every three weeks, every four weeks, monthly, bimonthly, semimonthly, every three months, every four months, semiannually, annually, or according to a combination of any of the above to arrive at a suitable dosing schedule. For example, a therapeutically relevant dose can be administered once daily for one or more weeks.

The examples below include evidence of the efficacy of the neuroprotective composition in treating neurological conditions such as neurological diseases, neurological disorders and stroke. Example 7 details a method of treating Alzheimer's disease with a neuroprotective composition or a combination of neuroprotective composition with one or more other therapeutic agents. Example 8 details a method of treating Huntington's disease with a neuroprotective composition or a combination of neuroprotective composition with one or more other therapeutic agents. Example 9 details a method of treating stroke-mediated and non-stroke mediated ischemic brain injury with a neuroprotective composition or a combination of neuroprotective composition with one or more other therapeutic agents. Example 10 details a method of Parkinson's disease with a neuroprotective composition or a combination of neuroprotective composition with one or more other therapeutic agents.

In general, a subject having a neurological condition is treated as follows. A subject presenting with a neurological condition is evaluated to determine whether or not the neurological condition is Alzheimer's disease, Huntington's disease, stroke, Parkinson's disease or other neurological condition. If the subject has a positive diagnosis, administration of the neuroprotective composition is indicated. Initial doses of the composition are administered to the subject according to a prescribed dosing regimen for a period of time. The subject's clinical response and level of therapeutic response are determined periodically. If the level of therapeutic response is too low at one dose, then the dose is escalated according to a predetermine dose escalation schedule until the desired level of therapeutic response in the subject is achieved. If the subject exhibits undesirable side effects or an unacceptable level of side effects, then the dose is deescalated until the desired balance of level of therapeutic response versus side effect profile in the subject is achieved. Treatment of the subject with the neuroprotective composition is continued as needed. The dose or dosing regimen can be adjusted as needed until the patient reaches the desired clinical endpoint(s) such as cessation of the disease itself, reduction in disease associated symptoms, and/or a reduction in the progression of the disease process.

Example 3 provides a detailed description of an in vitro assay used to evaluate the efficacy of the neuroprotective composition for the treatment of stroke-mediated ischemic neuronal injury. The assay is a brain slice-based assay for oxygen and glucose deprivation (OGD) used to induce 50% loss of healthy cortical neurons by 24 hours. The sample vehicle is used as a positive control.

Figure 9A:
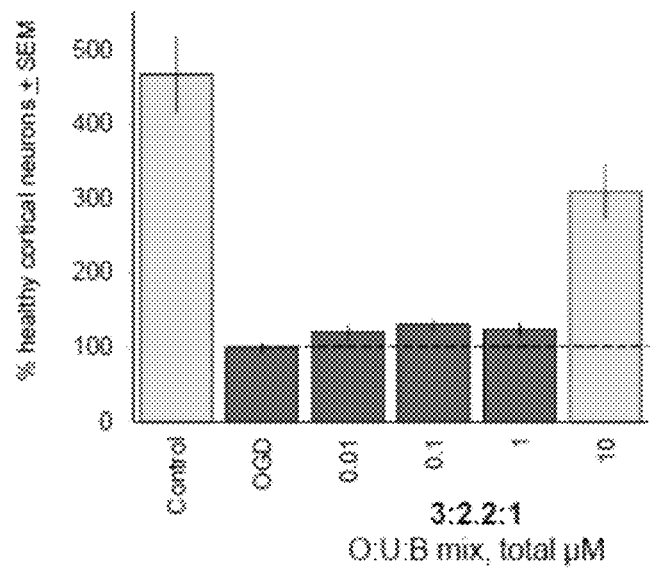
FIGS. 9A-9C depict the results of comparative neuroprotection of triterpene mixtures (Composition I: molar ratio of O:U:B is 3:2.2:1 as in PBI-04711 (Fxn 0-4.
Figure 9B:
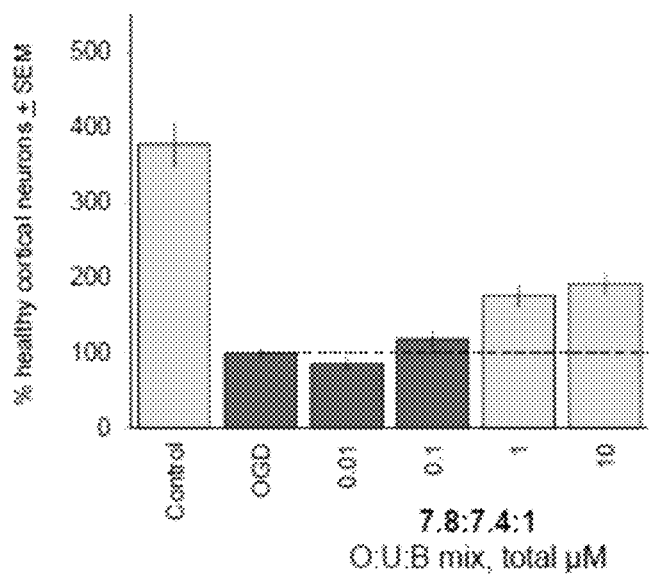
Figure 9C:
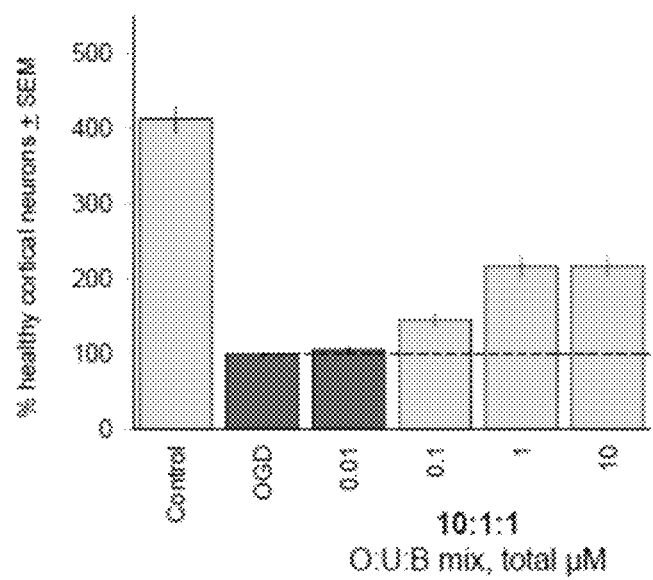

Various compositions were tested in OGD treated brain slices (stroke model) and non-OGD treated (i.e. control) brain slices (non-stroke model). Data (FIGS. 9A-9C) were obtained for Composition I (triterpene molar ratio similar to PBI-04711), Composition II (triterpene molar ratio similar to PBI-05204) and Composition III (triterpene molar ratio similar to PBI-01011). The data indicate that each of the compositions provide neuroprotection, but the improved neuroprotective composition (Composition III) provides neuroprotection across a wider dosing range (wider concentration range). For example, Composition I provides neuroprotection at 10 μM but does not provide neuroprotection at a concentration of 1 μM or less. Composition II provides neuroprotection at 1 μM and 10 μM but does not provide neuroprotection at a concentration of 0.1 μM or less. On the other hand, Composition III provides neuroprotection at 0.1 μM (100 Nm), 1 μM and 10 μM.

Accordingly, the improved neuroprotective composition provides a wider dosing range or wider dose response than other triterpene-based compositions on a total equimolar basis. The improved composition allows for administration of higher doses of the combination of triterpenes without substantially increasing the undesired adverse events (side effects) that might be caused by the individual triterpenes. On a practical basis, a clinician can administer high or low doses of the triterpene mixture and still expect low occurrence of triterpene-related adverse events.

The invention provides a method of protecting neurons against loss of activity caused by oxygen depletion or oxygen-glucose depletion by exposing the oxygen depleted and/or glucose-depleted neurons to an effective amount of improved triterpene-based neuroprotective composition to minimize loss of activity, reduce the rate of loss of activity, stop the loss of activity, slow down onset of loss of activity, and/or protect the function of neurons caused by exposing the oxygen depleted and/or glucose-depleted conditions.

Figure 6A:
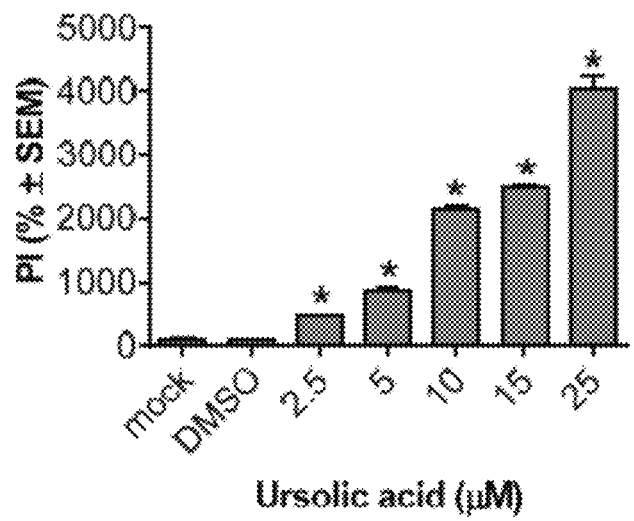
FIGS. 6A, 6B, 7A, 7B, 8A, and 8B depict the results of comparative cellular toxicities of the triterpenes to primary corticalstriatal neuronal co-cultures containing glia evaluated according to the example below: ursolic acid (FIGS. 6A, 6B), betulinic acid (FIGS. 7A, 7B) and oleanolic acid (FIGS. 8A, 8B). For FIGS. 6A, 7A and 8A, propidium iodide was added for one hour then the numbers of PI-positive cells were scored under automated high-content analysis on the Cellomics ArrayScan VTI. For FIGS. 6B, 7B and 8B, MTS substrate was added for two hours then co-culture wells were measured for absorbance at 450 nm using a multi-well plate reader.
Figure 6B:
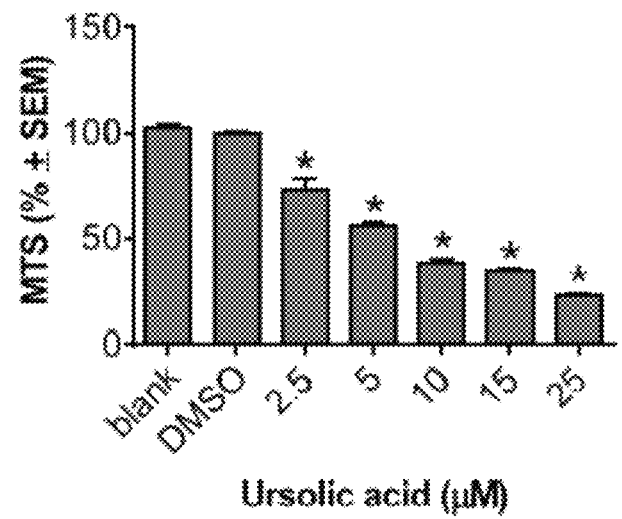
Figure 7A:
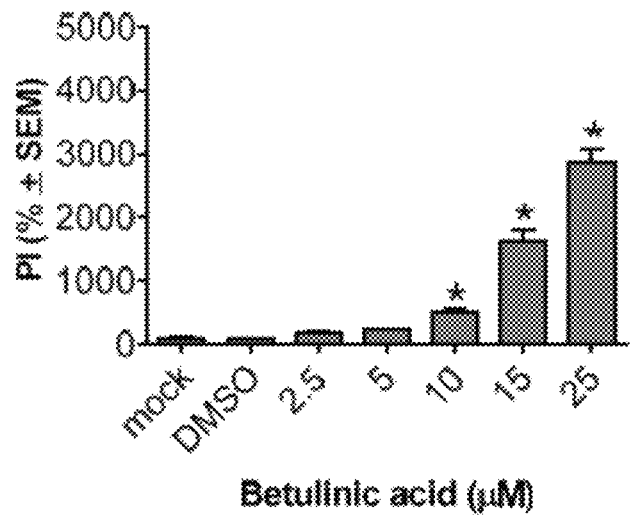
Figure 7B:
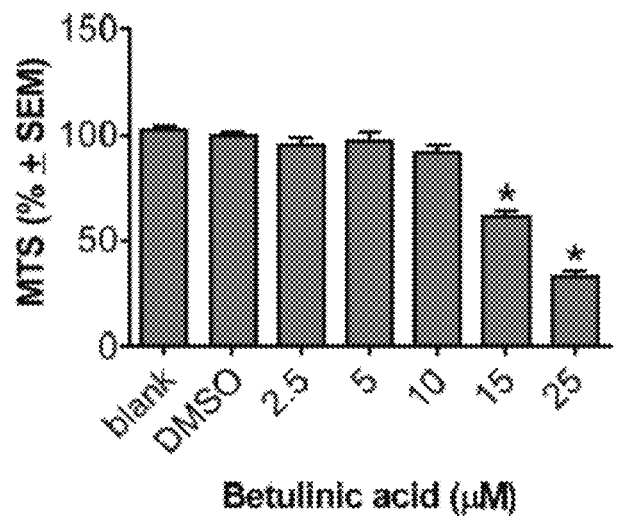
Figure 8A:
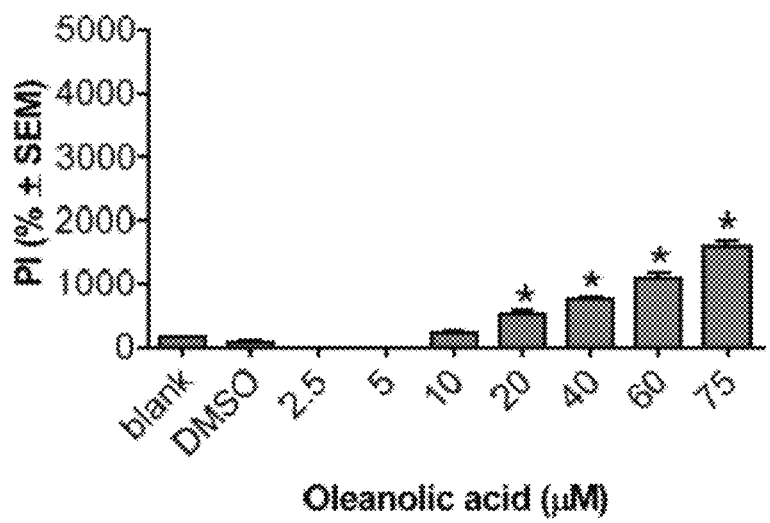
Figure 8B:
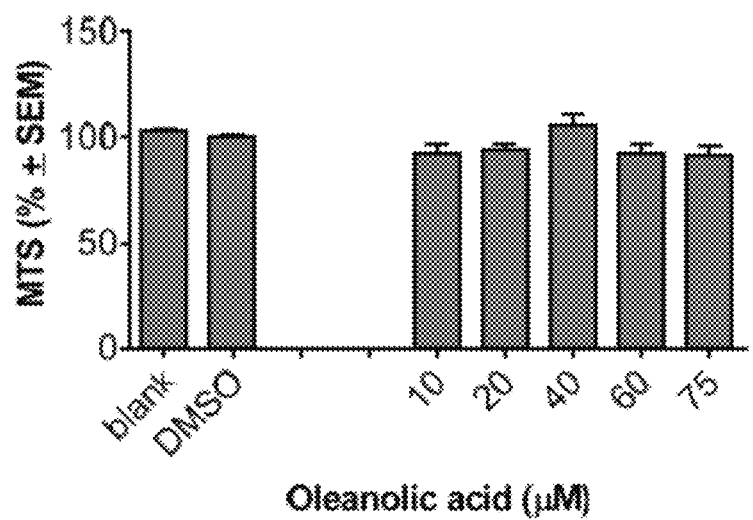

We determined whether the reduced neuroprotective activity of Compositions I and II might be due to cellular toxicity of one or more of the individual triterpenes. We conducted a direct study of the cellular toxicities of oleanolic acid (OA), ursolic acid (UA), and betulinic acid (BA) using two independent measures of cell death: propidium iodide (PI) staining for nuclear breakdown and the MTS assay for cell metabolic activity. PI enters cells with damaged membranes and stains DNA, thereby detecting dead/dying cells using image-based high-content assays on the Cellomics Arrayscan VTI. The MTS assay is a well-based assay in which cleavage of a tetrazolium reporter by mitochondrial enzymes produces colorimetric readout and reports relative numbers of healthy cells. The data (FIGS. 6A and 6B for UA, FIGS. 7A and 7B for BA; FIGS. 8A and 8B for OA) confirmed that UA and BA can be highly toxic compounds on a dose dependent manner, each leading to 50% loss of metabolic activity in the 5-15 μM range, whereas no significant reduction in MTS activity was observed for OA through 75 μM, the highest concentration of OA tested.

Figure 4:
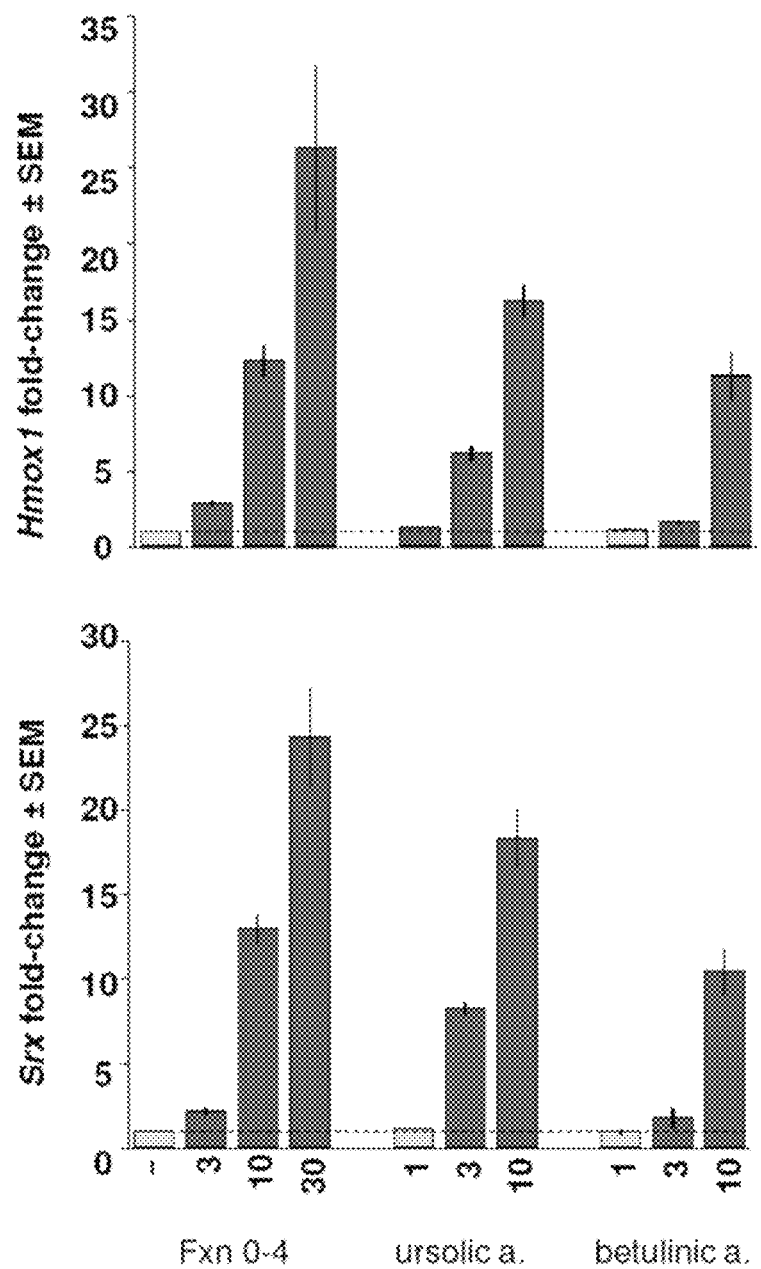
FIG. 4 depicts the results of expression assays for Fraction 0-4 and the individual triterpenes ursolic acid and betulinic acid at more closely-spaced concentration ranges. Rat primary corticostriatal co-cultures were treated for 6 h with Fraction 0-4 (in µg/ml) or ursolic acid and betulinic acid (in µM) at the concentrations indicated, then harvested and processed for qPCR analysis of the ARE target genes shown. Quantitative RNA values were normalized to the GAPDH reference control and fold-expression changes are expressed relative to the DMSO-carrier only condition ("--") set to a value of 1. Dark blue bars denote statistically significant differences with respect to the DMSO-carrier only control by a Student's t-test at $p<0.05$. Betulinic acid, like ursolic acid, is also able to induce clear upregulation of Srx and Hmox1 despite its toxicity at higher concentrations.
Figure 5:
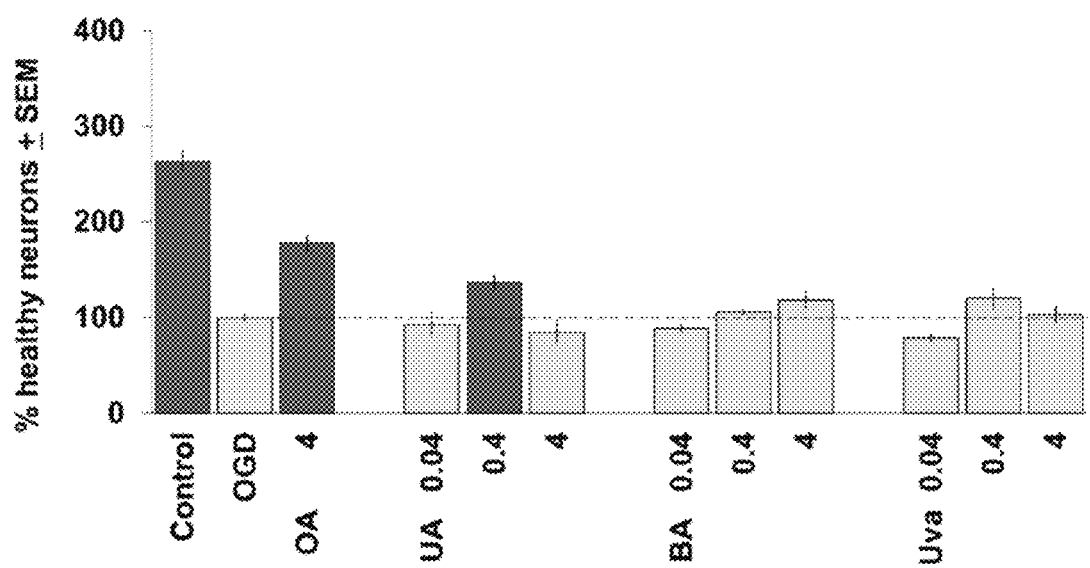
FIG. 5 (prior art: Van Kanegan: vide supra) depicts the results of comparative evaluation in a neuroprotection OGD assay of oleanolic acid (OA), ursolic acid (UA), betulinic acid (BA) and uvaol (Uva). Concentration-response relations for UA, BA, and Uva (all in µg/ml) in the brain slice OGD assay are shown. Averages for 2 independent experiments are included for each compound, with the OGD negative-control condition scaled to 100% and data plotted on the same axes for ease of comparison. The positive control was 4 µg/ml oleanolic acid (0). Note that these are equimolar concentrations for each compound as the molecular weights for all are identical except for uvaol which was tested at 0.039, 0.39, and 3.88 µg/ml rounded to a single significant digit for display purposes. Dark bars denote statistically significant differences with respect to the OGD negative control by ANOVA followed by Dunnett's post hoc comparison test at the 0.05 confidence level.
Figure 10B:
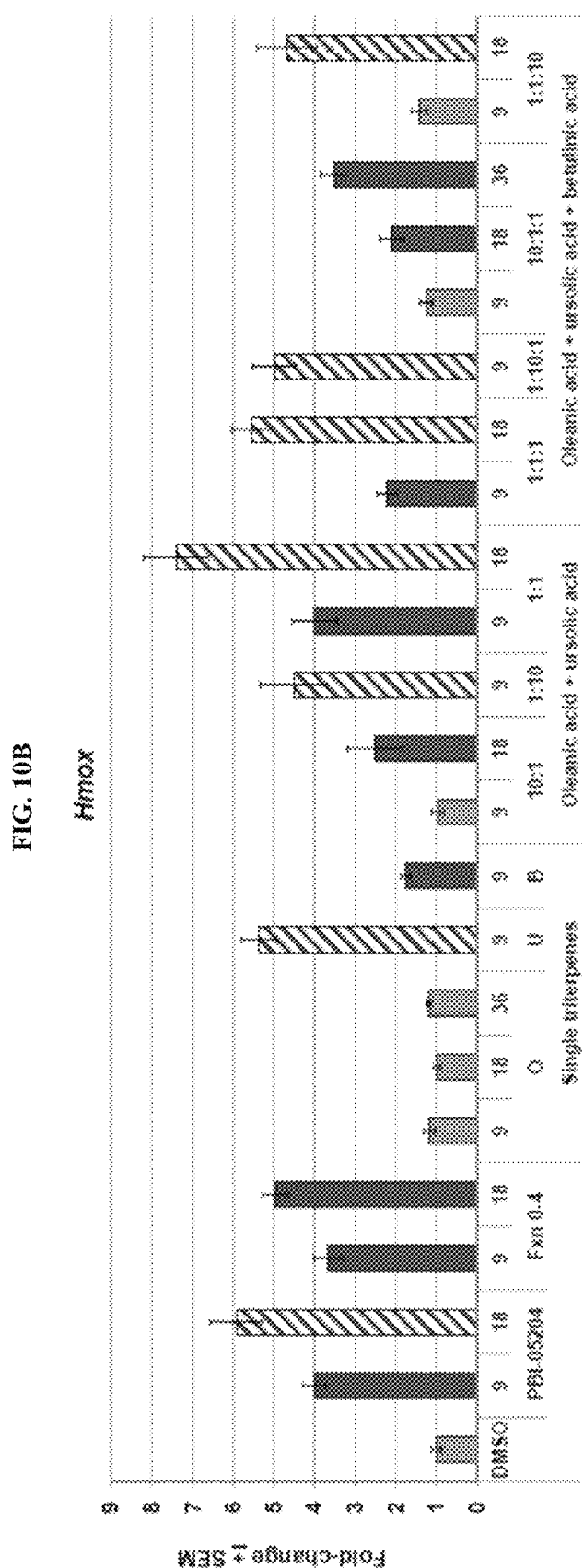

The potential additive and synergistic performance of the mixture of triterpenes was determined by analyzing their performance individually and in different mixtures by way of a gene expression assay. We determined the relative activity of the various compositions to induce ARE gene expression of Hmox1 and Srxn at various different concentrations (μM). Activation of the ARE genes by ursolic acid and betulinic acid was examined using more closely-spaced concentration steps. Betulinic acid, like ursolic acid, is able to induce clear upregulation of Srx and Hmox1 despite its toxicity at higher concentrations (FIG. 4). The data (FIGS. 10A and 10B) indicated that OA as a single agent was not able to induce appreciable ARE gene expression at any concentration tested. Even at low concentration, UA and BA caused cellular toxicity. A number of combinations of OA+UA and OA+UA+BA did induce significant degrees of ARE gene expression, but did so to extents well>10-fold by the highest concentration tested for that condition (striped, red bars for Srxnl). Such excessive induction is associated with longer term cellular toxicity by 24 hours of treatment. This included UA tested as a single agent at 9 μM. Of the mixtures tested, only 10:1:1 OA:UA:BA induced significant induction of ARE genes but to an extent <5-10 fold within the full concentration range tested Thus, the 10:1:1 OA:UA:BA mixture satisfied both criteria for the target profile proposed, namely: 1) that for this ratio no single component would be dose-limiting due to toxicity; and 2) that ARE target genes are significantly induced but by not more than 5- to 10-fold at the highest. Other closely related molar ratios within the ranges described herein also provide substantial neuroprotection without excessive cellular toxicity. Significant induction of the ARE-luciferase reporter is seen in similar concentration ranges that provided neuroprotection in the OGD, APP, and tau brain slice neuroprotection assays.

The results herein were surprising and unexpected. We thus determined that the improved Composition III and other closely related compositions (those having a higher molar content of oleanolic acid and a substantially lower molar content of ursolic acid and betulinic acid) simultaneously provide comparatively reduced cellular toxicity at higher dose and comparatively increased efficacy at very low concentration. This means that on a total-triterpene equimolar basis, the improved composition of the invention provides substantially improved clinical benefit over the individual triterpenes and even over triterpene-based compositions having triterpene molar ratios outside the ranges described herein.

Efficacy of the improved composition of the invention in treating a range of conditions, diseases or disorders can be established by employing known respective prognostic assays (in vitro, in vivo or ex vivo), performing animal studies, and/or performing clinical studies in humans. Examples 16-34 provide exemplary literature methods suitable for establishing the therapeutic efficacy provided by the improved composition of the invention.

During each such evaluation, the individual triterpenes (oleanolic acid, ursolic acid and betulinic acid) are used as control samples to establish baseline activity thereof. Combinations of two or more of the triterpenes are then evaluated. Generalized (molar ratios unspecified) exemplary sample compositions for each assay are set forth in the table below.

| Sample | Triterpene Present (Y/N) | | |
|---|---|---|---|
| | Oleanolic acid (O) | Ursolic acid (U) | Betulinic acid (B) |
| Control 1 | Y | N | N |
| Control 2 | N | Y | N |
| Control 3 | N | N | Y |
| 1 | Y | Y | N |
| 2 | Y | N | Y |
| 3 | Y | Y | Y |
| 4 | N | Y | Y |

Examples 1 and 2 provide detailed exemplary compositions with the molar ratio(s) of the triterpenes as specified therein.

In some embodiments, the composition of the invention comprises at least two triterpenes (free acid, salt(s), derivative(s), and/or prodrug(s) thereof). For example, the invention provides a composition comprising a combination of at least ursolic acid and oleanolic acid or a combination of at least betulinic acid and oleanolic acid, wherein oleanolic acid is present in substantial molar excess over ursolic acid and betulinic acid, respectively.

In some embodiments, the composition of the invention comprises at least three triterpenes (free acid, salt(s), derivative(s), and/or prodrug(s) thereof). In some embodiments, the neuroprotective composition of the invention comprises oleanolic acid, ursolic acid and at least one other triterpene. For example, the composition can further comprise betulinic acid or at least one other triterpene.

The composition can exclude cardiac glycoside, pharmacologically active polysaccharide, and steroid. For example, the neuroprotective composition excludes oleandrin, neriifolin or pharmacologically active polysaccharide obtained from *Nerium* species plant.

When oleanolic acid (O; free acid, salt, derivative, and/or prodrug thereof) and ursolic acid (U; free acid, salt, derivative, and/or prodrug thereof) are present as the primary or sole triterpenes in the composition, the molar ratio of O:U can be varied and can range from about 9-12:about 0.33-5, about 9-12:about 0.4-5, about 9-12:about 0.5-5, about 9-12:about 0.7-5, about 9-12:about 0.9-5, about 9-12:about 1-5, about 9-12:about 0.33-4, about 9-12:about 0.4-4, about 9-12:about 0.5-4, about 9-12:about 0.7-4, about 9-12:about 0.9-4, about 9-12:about 1-4, about 9-12:about 0.33-3, about 9-12:about 0.4-3, about 9-12:about 0.5-3, about 9-12:about 0.7-3, about 9-12:about 0.9-3, about 9-12:about 1-3, about 9-12:about 0.33-2, about 9-12:about 0.4-2, about 9-12:about 0.5-2, about 9-12:about 0.7-2, about 9-12:about 0.9-2, about 9-12:about 1-2, about 10-1:about 1-5, about 10-1:about 1-3, about 9-12:about 0.5-1.5, about 9-11:about 0.5-1.5, about 9.5-10.5:about 0.75-1.25, about 9.5-10.5:about 0.8-1.2, or about 9.75-10.5:about 0.9-1.1.

When oleanolic acid (O; free acid, salt, derivative, and/or prodrug thereof) and betulinic acid (B; free acid, salt, derivative, and/or prodrug thereof) are present as the primary or sole triterpenes in the composition, the molar ratio of O:B can be varied and can range from about 9-12:about 0.33-5, about 9-12:about 0.4-5, about 9-12:about 0.5-5, about 9-12:about 0.7-5, about 9-12:about 0.9-5, about 9-12:about 1-5, about 9-12:about 0.33-4, about 9-12:about 0.4-4, about 9-12:about 0.5-4, about 9-12:about 0.7-4, about 9-12:about 0.9-4, about 9-12:about 1-4, about 9-12:about 0.33-3, about 9-12:about 0.4-3, about 9-12:about 0.5-3, about 9-12:about 0.7-3, about 9-12:about 0.9-3, about 9-12:about 1-3, about 9-12:about 0.33-2, about 9-12:about 0.4-2, about 9-12:about 0.5-2, about 9-12:about 0.7-2, about 9-12:about 0.9-2, about 9-12:about 1-2, about 10-1:about 1-5, about 10-1:about 1-3, about 9-12:about 0.5-1.5, about 9-11:about 0.5-1.5, about 9.5-10.5:about 0.75-1.25, about 9.5-10.5:about 0.8-1.2, or about 9.75-10.5:about 0.9-1.1.

When oleanolic acid (O; free acid, salt, derivative, and/or prodrug thereof), ursolic acid (U; free acid, salt, derivative, and/or prodrug thereof) and betulinic acid (B; free acid, salt, derivative, and/or prodrug thereof) are present as the primary or sole triterpenes in the composition, the molar ratio oleanolic acid:ursolic acid:betulinic acid is about 10:about 1:about 1, about 9-11:about 0.5-1.5:about 0.5-1.5, about 9.5-10.5:about 0.75-1.25:about 0.75-1.25, about 9.5-10.5:about 0.8-1.2:about 0.8-1.2, about 9.75-10.5:about 0.9-1.1:about 0.9-1.1, about 9-12:about 0.15-2.5:about 0.15-2.5, about 9-12:about 0.2-2.5:about 0.2-2.5, about 9-12:about 0.25-2.5:about 0.25-2.5, about 9-12:about 0.35-2.5:about 0.35-2.5, about 9-12:about 0.45-2.5:about 0.45-2.5, about 9-12:about 0.5-5:about 0.5-2.5, about 9-12:about 0.16-2:about 0.16-2, about 9-12:about 0.2-2:about 0.2-2, about 9-12:about 0.25-2:about 0.25-2, about 9-12:about 0.25-2, about 9-12:about 0.45-2:about 0.45-2, about 9-12:about 0.5-2:about 0.5-2, about 9-12:about 0.16-1.5:about 0.16-1.5, about 9-12:about 0.2-1.5:about 0.2-1.5, about 9-12:about 0.25-1.5:about 0.25-1.5, about 9-12:about 0.7-1.5:about 0.35-1.5, about 9-12:about 0.45-1.5:about 0.45-1.5, about 9-12:about 0.5-1.5:about 0.5-1.5, about 9-12:about 0.16-1:about 0.16-1, about 9-12:about 0.2-1:about 0.2-1, about 9-12:about 0.25-1:about 0.25-1, about 9-12:about 0.35-1:about 0.35-1, about 9-12:about 0.45-1:about 0.45-1, about 9-12:about 0.5-1:about 0.5-1, about 10-1:about 0.5-2.5:about 0.5-2.5, about 10-1:about 0.1-1.5:about 0.1-1.5, about 9-12:about 0.25-0.75:about 0.25-0.75, about 9.5-10.5:about 0.35-0.7:about 0.35-0.7, about 9.5-10.5:about 0.4-0.6:about 0.4-0.6, or about 9.75-10.5:about 0.45-0.6:about 0.45-0.6.

Example 11 provides a detailed description of an in vitro assay used to evaluate the efficacy of the neuroprotective composition for the treatment of Alzheimer's disease. The assay is a brain slice-based assay for APP/AP-induced (APP: amyloid precursor protein) degeneration of cortical pyramidal neurons. Upon cleavage by a secretase enzyme, the APP is reduced to AP peptides which are believed to be a causative factor in beta-amyloid plaque formation. AP proteins are associated with beta-amyloid plaque formation and are believed to be a hallmark if not etiologic factor in Alzheimer's disease. Biolistic transfection is used to introduce vital markers such as YFP (a marker yellow fluorescent protein) and to introduce disease gene constructs into the same neuronal populations in the brain slices. YFP is co-transfected with APP isoforms leading to the progressive degeneration of cortical pyramidal neurons over the course of three to four days after brain slice preparation and transfection. The data indicate that the neuroprotective composition provides a concentration-dependent neuroprotection to APP-transfected brain slices. Composition III (O:U:B molar ratio of about 10:1:1 as in PBI-01011) provides greater neuroprotection than Composition II (O:U:B molar ratio of about 7.8:7.4:1 as in PBI-05204) and greater neuroprotection than Composition I (O:U:B molar ratio of about 3:2.2:1 as in PBI-04711). The data are of significance in that few compounds or therapeutic strategies in the literature have shown any significant protection of neurons in this in vitro assay representative of Alzheimer disease.

The composition of the invention also provides strong neuroprotection in two additional brain slice models in which cortical neuronal degeneration is driven by biolistic transfection of expression constructs for genes implicated in CNS neurodegeneration, namely, amyloid precursor protein (APP) and tau. In these models, APP and tau transfection induces progressive neurodegeneration of cortical neurons over the course of 3-4 days, in contrast to the neuronal injury and death caused by OGD which occurs over a 24 h period in the brain slice model.

Data indicate that the composition provides neuroprotection in this assay, even though it does not contain any cardiac glycosides. The neuroprotective composition provides significant concentration-dependent neuroprotection in both the APP and tau brain slice neurodegeneration models.

The composition is evaluated with the tau4R brain slice-based Alzheimer's assay similar to the APP assay except that the Tau construct is used (Example 11). The number of healthy cortical neurons is determined. Efficacy in this assay is defined as or based upon the relative total number of healthy versus unhealthy number and percentage of degraded neurons in the presence of varying amounts of neuroprotective composition. The negative control in these experiments consisted of brain slices that were not exposed to OGD while brain slices exposed to OGD but not treated with neuroprotective composition served as the internal positive control. The neuroprotective composition provides neuroprotection in this assay.

Accordingly, the invention provides a method of protecting neurons against loss of activity caused by Alzheimer's disease, the method comprising: exposing the neurons exhibiting characteristics of Alzheimer's disease to an effective amount of triterpene-based neuroprotective composition to minimize loss of activity, reduce the rate of loss of activity, stop the loss of activity, slow down onset of loss of activity, and/or critical functioning of the neurons caused by Alzheimer's disease. In some embodiments, the method employs an effective amount of neuroprotective composition.

Example 6 provides a detailed description of an assay used to evaluate the efficacy of the neuroprotective composition for the treatment of Huntington's disease. Mutant htt protein is introduced via electroporation into high-density, mixed co-cultures of cortical neurons, striatal neurons, and glia. The striatal and cortical neurons are transfected with different color fluorescent proteins thereby facilitating the separate identification of the different types of neurons in the co-culture. The color fluorescent proteins are fluorescent and 'emit' color upon activation with a light source of appropriate wavelength. The data indicate that the neuroprotective composition can be used to treat Huntington's disease.

Accordingly, the invention provides a method of protecting neurons against loss of activity caused by Huntington's disease, the method comprising: exposing the neurons exhibiting characteristics of Huntington's disease to an effective amount of neuroprotective composition to minimize loss of activity, reduce the rate of loss of activity, stop the loss of activity, slow down onset of loss of activity, and/or normal function of the neurons caused by Huntington's disease.

Examples 3, 4 and 12 detail an exemplary brain-slice assay that can be used to evaluate the efficacy of neuroprotective composition in the treatment of stroke in a subject following completion of a delay period after the stroke. The brain-slice assay with oxygen glucose deprivation is conducted as described herein; however, rather than treating the brain slices prophylactically with the composition, they are treated with the composition after delay periods of 0, 1, 2, 4, and 6 hours. The data should demonstrate that the neuroprotective composition is effective at providing significant neuroprotection for delay periods of up to 1, up to 2, up to 3, up to 4, up to 5, up to about 6 hours after the stroke.

Accordingly, the invention provides a time-delayed method of treating stroke in a subject by administration of a dose of neuroprotective composition to a subject after the subject has suffered a stroke. Within an acceptable delay period after a subject has suffered the stroke, an initial dose of the neuroprotective composition is administered according to an initial dosing regimen. Then, adequacy of the subject's clinical response and/or therapeutic response to treatment with the composition is determined. If the subject's clinical response and/or therapeutic response is adequate, then treatment with the composition is continued as needed until the desired clinical endpoint is achieved. Alternatively, if the subject's clinical response and/or therapeutic response are inadequate at the initial dose and initial dosing regimen, the dose is escalated or deescalated until the desired clinical response and/or therapeutic response in the subject is achieved. Dose escalation or de-escalation can be performed in conjunction with a change in the dosing regimen, such as a change in dosing frequency or overall period of dose administration.

Some of the brain slice assays herein are conducted under conditions wherein the brain tissue is treated with the neuroprotective composition prior to OGD. Under those conditions, the data establishes the utility of the neuroprotective composition at prophylactically providing neuroprotection against damage caused by stroke.

The inventors have discovered that the composition of the invention provides neuroprotection mediated through antioxidant transcriptional response elements (AREs) with triterpene(s). The triterpene(s) also induces nuclear factor erythroid 2 related factor 2 (Nrf2)-dependent antioxidant genes to provide neuroprotection. When the neuroprotective composition is administered to a subject in need thereof, the composition provides neuroprotection via at least a two-fold mechanism. When the neuroprotective composition is administered to a subject in need thereof, the composition provides neuroprotection at least through ARE up-regulation.

If a clinician intends to treat a subject having a neurological condition with a combination of triterpene-based composition and one or more other therapeutic agents, and it is known that the particular condition, disease or disorder, which the subject has, is at least partially therapeutically responsive to treatment with said one or more other therapeutic agents, then the present method invention comprises: administering to the subject in need thereof a therapeutically relevant dose of triterpene-based composition and a therapeutically relevant dose of said one or more other therapeutic agents, wherein the triterpene-based composition is administered according to a first dosing regimen and the one or more other therapeutic agents is administered according to a second dosing regimen. In some embodiments, the first and second dosing regimens are the same. In some embodiments, the first and second dosing regimens are different.

If the neurological condition being treated is Alzheimer's disease, the one or more other therapeutic agents can be selected from the group consisting of BACE inhibitors or acetylcholinesterase inhibitors. In some embodiments, the one or more other therapeutic agents can be selected from the group consisting of Namenda™ (memantine HCl), Aricept™ (donepezil), Razadyne™ (galantamine), Exelon™ (rivastigmine), and Cognex™ (tacrine).

If the neurological condition being treated is Huntington's disease, the one or more other therapeutic agents can be selected from the group consisting of natural products, anticonvulsants, NMDA (n-methyl d-aspartate) receptor antagonists, and sodium channel blockers. Exemplary agents include Vitamin E, Baclofen (a derivative of CoQ10), Lamotrigine (an anticonvulsant), remacemide (an anesthetic which is a low affinity NMDA antagonist), and riluzole (Na channel blocker). The efficacy of each of these agents is considered to be low (Mestre T. et al, Chochrane Database Systematic Reviews Jul. 8, 2009; 8(3): CD006455) on its own; however, it is expected that administration of a dosage form containing neuroprotective composition to subjects receiving one or more of these other agents will provide a subject, having a neurological disorder, an improved clinical affect as compared to administration of these agents absent the neuroprotective composition.

If the neurological condition being treated is stroke-mediated ischemic brain injury (ischemic stroke), then the therapeutic treatments disclosed in the literature (Gutierrez M. et al. "Cerebral protection, brain repair, plasticity and cell therapy in ischemic stroke" *Cerebrovasc. Dis.* 2009; 27 Suppl 1:177-186), e.g. intravenous thrombolysis, can be employed in addition to the neuroprotective composition. In some embodiments, the one or more other therapeutic agents can be selected from the group consisting of drugs such as Alteplase (a thrombolytic agent).

If the neurological condition being treated is Parkinson's disease, the one or more other therapeutic agents include a combination of carbidopa and levodopa, rasagiline, pramipexole, ropinrole, amantadine, memantine, entacapone, rotigotine, benztropine, selegiline, biperiden, a combination of carbidopa and levodopa and entacapone, trihexyphenidyl, rivastigmine, apomorphine, levodopa, carbidopa, bromocriptine, *belladonna*, tolcapone, or a combination thereof.

The one or more other therapeutic agents can be selected from the group consisting of BACE (beta-secretase 1; beta-site amyloid precursor protein cleaving enzyme 1, beta-site APP cleaving enzyme 1, membrane-associated aspartic protease 2, memapsin-2, aspartyl protease 2, and ASP2) inhibitors, AZD3293, acetylcholinesterase inhibitors, Namenda™ (memantine HCl), Aricept™ (donepezil), Razadyne™ (galantamine), Exelon™ (rivastigmine), Cognex™ (tacrine), anticonvulsants, NMDA (n-methyl d-aspartate) receptor antagonists, sodium channel blockers Vitamin E, Baclofen (a derivative of CoQ10), Lamotrigine (an anticonvulsant), remacemide (an anesthetic which is a low affinity NMDA antagonist), riluzole (Na channel blocker), Alteplase (a thrombolytic agent), levodopa, carbidopa, amantadine, COMT (catechol O-methyl transferase) inhibitor, tolcapone, entacapone, opicapone, dopamine agonist, bromocriptine, pergolide, pramipexole, ropinirole, piribedil, cabergoline, apomorphine, lisuride, MAO-B (monoamine oxidase-B) inhibitor (selective and non-selective MAO-B inhibitors), anticholinergic, cholinesterase inhibitor, isocarboxazid, nialamide, phenelzine, hydracarbazine, rasagiline, selegiline, linezolid, or a combination thereof.

Compounds or combinations of compounds suitable for cotherapy or adjunctive use with the triterpene-based composition are disclosed by Drugs.com (https://www.drugs.com/drug-classes.html) and are readily identifiable by conducting drug class searches or specific compound searches. For example, a search for suitable antiviral compounds in the Drugs.com database resulted in identification of adamantane-based antiviral agent, interferon-based antiviral agent, chemokine receptor antagonist, integrase strand transfer inhibitor, neuraminidase inhibitor, non-nucleoside reverse transcriptase inhibitor, NS5A inhibitor, nucleoside reverse transcriptase inhibitor, protease inhibitor, purine nucleoside, or a combination thereof. One or more of those antiviral compounds can be coadministered or used as cotherapy or used adjunctively with the triterpene-based composition.

Additionally, the one or more other therapeutic agents that are approved for human use are listed, searchable and viewable in the databases of the U.S. Food and Drug Administration (U.S.F.D.A.), World Health Organization (W.H.O), European Medicines Agency (E.M.E.A.), Therapeutic Goods Administration (TGA, Australia), Pan American Health Organization (PAHO), Medicines and Medical Devices Safety Authority (Medsafe, New Zealand) or the various Ministries of Health worldwide, the entire disclosures of which are hereby incorporated by reference.

The one or more other therapeutic agents can be administered at doses and according to dosing regimens that are clinician-recognized as being therapeutically effective or at doses that are clinician-recognized as being sub-therapeutically effective. The clinical benefit and/or therapeutic effect provided by administration of a combination of the triterpene-based composition and one or more other therapeutic can be additive or synergistic, such level of benefit or effect being determined by comparison of administration of the combination to administration of the individual triterpene-based composition and one or more other therapeutic agents. The one or more other therapeutic agents can be administered at doses and according to dosing regimens as suggested or described by the U.S. Food and Drug Administration (U.S.F.D.A.), World Health Organization (W.H.O), European Medicines Agency (E.M.E.A.), Therapeutic Goods Administration (TGA, Australia), Pan American Health Organization (PAHO), Medicines and Medical Devices Safety Authority (Medsafe, New Zealand) or the various Ministries of Health worldwide.

A triterpene-based composition of the invention can be prepared by mixing the individual components thereof into a mixture (Examples 1-2). For example, the triterpene-based composition can be prepared by mixing at least oleanolic acid and ursolic acid, and optionally betulinic acid, according to the molar ratios described herein. Alternatively, the triterpene-based composition can be prepared by mixing at least oleanolic acid and betulinic acid, and optionally ursolic acid, according to the molar ratios described herein. The triterpene-based composition can also be prepared by mixing at least oleanolic acid, ursolic acid, and betulinic acid, according to the molar ratios described herein.

We have determined that triterpenes exhibit different levels of activity in the neuroprotection OGD assay described herein. Accordingly, the level of contribution of the individual triterpenes toward efficacy and cellular toxicity of a neuroprotective composition containing them. We have discovered that the molar ratio of the triterpenes in the triterpene-based neuroprotective composition must be correctly balanced in order to provide the greatest level of neuroprotective efficacy while maintaining reduced level of cellular toxicity.

The lower activity of UA in the neuroprotection OGD assay is surprising. Data obtained from the expression assays demonstrate that Fraction 0-4 induces substantial expression of Nrf2, Srx and Hmox1 and lower expression of Gclc and Nqo1; however, data also demonstrate that the induction of Srx and Hmox1 is due more so to the activity of UA than of OA or BA. The efficacy (especially the broad dose response curve and high level of efficacy at low concentrations) of the composition comprising plural triterpenes is apparently due to various mechanisms operating synergistically to provide neuroprotection.

We have discovered that the level of efficacy provided by the compositions of the invention can be improved by employing compositions possessing suitable molar ratios of O:U or of O:U:B or of O:B. Solutions containing the following molar ratios of triterpene(s) were prepared (Examples 1-2) and evaluated for neuroprotective activity and ARE gene induction activity as described herein.

In some embodiments, an improved triterpene-based composition comprises at least oleanolic acid (free acid, salt(s) thereof, derivative(s) thereof, and/or prodrug(s) thereof) and ursolic acid (free acid, salt(s) thereof, derivative(s) thereof, and/or prodrug(s) thereof) present at a molar ratio of OA to UA as described herein, wherein OA is present in large molar excess over UA.

In some embodiments, an improved triterpene-based composition comprises at least oleanolic acid (free acid, salt(s) thereof, derivative(s) thereof, and/or prodrug(s) thereof) and betulinic acid (free acid, salt(s) thereof, derivative(s) thereof, and/or prodrug(s) thereof) present at a molar ratio of OA to BA as described herein, wherein OA is present in large molar excess over BA.

In some embodiments, an improved triterpene-based composition comprises at least oleanolic acid (free acid, salt(s) thereof, derivative(s) thereof, and/or prodrug(s) thereof), ursolic acid (free acid, salt(s) thereof, derivative(s) thereof, and/or prodrug(s) thereof), and betulinic acid (free acid, salt(s) thereof, derivative(s) thereof, and/or prodrug(s) thereof) present at a molar ratio of OA to UA to BA as described herein, wherein OA is present in large molar excess over both UA and BA.

An improved triterpene-based composition provides a wider dose response curve than the respective triterpenes individually and provides reduced cellular toxicity when compared on a total equimolar basis, especially when compared at the higher end of the dosing range.

The triterpene-based composition can be formulated in any suitable pharmaceutically acceptable dosage form. Parenteral, otic, ophthalmic, nasal, inhalable, buccal, sublingual, enteral, topical, oral, peroral, and injectable dosage forms are particularly useful. Particular dosage forms include a solid or liquid dosage forms. Exemplary suitable dosage forms include tablet, capsule, osmotic device, pill, caplet, troche, sache, solution, suspension, dispersion, vial, bag, bottle, injectable liquid, i.v. (intravenous), i.m. (intramuscular) or i.p. (intraperitoneal) administrable liquid and other such dosage forms known to the artisan of ordinary skill in the pharmaceutical sciences.

Suitable dosage forms containing the triterpene-based composition can be prepared by mixing the said composition with pharmaceutically acceptable excipients as described herein or as described in Pi et al. ("Ursolic acid nanocrystals for dissolution rate and bioavailability enhancement: influence of different particle size" in Curr. Drug Deliv. (March 2016), 13(8), 1358-1366), Yang et al. ("Self-microemulsifying drug delivery system for improved oral bioavailability of oleanolic acid: design and evaluation" in Int. J. Nanomed. (2013), 8(1), 2917-2926), Li et al. (Development and evaluation of optimized sucrose ester stabilized oleanolic acid nanosuspensions prepared by wet ball milling with design of experiments" in Biol. Pharm. Bull. (2014), 37(6), 926-937), Zhang et al. ("Enhancement of oral bioavailability of triterpene through lipid nanospheres: preparation, characterization, and absorption evaluation" in J. Pharm. Sci. (June 2014), 103(6), 1711-1719), Godugu et al. ("Approaches to improve the oral bioavailability and effects of novel anticancer drugs berberine and betulinic acid" in PLoS One (March 2014), 9(3):e89919), Zhao et al. ("Preparation and characterization of betulin nanoparticles for oral hypoglycemic drug by antisolvent precipitation" in Drug Deliv. (September 2014), 21(6), 467-479), Yang et al. ("Physicochemical properties and oral bioavailability of ursolic acid nanoparticles using supercritical anti-solvent (SAS) process" in Food Chem. (May 2012), 132(1), 319-325), Cao et al. ("Ethylene glycol-linked amino acid diester prodrugs of oleanolic acid for PEPT1-mediated transport: synthesis, intestinal permeability and pharmacokinetics" in Mol. Pharm. (August 2012), 9(8), 2127-2135), Li et al. ("Formulation, biological and pharmacokinetic studies of sucrose ester-stabilized nanosuspensions of oleanolic acid" in Pharm. Res. (August 2011), 28(8), 2020-2033), Tong et al. ("Spray freeze drying with polyvinylpyrrolidone and sodium caprate for improved dissolution and oral bioavailablity of oleanolic acid, a BCS Class IV compound" in Int. J. Pharm. (February 2011), 404(1-2), 148-158), Xi et al. (Formulation development and bioavailability evaluation of a self-nanoemulsified drug delivery system of oleanolic acid" in AAPS PharmSciTech (2009), 10(1), 172-182), Chen et al. ("Oleanolic acid nanosuspensions: preparation, in-vitro characterization and enhanced hepatoprotective effect" in J. Pharm. Pharmacol. (February 2005), 57(2), 259-264), the entire disclosures of which are hereby incorporated by reference.

Suitable dosage forms can also be made according to U.S. Pat. No. 8,187,644 B2 to Addington, which issued May 29, 2012, U.S. Pat. No. 7,402,325 B2 to Addington, which issued Jul. 22, 2008, U.S. Pat. No. 8,394,434 B2 to Addington et al, which issued Mar. 12, 2013, the entire disclosures of which are hereby incorporated by reference. Suitable dosage forms can also be made as described in Examples 13-15.

The desired dose for oral administration is up to 5 dosage forms although as few as one and as many as ten dosage forms may be administered as a single dose. Exemplary dosage forms contain 0.01-5 or 0.01-10 mg of the triterpene-based composition per dosage form, for a total 0.1 to 500 mg (1 to 10 dose levels) per dose. Doses will be administered according to dosing regimens that may be predetermined and/or tailored to achieve specific therapeutic response or clinical benefit in a subject.

Some embodiments of the dosage form are not enteric coated and release their charge of triterpene-based composition within a period of 0.5 to 1 hours or less. Some embodiments of the dosage form are enteric coated and release their charge of triterpene-based composition downstream of the stomach, such as from the jejunum, ileum, small intestine, and/or large intestine (colon). Enterically coated dosage forms will release said composition into the systemic circulation within 1-10 hr after oral administration.

The triterpene-based composition can be included in a rapid release, immediate release, controlled release, sustained release, prolonged release, extended release, burst release, continuous release, slow release, or pulsed release dosage form or in a dosage form that exhibits two or more of those types of release. The release profile of triterpene from the dosage form can be a zero order, pseudo-zero, first order, pseudo-first order or sigmoidal release profile. The plasma concentration profile for triterpene in a subject to which the neuroprotective composition is administered can exhibit one or more maxima.

The amount of triterpene-based composition incorporated in a dose will be in at least one or more dosage forms and can be selected according to known principles of pharmacy. An effective amount or therapeutically relevant amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of active ingredient which is enough for the required or desired therapeutic response, or in other words, the amount, which is sufficient to elicit an appreciable biological response when, administered to a patient. The appreciable biological response may occur as a result of administration of single or multiple doses of an active substance. A dose may comprise one or more dosage forms. It will be understood that the specific dose level for any patient will depend upon a variety of factors including the indication being treated, severity of the indication, patient health, age, gender, weight, diet, pharmacological response, the specific dosage form employed, and other such factors.

The triterpene-based composition can be administered at low to high dose due to the improved combination of triterpenes present and the molar ratio at which they are present. A therapeutically effective dose for humans is approximately 100-1000 mg of triterpene-based composition per Kg of body weight. Such a dose can be administered up to 10 times in a 24-hour period.

It should be noted that a compound herein might possess one or more functions in the formulation of the invention. For example, a compound might serve as both a surfactant and a water miscible solvent or as both a surfactant and a water immiscible solvent.

A liquid composition can comprise one or more pharmaceutically acceptable liquid carriers. The liquid carrier can be an aqueous, non-aqueous, polar, non-polar, and/or organic carrier. Liquid carriers include, by way of example and without limitation, a water miscible solvent, water immiscible solvent, water, buffer and mixtures thereof.

As used herein, the terms "water soluble solvent" or "water miscible solvent", which terms are used interchangeably, refer to an organic liquid which does not form a biphasic mixture with water or is sufficiently soluble in water to provide an aqueous solvent mixture containing at least five percent of solvent without separation of liquid phases. The solvent is suitable for administration to humans or animals. Exemplary water soluble solvents include, by way of example and without limitation, PEG (poly(ethylene glycol)), PEG 400 (poly(ethylene glycol having an approximate molecular weight of about 400), ethanol, acetone, alkanol, alcohol, ether, propylene glycol, glycerin, triacetin, poly(propylene glycol), PVP (poly(vinyl pyrrolidone)), dimethylsulfoxide, N,N-dimethylformamide, formamide, N,N-dimethylacetamide, pyridine, propanol, N-methylacetamide, butanol, soluphor (2-pyrrolidone), pharmasolve (N-methyl-2-pyrrolidone).

As used herein, the terms "water insoluble solvent" or "water immiscible solvent", which terms are used interchangeably, refer to an organic liquid which forms a biphasic mixture with water or provides a phase separation when the concentration of solvent in water exceeds five percent. The solvent is suitable for administration to humans or animals. Exemplary water insoluble solvents include, by way of example and without limitation, medium/long chain triglycerides, oil, castor oil, corn oil, vitamin E, vitamin E derivative, oleic acid, fatty acid, olive oil, softisan 645 (Diglyceryl Caprylate/Caprate/Stearate/Hydroxy stearate adipate), miglyol, captex (Captex 350: Glyceryl Tricaprylate/Caprate/Laurate triglyceride; Captex 355: Glyceryl Tricaprylate/Caprate triglyceride; Captex 355 EP/NF: Glyceryl Tricaprylate/Caprate medium chain triglyceride).

Suitable solvents are listed in the "International Conference on Harmonisation of Technical Requirements for Registration of Pharmaceuticals for Human Use (ICH) guidance for industry *Q3C Impurities: Residual Solvents*" (1997), which makes recommendations as to what amounts of residual solvents are considered safe in pharmaceuticals. Exemplary solvents are listed as class 2 or class 3 solvents. Class 3 solvents include, for example, acetic acid, acetone, anisole, 1-butanol, 2-butanol, butyl acetate, tert-butlymethyl ether, cumene, ethanol, ethyl ether, ethyl acetate, ethyl formate, formic acid, heptane, isobutyl acetate, isopropyl acetate, methyl acetate, methyl-1-butanol, methylethyl ketone, methylisobutyl ketone, 2-methyl-1-propanol, pentane, 1-pentanol, 1-propanol, 2-propanol, or propyl acetate.

Other materials that can be used as water immiscible solvents in the invention include: Captex 100: Propylene Glycol Dicaprate; Captex 200: Propylene Glycol Dicaprylate/Dicaprate; Captex 200 P: Propylene Glycol Dicaprylate/Dicaprate; Propylene Glycol Dicaprylocaprate; Captex 300: Glyceryl Tricaprylate/Caprate; Captex 300 EP/NF: Glyceryl Tricaprylate/Caprate Medium Chain Triglycerides; Captex 350: Glyceryl Tricaprylate/Caprate/Laurate; Captex 355: Glyceryl Tricaprylate/Caprate; Captex 355 EP/NF: Glyceryl Tricaprylate/Caprate Medium Chain Triglycerides; Captex 500: Triacetin; Captex 500 P: Triacetin (Pharmaceutical Grade); Captex 800: Propylene Glycol Di (2-Ethythexanoate); Captex 810 D: Glyceryl Tricaprylate/Caprate/Linoleate; Captex 1000: Glyceryl Tricaprate; Captex CA: Medium Chain Triglycerides; Captex MCT-170: Medium Chain Triglycerides; Capmul GMO: Glyceryl Monooleate; Capmul GMO-50 EP/NF: Glyceryl Monooleate; Capmul MCM: Medium Chain Mono-& Diglycerides; Capmul MCM C8: Glyceryl Monocaprylate; Capmul MCM C10: Glyceryl Monocaprate; Capmul PG-8: Propylene Glycol Monocaprylate; Capmul PG-12: Propylene Glycol Monolaurate; Caprol 10G10O: Decaglycerol Decaoleate; Caprol 3GO: Triglycerol Monooleate; Caprol ET: Polyglycerol Ester of Mixed Fatty Acids; Caprol MPGO: Hexaglycerol Dioleate; Caprol PGE 860: Decaglycerol Mono-, Dioleate.

As used herein, a "surfactant" refers to a compound that comprises polar or charged hydrophilic moieties as well as non-polar hydrophobic (lipophilic) moieties; i.e., a surfactant is amphiphilic. The term surfactant may refer to one or a mixture of compounds. A surfactant can be a solubilizing agent, an emulsifying agent or a dispersing agent. A surfactant can be hydrophilic or hydrophobic.

The hydrophilic surfactant can be any hydrophilic surfactant suitable for use in pharmaceutical compositions. Such surfactants can be anionic, cationic, zwitterionic or non-ionic, although non-ionic hydrophilic surfactants are presently preferred. As discussed above, these non-ionic hydrophilic surfactants will generally have HLB values greater than about 10. Mixtures of hydrophilic surfactants are also within the scope of the invention.

Similarly, the hydrophobic surfactant can be any hydrophobic surfactant suitable for use in pharmaceutical compositions. In general, suitable hydrophobic surfactants will have an HLB value less than about 10. Mixtures of hydrophobic surfactants are also within the scope of the invention.

Examples of additional suitable solubilizer include: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide); amides, such as 2-pyrrolidone, 2-piperidone, caprolactam, N-alkylpyrrolidone, N-hydroxyalkylpyrrolidone, N-alkylpiperidone, N-alkylcaprolactam, dimethylacetamide, and polyvinypyrrolidone; esters, such as ethyl propionate, tributylcitrate,acetyl triethylcitrate, acetyl tributyl citrate, triethylcitrate, ethyl oleate, ethyl caprylate, ethyl butyrate, triacetin, propylene glycol monoacetate, propylene glycol diacetate, caprolactone and isomers thereof, valerolactone and isomers thereof, butyrolactone and isomers thereof and other solubilizers known in the art, such as dimethyl acetamide, dimethyl isosorbide (Arlasolve DMI (ICI)), N-methyl pyrrolidones (Pharmasolve (ISP)), monooctanoin, diethylene glycol nonoethyl ether (available from Gattefosse under the trade name Transcutol), and water. Mixtures of solubilizers are also within the scope of the invention.

Except as indicated, compounds mentioned herein are readily available from standard commercial sources.

The clear liquid composition is visually clear to the unaided eye, as it will contain less than 5%, less than 3% or less than 1% by wt. of suspended solids based upon the total weight of the composition.

Although not necessary, a composition or kit of the present invention may include a chelating agent, preservative, antioxidant, adsorbents, acidifying agent, alkalizing agent, antifoaming agent, buffering agent, colorant, electrolyte, salt, stabilizer, tonicity modifier, diluent, other pharmaceutical excipient, or a combination thereof.

As used herein, the term "antioxidant" is intended to mean an agent that inhibits oxidation and is thus used to prevent the deterioration of preparations by the oxidative process. Such compounds include, by way of example and without limitation, ascorbic acid, ascorbic palmitate, Vitamin E, Vitamin E derivative, butylated hydroxyanisole, butylated hydroxytoluene, hypophosphorous acid, monothioglycerol, propyl gallate, sodium ascorbate, sodium bisulfite, sodium formaldehyde sulfoxylate, sodium metalbisulfite and other such materials known to those of ordinary skill in the art.

As used herein, the term chelating agent is intended to mean a compound that chelates metal ions in solution. Exemplary chelating agents include EDTA (tetrasodium ethylenediaminetetraacetate), DTPA (pentasodium diethylenetriaminepentaacetate), HEDTA (trisodium salt of N-(hydroxyethyl)-ethylene-diaminetriacetic acid), NTA (trisodium nitrilotriacetate), disodium ethanoldiglycine ($Na_2EDG$), sodium diethanolglycine (DEGNa), citric acid, and other compounds known to those of ordinary skill in the art.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "alkalizing agent" is intended to mean a compound used to provide an alkaline medium. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "acidifying agent" is intended to mean a compound used to provide an acidic medium. Such compounds include, by way of example and without limitation, acetic acid, amino acid, citric acid, fumaric acid and other alpha-hydroxy acids, hydrochloric acid, ascorbic acid, and nitric acid and others known to those of ordinary skill in the art.

As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE, octoxynol and others known to those of ordinary skill in the art.

As used herein, the term "buffering agent" is intended to mean a compound used to resist a change in pH upon dilution or addition of acid or alkali. Such compounds include, by way of example and without limitation, potassium metaphosphate, potassium phosphate, monobasic sodium acetate and sodium citrate anhydrous and dehydrate and other such materials known to those of ordinary skill in the art.

As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "preservative" is intended to mean a compound used to prevent the growth of microorganisms. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl, or butyl parabens and others known to those of ordinary skill in the art.

As used herein, the term "colorant" is intended to mean a compound used to impart color to pharmaceutical preparations. Such compounds include, by way of example and without limitation, FD&C Red No. 3, FD&C Red No. 20, FD&C Yellow No. 6, FD&C Blue No. 2, FD&C Green No. 5, FD&C Orange No. 5, FD&C Red No. 8, caramel, and iron oxide (black, red, yellow), other FD&C dyes and natural coloring agents such as grape skin extract, beet red powder, beta-carotene, annato, carmine, turmeric, paprika, combinations thereof and other such materials known to those of ordinary skill in the art.

As used herein, the term "stabilizer" is intended to mean a compound used to stabilize an active agent against physical, chemical, or biochemical processes that would otherwise reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those or ordinary skill in the art.

The composition of the invention can also include oils such as fixed oils, peanut oil, sesame oil, cottonseed oil, corn oil and olive oil; fatty acids such as oleic acid, stearic acid and isostearic acid; and fatty acid esters such as ethyl oleate, isopropyl myristate, fatty acid glycerides and acetylated fatty acid glycerides. The composition can also include alcohol such as ethanol, isopropanol, hexadecyl alcohol, glycerol and propylene glycol; glycerol ketals such as 2,2-dimethyl-1,3-dioxolane-4-methanol; ethers such as poly (ethylene glycol) 450; petroleum hydrocarbons such as mineral oil and petrolatum; water; a pharmaceutically suitable surfactant, suspending agent or emulsifying agent; or mixtures thereof.

It should be understood that the compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

One or more of the components of the formulation can be present in its free base or pharmaceutically or analytically acceptable salt form. As used herein, "pharmaceutically or analytically acceptable salt" refers to a compound that has been modified by reacting it with an acid or base as needed to form an ionically bound pair. Examples of acceptable salts include conventional non-toxic salts formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Lists of other suitable salts are found in *Remington's Pharmaceutical Sciences,* 17$^{th}$. ed., Mack Publishing Company, Easton, Pa., 1985, p. 1418, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

A dosage form can be made by any conventional means known in the pharmaceutical industry. A liquid dosage form can be prepared by providing at least one liquid carrier and said improved composition in a container. One or more other excipients can be included in the liquid dosage form. A solid dosage form can be prepared by providing at least one solid carrier and said improved composition. One or more other excipients can be included in the solid dosage form.

A dosage form can be packaged using conventional packaging equipment and materials. It can be included in a pack, bottle, via, bag, syringe, envelope, packet, blister pack, box, ampoule, or other such container.

The invention includes a method for improving the clinical status of a statistically significant number of subjects of in a population of subjects having a neurological condition, the method comprising: administering to the population of subjects a neuroprotective composition; and determining the clinical status of the subjects to establish the improved clinical status. In some embodiments, the statistically significant number is at least 5%, at least 10%, at least 20%, at least 30%, at least 40%, at least 50%, at least 60%, at least 70%, at least 80% or at least 90% of the population. In some embodiments, the neuroprotective composition comprises one or more other pharmacologically active compounds.

As used herein a "derivative" is: a) a chemical substance that is related structurally to a first chemical substance and theoretically derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps. For example, a derivative may include a deuterated form, oxidized form, dehydrated, unsaturated, polymer conjugated or glycosilated form thereof or may include an ester, amide, lactone, homolog, ether, thioether, cyano, amino, alkylamino, sulfhydryl, heterocyclic, heterocyclic ring-fused, polymerized, pegylated, benzylidenyl, triazolyl, piperazinyl or deuterated form thereof.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

The triterpenes can be purchased from Sigma Chemical Co. (St. Louis, Mo.).

Example 1

Preparation of Triterpene Mixtures

The following compositions were made by mixing the specified triterpenes in the approximate molar ratios indicated. No specific order of mixing is required. The triterpenes can be mixed in any form in the presence or absence of liquid.

| Composition | Triterpene (Approximate Relative Molar Content) | | |
|---|---|---|---|
| | Oleanolic acid (O) | Ursolic acid (U) | Betulinic acid (B) |
| I (A-C) | 3 | 2.2 | 1 |
| II (A-C) | 7.8 | 7.4 | 1 |
| III (A-C) | 10 | 1 | 1 |
| IV (A-C) | 1 | 10 | 1 |
| V (A-C) | 1 | 1 | 10 |
| VI (A-C) | 1 | 1 | 0 |
| VII (A-C) | 1 | 1 | 1 |
| VIII (A-C) | 10 | 1 | 0 |
| IX (A-C) | 1 | 10 | 0 |

For each composition, three different respective solutions were made, whereby the total concentration of triterpenes in each solution was approximately 9 µM, 18 µM, or 36 µM.

| Composition (total triterpene content, µM) | Triterpene (Approximate Content of Each, µM) | | |
|---|---|---|---|
| | Oleanolic acid (O) | Ursolic acid (U) | Betulinic acid (B) |
| I-A (36) | 17.4 | 12.8 | 5.8 |
| I-B (18) | 8.7 | 6.4 | 2.9 |
| I-C (9) | 4.4 | 3.2 | 1.5 |
| II-A (36) | 17.3 | 16.4 | 2.2 |
| II-B (18) | 8.7 | 8.2 | 1.1 |
| II-C (9) | 4.3 | 4.1 | 0.6 |
| III-A (36) | 30 | 3 | 3 |
| III-B (18) | 15 | 1.5 | 1.5 |
| III-C (9) | 7.5 | 0.75 | 0.75 |
| IV-A (36) | 3 | 30 | 3 |
| IV-B (18) | 1.5 | 15 | 1.5 |
| IV-C (9) | 0.75 | 7.5 | 0.75 |
| V-A (36) | 3 | 3 | 30 |
| V-B (18) | 1.5 | 1.5 | 15 |
| V-C (9) | 0.75 | 0.75 | 7.5 |
| VI-A (36) | 18 | 18 | 0 |
| VI-B (18) | 9 | 9 | 0 |
| VI-C (9) | 4.5 | 4.5 | 0 |

-continued

| Composition (total triterpene content, μM) | Triterpene (Approximate Content of Each, μM) | | |
|---|---|---|---|
| | Oleanolic acid (O) | Ursolic acid (U) | Betulinic acid (B) |
| VII-A (36) | 12 | 12 | 12 |
| VII-B (18) | 6 | 6 | 6 |
| VII-C (9) | 3 | 3 | 3 |
| VIII-A (36) | 32.7 | 3.3 | 0 |
| VIII-B (18) | 16.35 | 1.65 | 0 |
| VIII-C (9) | 8.2 | 0.8 | 0 |
| IX-A (36) | 3.3 | 32.7 | 0 |
| IX-B (18) | 1.65 | 16.35 | 0 |
| IX-C (9) | 0.8 | 8.2 | 0 |

Example 2

Preparation of Improved Pharmaceutical Compositions

Improved compositions can be prepared by mixing the individual triterpene components thereof to form a mixture. The triterpene mixtures prepared above that provided efficacy were formulated into improved pharmaceutical compositions.

Improved Composition with Oleanolic Acid and Ursolic Acid

Known amounts of oleanolic acid and ursolic acid were mixed according to a predetermined molar ratio of the components as defined herein. The components were mixed in solid form or were mixed in solvent(s), e.g. methanol, ethanol, chloroform, acetone, propanol, dimethyl sulfoxide (DMSO), dimethylformamide (DMF), dimethylacetamide (DMAC), N-methylpyrrolidone (NMP), water or mixtures thereof. The resultant mixture contained the components in the relative molar ratios as described herein.

For a pharmaceutically acceptable improved composition, at least one pharmaceutically acceptable excipient was mixed in with the pharmacologically active agents. An improved composition is formulated for administration to a mammal.

Improved Composition with Oleanolic Acid and Betulinic Acid

Known amounts of oleanolic acid and betulinic acid were mixed according to a predetermined molar ratio of the components as defined herein. The components were mixed in solid form or were mixed in solvent(s), e.g. methanol, ethanol, chloroform, acetone, propanol, dimethyl sulfoxide (DMSO), dimethylformamide (DMF), dimethylacetamide (DMAC), N-methylpyrrolidone (NMP), water or mixtures thereof. The resultant mixture contained the components in the relative molar ratios as described herein.

For a pharmaceutically acceptable improved composition, at least one pharmaceutically acceptable excipient was mixed in with the pharmacologically active agents. An improved composition is formulated for administration to a mammal.

Improved Composition with Oleanolic Acid, Ursolic Acid and Betulinic Acid

Known amounts of oleanolic acid, ursolic acid and betulinic acid were mixed according to a predetermined molar ratio of the components as defined herein. The components were mixed in solid form or were mixed in solvent(s), e.g. methanol, ethanol, chloroform, acetone, propanol, dimethyl sulfoxide (DMSO), dimethylformamide (DMF), dimethylacetamide (DMAC), N-methylpyrrolidone (NMP), water or mixtures thereof. The resultant mixture contained the components in the relative molar ratios as described herein.

For a pharmaceutically acceptable improved composition, at least one pharmaceutically acceptable excipient was mixed in with the pharmacologically active agents. An improved composition is formulated for administration to a mammal.

Example 3

Evaluation of Compositions in Brain Slice-Based OGD Assay

Coronal brain slices (250 μm thick) were prepared from postnatal day 10 Sprague-Dawley rat pups of either gender (Charles River) and established in organotypic culture. Animals were sacrificed in accordance with NIH guidelines and under Duke IACUC approval and oversight. Briefly, brain tissue slices were cut in ice-cold artificial cerebrospinal fluid (ACSF) and plated in interface configuration on top of culture medium (Neurobasal A medium supplemented with 15% heat-inactivated horse serum, 10 mM KCl, 10 mM HEPES, 100 U/ml penicillin/streptomycin, 1 mM sodium pyruvate, and 1 mM L-glutamine) set in 0.5% reagent-grade agarose. To model ischemic injury, brain slices were subjected to oxygen-glucose deprivation (OGD) by exposure to glucose-free, $N_2$-bubbled ACSF containing low $O_2$ (<0.5%) for 5.5 min.

One hour later, control and OGD-treated brain slices were biolistically transfected with DNAs encoding yellow fluorescent protein (YFP). For assays modeling neurodegeneration in AD or FTD, brain slices were co-transfected with YFP together with an expression construct to WT amyloid precursor protein (APP), or with YFP together with a cDNA constructed in house encoded human Tau4R0N (identical to NCBI Reference Sequence NM_016834), respectively. Brain slice explants were then incubated for 24 h under 5% $CO_2$ at 37° C. for OGD assays; or for 3 d for APP- and tau4R0N-induced neurodegeneration assays. Compositions were added at the indicated concentrations to culture medium at the time of brain slice explantation.

For all brain slice assays, numbers of healthy pyramidal neurons in the cortical regions of each brain slice were imaged on a Leica MZIIIFL fluorescence stereomicroscope. Cortical pyramidal neurons were readily identified by their characteristic positions and orientations in the cortical plate, and by their prominent extension of a single, apical dendrite radially towards the pial surface. Healthy cortical pyramidal neurons were deemed as those 1) presenting a stout and brightly labeled cell body located within the pyramidal neuronal layers of the cortex; 2) retaining a clear apical dendrite extending radially towards the pial surface the slice; 3) expressing≥2 clear basal dendrites≥2 cell body diameters long directly from the neuronal soma; and 4) showing clear and continuous cytoplasmic labeling with the YFP visual marker in the soma and throughout all neuronal processes. Statistically significant differences with respect to the negative control condition (OGD, APP-transfected, or tau4R-transfected treated with DMSO carrier only) were determined using ANOVA followed by Dunnett's post hoc comparison test at the 0.05 confidence level, with N=12 brain slices per condition. Each experiment was carried out at least 2 times.

Example 4

Time-Delay Brain-Slice Assay for Determination of Neuroprotection

This assay was conducted according to Example 3 except that the following changes were made. A specified length of time was allowed between OGD and introduction of a composition being evaluated. The ability of the composition to provide neuroprotection to brain slices if treatment was delayed relative to the timing of the OGD treatment was determined.

Example 5

Evaluation of Compositions for Nrf2 Activation and ARE Gene Expression

Nrf2 Activation

Primary corticostriatal neuronal co-cultures were prepared from E18 Sprague-Dawley rat or C57Bl/6 mouse embryos of either gender. For luciferase reporter assays, the Cignal Antioxidant Response Reporter kit (Qiagen) was used. The 5×ARE luciferase reporter mixture at 40:1 luciferase:Reni//a plasmid was transfected into cortical and striatal neurons separately using an Amaxa electroporation device (Lonza). After electroporation, neurons were pooled and immediately plated into 96-well plates containing mature glial cultures. After culturing for 96 h, compositions were added at the indicated concentrations for 7 or 24 h prior to harvesting using Dual-Glo Luciferase Assay System protocol and reagents (Promega). Dual-wavelength luminescence was detected using a SpectraMax L microplate reader (Molecular Devices). Luciferase values were normalized to the internal *Renilla* control and fold-expression over the DMSO-only treatment control was calculated. At least 3 independent experiments were done using 4-6 biological replicates.

ARE Gene Expression

For qPCR quantification of ARE target gene expression levels, cortical and striatal neurons were plated onto 96-well plates containing mature glial cultures and cultured for 96 h. Composition was added to cultures at the indicated concentrations for 6 h. At the end of the treatment period, cells were lysed and total RNA was isolated using Absolutely RNA mini-prep kits (Agilent Technologies/Stratagene). cDNA was generated using oligo dT primers and Superscript II reverse transcriptase (Invitrogen). Resulting cDNA was used for quantitative PCR of gene transcripts using SYBR Green Real-Time PCR Master Mix (Life Technologies) and the following mouse primers, for: Gclc (forward-5' TGGCCAC-TATCTGCCCAATT-3' and reverse-5'-GTCTGACACG-TAGCCTCGGTAA-3'), Nqo1 (forward-5'-GCCCGCAT-GCAGATCCT-3' and reverse 5'-GGTCTCCTCCCAGACGGTTT3'), Srx (forward-5'-GCTTCCTCTCGGGAGTCCTT-3' and reverse-5'-CAG-CAACAGCGACTACGAAGTAA-3'), and Hmox1 (forward-5'-CCTCACTGGCAGGAAATCATC-3' and reverse-5'-CCTCGTGGAGACGCTTTACATA-3') (Integrated DNA Technologies). For rat corticostriatal co-culture samples, qPCR primers used were as previously described (van Roon-Mom, W. M. et al. Mutant huntingtin activates Nrf2-responsive genes and impairs dopamine synthesis in a PC12 model of Huntington's disease. BMC Molecular Biology (2008), 9, 1-13, doi:10.1186/1471-2199-9-84). Each biological sample was measured in triplicate on a ViiA 7 real-time PCR instrument (Applied Biosystems); fold expression was calculated after normalization to corresponding control GAPDH levels.

Example 6

Evaluation of a Composition in an In Vitro Corticostriatal Co-Culture Assay for Huntington's Disease In this assay, instead of using intact brain slices, mutant htt is introduced via electroporation into high-density, mixed co-cultures of cortical neurons, striatal neurons, and glia arrayed in 96-well plates. The goal of this assay platform is to combine the biological/clinical relevance of a complex primary culture system that recapitulates key aspects of the interconnectivity of disease-relevant neuronal populations in vivo, with the ability to conduct large-scale fully automated screening campaigns. In this assay, over the course of 1-2 weeks in vitro, transfected mutant htt constructs induce the progressive degeneration of both striatal and cortical neurons that are subsequently quantified using automated image acquisition and object detection algorithms on the Cellomics Arrayscan VTI platform. Each data point was drawn from 6 wells with 16 images in each well automatically captured, processed, and analyzed on the Cellomics Arrayscan using protocols developed during a large-scale screening campaign being conducted in association with the Cure Huntington's Disease Initiative. In a full run, some 25,000 images are collected and analyzed in each cycle, 4 cycles per week.

Cortico-Striatal Co-Culture Assay Platform.

Pure glial cultures are prepared in advance of neuronal plating to establish 96-well plates with confluent glial beds. Cortical and striatal tissue are then dissociated separately and "nucleofected" with appropriate DNA constructs and are distinguishable later by the expression of different fluorescent proteins such as YFP, CFP, and mCherry. These separately transfected cortical and striatal neurons are then mixed thoroughly and plated into the 96-well plates containing the previously plated glial monolayers. Compositions are tested in this cortico-striatal co-culture platform.

Example 7

Treatment of Neurological Condition Including but not Limited to Alzheimer's Disease Method A. Neuroprotective Composition Therapy A subject presenting with Alzheimer's disease is prescribed neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with the neuroprotective composition is continued as needed and the dose or dosing regimen can be adjusted as needed until the patient reaches the desired clinical endpoint.

Method B. Combination Therapy: Neuroprotective Composition and Another Therapeutic Agent Method A, above, is followed except that the subject is prescribed and administered neuroprotective composition in combination with one or more other therapeutic agents for the treatment of Alzheimer's disease, or symptoms thereof. Then one or more other therapeutic agents can be administered before, after or with the neuroprotective composition. Dose escalation (or de-escalation) of the one or more other therapeutic agents can also be done. Suitable one or more other therapeutic agents include Namenda™ (memantine HCl), Aricept™ (donepezil), Razadyne™ (galantamine), Exelon™ (rivastigmine), Cognex™ (tacrine), and amantadine.

Example 8

Treatment of Neurological Condition Including but not Limited to Huntington's Disease Method A. Neuroprotective Composition Therapy A subject presenting with Huntington's disease is prescribed the neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with neuroprotective composition is continued as needed and the dose or dosing regimen can be adjusted as needed until the patient reaches the desired clinical endpoint. The doses administered can be similar to those described herein.

Method B. Combination Therapy: Neuroprotective Composition and Another Therapeutic Agent Method A, above, is followed except that the subject is prescribed and administered neuroprotective composition in combination with one or more other therapeutic agents for the treatment of Huntington's disease, or symptoms thereof. The one or more other therapeutic agents can be administered before, after or with the neuroprotective composition. Dose escalation (or de-escalation) of the one or more other therapeutic agents can also be done. Suitable one or more other therapeutic agents include Vitamin E, Baclofen (a derivative of CoQ10), Lamotrigine (an anticonvulsant), remacemide (an anesthetic which is a low affinity NMDA antagonist), and riluzole (Na channel blocker).

Example 9

Treatment of Neurological Condition Including but not Limited to Ischemic Stroke Method A. Neuroprotective Composition Therapy A subject presenting with ischemic stroke is prescribed the neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with the neuroprotective composition is continued as needed and the dose or dosing regimen can be adjusted as needed until the patient reaches the desired clinical endpoint. The doses administered can be similar to those described herein.

Method B. Combination Therapy: Neuroprotective Composition and Another Therapeutic Agent Method A, above, is followed except that the subject is prescribed and administered neuroprotective composition in combination with one or more other therapeutic agents for the treatment of ischemic stroke, or symptoms thereof. The one or more other therapeutic agents can be administered before, after or with the neuroprotective composition. Dose escalation (or de-escalation) of the one or more other therapeutic agents can also be done.

Example 10

Treatment of Neurological Condition Including but not Limited to Parkinson's Disease Method A. Neuroprotective Composition Therapy A subject presenting with Parkinson's disease is prescribed the neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with neuroprotective composition is continued as needed and the dose or dosing regimen can be adjusted as needed until the patient reaches the desired clinical endpoint. The doses administered can be similar to those described herein.

Method B. Combination Therapy: Neuroprotective Composition and Another Therapeutic Agent Method A, above, is followed except that the subject is prescribed and administered neuroprotective composition in combination with one or more other therapeutic agents for the treatment of Parkinson's disease, or symptoms thereof. The one or more other therapeutic agents can be administered before, after or with the neuroprotective composition. Dose escalation (or de-escalation) of the one or more other therapeutic agents can also be done. Suitable one or more other therapeutic agents include a combination of carbidopa and levodopa, rasagiline, pramipexole, ropinrole, amantadine, memantine, entacapone, rotigotine, benztropine, selegiline, biperiden, a combination of carbidopa and levodopa and entacapone, trihexylphenidyl, rivastigmine, apomorphine, levodopa, carbidopa, bromocriptine, *belladonna*, tolcapone, or a combination thereof.

Example 11

Evaluation of Neuroprotective Composition in an In Vitro Assay for Alzheimer's Disease (tau4R and APP)

In the rat brain slice model for APP/Abeta-induced degeneration of cortical pyramidal neurons biolistic transfection is used not only to introduce vital markers such as YFP, but also to introduce disease gene constructs into the same neuronal populations in the brain slices. Thus, the APP/Aβ brain slice model co-transfects YFP with APP isoforms, leading to the progressive degeneration of cortical pyramidal neurons over the course of 3-4 days after brain slice preparation and transfection. The data demonstrate that the neuroprotective composition is to provide concentration-dependent neuroprotection to APP-transfected brain slices.

Example 12

Evaluation of Neuroprotective Composition in an In Vitro Assay for Stroke and Non-Stroke Method A. Stroke: Preparation of Cortical Brain Slices and OGD.

Neocortical brain slices were prepared from PND 7 Sprague-Dawley rat pups. The cerebral cortex was dissected, cut into 400-μ-thick slices and transferred into a container containing cold artificial cerebrospinal fluid with 1

μM MK-801 before plating; MK-801 was not included in any subsequent procedures. To mimic ischemic injury using transient oxygen-glucose deprivation (OGD), slices from one hemisphere of each brain were exposed to glucose-free, $N_2$-bubbled artificial cerebrospinal fluid for 7.5 min in a low $O_2$ (0.5%) environment. The OGD slices were then plated side-by-side with control slices from the contralateral hemisphere on nitrocellulose or Millicell (Millipore) permeable membranes, which were prepared identically except for no OGD. Thirty minutes after plating, the brain slice pairs were transfected, transferred to 24-well plates, and incubated at 37° C. under 5% $CO_2$ in humidified chambers. In each experiment, 5-6 minutes of oxygen-glucose deprivation (OGD) was used to induce >50% loss of healthy cortical neurons by 24 hrs. A set concentration of control material used as the internal positive control. Various concentrations of the compositions are evaluated Method B. Non-Stroke: Brain Slice Assay.

Compositions were tested on "nonstroked" brain slices; that is, ones that were sliced and transfected with YFP but not subjected to additional trauma via OGD. See experimental procedure outlined above.

Example 13

Preparation of Dosage Forms Containing Triterpene-Based Composition

Method A. Cremophor-Based Drug Delivery System

The following ingredients are provided in the amounts indicated.

| Reagent Name | Function | Percent of Formulation (% w/w) |
| --- | --- | --- |
| PBI-01011 | Active agent | 3.7 |
| Vitamin E | Antioxidant | 0.1 |
| Labrasol | Surfactant | 9.2 |
| Ethanol | Co-solvent | 9.6 |
| Cremophor EL | Surfactant | 62.6 |
| Cremophor RH40 | Surfactant | 14.7 |

The excipients are dispensed into a jar and shook in a New Brunswick Scientific C24KC Refrigerated Incubator shaker for 24 hours at 60° C. to ensure homogeneity. The samples are then pulled and visually inspected for solubilization.

Method B. GMO/Cremophor-Based Drug Delivery System

The following ingredients are provided in the amounts indicated.

| Reagent Name | Function | Percent of Formulation (% w/w) |
| --- | --- | --- |
| PBI-01011 | Active agent | 4.7 |
| Vitamin E | Antioxidant | 0.1 |
| Labrasol | Surfactant | 8.5 |
| Ethanol | Co-solvent | 7.6 |
| Cremophor EL | Surfactant | 56.1 |
| Glycerol Monooleate | Surfactant | 23.2 |

The procedure of Method A is followed.

Method C. Labrasol-Based Drug Delivery System

The following ingredients are provided in the amounts indicated.

| Reagent Name | Function | Percent of Formulation (% w/w) |
| --- | --- | --- |
| PBI-01011 | Active agent | 3.7 |
| Vitamin E | Antioxidant | 0.1 |
| Labrasol | Surfactant | 86.6 |
| Ethanol | Co-solvent | 9.6 |

The procedure of Method A is followed.

Method D. Vitamin E-TPGS Based Micelle Forming System

The following ingredients are provided in the amounts indicated.

| Component | Function | Weight % (w/w) |
| --- | --- | --- |
| Vitamin E | Antioxidant | 1.0 |
| Vitamin E TPGS | Surfactant | 95.2 |
| PBI-01011 | Active agent | 3.8 |

The procedure of Method A is followed.

Method E. Multi-Component Drug Delivery System

The following ingredients are provided in the amounts indicated.

| Component | Weight (g) | Weight % (w/w) |
| --- | --- | --- |
| Vitamin E | 10.0 | 1.0 |
| Cremophor ELP | 580.4 | 55.9 |
| Labrasol | 89.0 | 8.6 |
| Glycerol Monooleate | 241.0 | 23.2 |
| Ethanol | 80.0 | 7.7 |
| PBI-01011 | 38.5 | 3.7 |
| Total | 1038.9 | 100 |

The procedure of Method A is followed.

Example 14

Preparation of Enteric Coated Capsules

Step I: Preparation of Liquid-Filled Capsule

Hard gelatin capsules (50 counts, 00 size) are filled with a liquid composition of Example 13. These capsules are filled with 800 mg of the formulation and then sealed by hand with a 50% ethanol/50% water solution. The capsules are then banded by hand with 22% gelatin solution containing the following ingredients in the amounts indicated.

| Ingredient | Wt. (g) |
| --- | --- |
| Gelatin | 140.0 |
| Polysorbate 80 | 6.0 |
| Water | 454.0 |
| Total | 650.0 |

The gelatin solution mixed thoroughly and allowed to swell for 1-2 hours. After the swelling period, the solution is covered tightly and placed in a 55° C. oven and allowed to liquefy. Once the entire gelatin solution is liquid, the banding is performed. Using a pointed round 3/0 artist brush, the gelatin solution is painted onto the capsules. Banding kit provided by Shionogi is used. After the banding, the capsules are kept at ambient conditions for 12 hours to allow the band to cure.

Step II: Coating of Liquid-Filled Capsule

A coating dispersion is prepared from the ingredients listed in the table below.

| Ingredient | Wt. % | Solids % | Solids (g) | g/Batch |
| --- | --- | --- | --- | --- |
| Eudragit L30D55 | 40.4 | 60.5 | 76.5 | 254.9 |
| TEC | 1.8 | 9.0 | 11.4 | 11.4 |
| AlTalc 500V | 6.1 | 30.5 | 38.5 | 38.5 |
| Water | 51.7 | na | na | 326.2 |
| Total | 100.0 | 100.0 | 126.4 | 631.0 |

If banded capsules according to Step I are used, the dispersion is applied to the capsules to a 20.0 mg/cm² coating level. The following conditions are used to coat the capsules.

| Parameters | Set-up |
| --- | --- |
| Coating Equipment | Vector LDCS-3 |
| Batch Size | 500 g |
| Inlet Air Temp. | 40° C. |
| Exhaust Air Temp. | 27-30° C. |
| Inlet Air Volume | 20-25 CFM |
| Pan Speed | 20 rpm |
| Pump Speed | 9 rpm (3.5 to 4.0 g/min) |
| Nozzle Pressure | 15 psi |
| Nozzle diameter | 1.0 mm |
| Distance from tablet bed* | 2-3 in |

*Spray nozzle was set such that both the nozzle and spray path were under the flow path of inlet air.

Example 15

Preparation of a Tablet Comprising Triterpene-Based Composition

An initial tabletting mixture of 3% Syloid 244FP and 97% microcrystalline cellulose (MCC) is mixed. Then, an existing batch of composition prepared according to Example 13 is incorporated into the Syloid/MCC mixture via wet granulation. This mixture is labeled "Initial Tabletting Mixture) in the table below. Additional MCC is added extra-granularly to increase compressibility. This addition to the Initial Tabletting Mixture is labeled as "Extra-granular Addition." The resultant mixture from the extra-granular addition is the same composition as the "Final Tabletting Mixture."

| Component | Weight (g) | Weight % (w/w) |
| --- | --- | --- |
| Initial Tabletting Mixture | | |
| Microcrystalline cellulose | 48.5 | 74.2 |
| Colloidal Silicon Dioxide/Syloid 244FP | 1.5 | 2.3 |
| Formulation from Ex. 13 | 15.351 | 23.5 |
| Total | 65.351 | 100.0 |

Extragranular Addition

| Component | Weight (g) | Weight % (w/w) |
| --- | --- | --- |
| Initial Tabulating Mixture | 2.5 | 50.0 |
| Microcrystalline cellulose | 2.5 | 50.0 |
| Total | 5 | 100.0 |

Final Tabletting Mixture: Abbreviated

| Component | Weight (g) | Weight % (w/w) |
| --- | --- | --- |
| Microcrystalline cellulose | 4.36 | 87.11 |
| Colloidal Silicon Dioxide/Syloid 244FP | 0.06 | 1.15 |
| Formulation from Ex. 13 | 0.59 | 11.75 |
| Total | 5.00 | 100 |

Final Tabletting Mixture: Detailed

| Component | Weight (g) | Weight % (w/w) |
| --- | --- | --- |
| Microcrystalline cellulose | 4.36 | 87.11 |
| Colloidal Silicon Dioxide/Syloid 244FP | 0.06 | 1.15 |
| Vitamin E | 0.01 | 0.11 |
| Cremophor ELP | 0.33 | 6.56 |
| Labrasol | 0.05 | 1.01 |
| Glycerol Monooleate | 0.14 | 2.72 |
| Ethanol | 0.05 | 0.90 |
| PBI-01011 | 0.02 | 0.44 |
| Total | 5.00 | 100.00 |

Syloid 244FP is a colloidal silicon dioxide manufactured by Grace Davison. Colloidal silicon dioxide is commonly used to provide several functions, such as an adsorbant, glidant, and tablet disintegrant. Syloid 244FP was chosen for its ability to adsorb 3 times its weight in oil and for its 5.5 micron particle size.

Example 16

Determining Efficacy of Triterpene-Based Compositions in Treating Autoimmune Condition, Disease or Disorder The method of Martin et al. ("Natural triterpenes modulate immune-inflammatory markers of experimental autoimmune encephalomyelitis: therapeutic implications of multiple sclerosis" in Brit. J. Pharmacol. (2012), 166, 1708-1723, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.33-5:0.33-5.

Example 17

Determining Efficacy of Triterpene-Based Compositions in Treating Tuberculosis

The method of Jimenez-Arellanes et al. ("Ursolic and oleanolic acids as antimicrobial and immunomodulatory compounds for tuberculosis treatment" in BMC Complementary and Altern. Med. (2013), 13, 258-269, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.33-5:0.33-5.

Example 18

Determining Efficacy of Triterpene-Based Compositions in Treating Cell-Proliferation Related Condition, Disease or Disorder Compositions of the invention are evaluated for treating cell proliferation condition, disease or disorder according to any of the methods of Newman et al. (U.S. Pat. Nos. 8,187,644B2, 8,394,434B2, 7,402,325B2, 9,494,589B2, 9,846,156B2, 8,367,363B2, the entire disclosures of which are hereby incorporated by reference) or of Cauni et al. ("Effects of ursolic and oleanolic acid on SK-MEL-2 melanoma cells: in vitro and in vivo assays", in Inter. J. Oncol. (2017), 51, 1651-1660, the entire disclosure of which is hereby incorporated by reference) except that compositions of the invention comprising at least two or at least three triterpenes and excluding cardiac glycoside are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.33-5:0.33-5.

Example 19

Determining Efficacy of Triterpene-Based Compositions in Treating Viral Infection Compositions of the invention are evaluated for treating viral infections listed above according to the methods of Newman et al. (WO 2018/053123A1, the entire disclosure of which is hereby incorporated by reference) except that compositions of the invention comprising at least two or at least three triterpenes and excluding cardiac glycoside are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.33-5:0.33-5.

Example 20

Determining Efficacy of Triterpene-Based Compositions in Treating Bacterial Infection Compositions of the invention are evaluated for treating bacterial infections listed above according to the methods of Kim et al. ("Antimicrobial action of oleanolic acid on *Listeria monocytogenes, Enterococcus faecium*, and *Enterococcus faecalis*" in PLOS ONE, DOI:10.1371/Journal.pone.0118800, (2015), 1-11, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.33-5:0.33-5.

Example 21

Determining Efficacy of Triterpene-Based Compositions in Treating Diabetes

Compositions of the invention are evaluated for treating diabetes and related conditions according to the methods of Lo et al. ("Development of betulinic acid as an agonist of TGR5 receptor using a new in vitro assay" in Drug Des. Dvlp. Ther. (2016), 10, 2669-2676, the entire disclosure of which is hereby incorporated by reference) or the methods of Yin ("Inhibitory effects and actions of pentacyclic triterpenes upon glycation" in Biomedicine (2015), 5(3), 1-8, the entire disclosure of which is hereby incorporated by reference), except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.33-5:0.33-5.

Example 22

Determining Efficacy of Triterpene-Based Compositions in Treating Musculoskeletal Condition, Disease or Disorder Compositions of the invention are evaluated for treating musculoskeletal condition, disease or disorder, in particular age-related loss of muscle mass, according to the methods of Ebert et al. ("Identification and Small Molecule Inhibition of an Activating Transcription Factor 4 (ATF4)-dependent Pathway to Age-related Skeletal Muscle Weakness and Atrophy" in J. Biol. Chem. (2015), 290(42), 25497-25511, the entire disclosure of which is hereby incorporated by reference) or the methods of Kunkel et al. ("mRNA expression signatures of human skeletal muscle atrophy identify a natural compound that increases muscle mass" in Cell Metab. (2011), 13(6), 627-638, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.33-5:0.33-5.

Example 23

Determining Efficacy of Triterpene-Based Compositions in Treating Parasitic Infection Compositions of the invention are evaluated for treating parasitic infection according to the methods of Lopez et al. ("Phytochemical composition, antiparasitic and alpha-glucosidase inhibition activities from *Pelliciera rhizophorae*" in Chem. Cent. J. (2015), 9:53, 1-11, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.15-2.5:0.15-2.5. A composition comprising two triterpenes at the following molar ratio(s) may be found to be active: OA:UA is 9-12:0.33-5 or OA:BA is 9-12:0.33-5.

Example 24

Determining Efficacy of Triterpene-Based Compositions in Treating Protozoal Infection Compositions of the invention are evaluated for treating protozoal according to the methods of Yamamoto et al. ("The effect of ursolic acid on *Leishmania amazonensis* is related to programmed cell death and presents therapeutic potential in experimental cutaneous leishmaniasis" in PLOS ONE DOI:10.1371/journal.pone.0144946, (2015), 1-19, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.15-2.5:0.15-2.5. A composition comprising two triterpenes at the following molar ratio(s) may be found to be active: OA:UA is 9-12:0.33-5 or OA:BA is 9-12:0.33-5.

Example 25

Determining Efficacy of Triterpene-Based Compositions in Treating Oxidative Stress-Related Condition, Disease or Disorder Compositions of the invention are evaluated for treating oxidative stress-related condition, disease or disorder according to the methods of Madlala et al. ("Changes in renal and oxidative status associated with hypotensive effects of oleanolic acid and related synthetic derivatives in experimental animals" in PLOS ONE DOI:10.1371/journal.pone.0128192, (2015), 1-20, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.15-2.5:0.15-2.5. A composition comprising two triterpenes at the following molar ratio(s) may be found to be active: OA:UA is 9-12:0.33-5 or OA:BA is 9-12:0.33-5.

Example 26

Determining Efficacy of Triterpene-Based Compositions in Treating Gastrointestinal Condition, Disease or Disorder Compositions of the invention are evaluated for treating gastrointestinal condition, disease or disorder according to the methods of Dinh et al. ("Bardoxolone methyl prevents high-fat diet-induced colon inflammation in mice" in J. Histochem. Cytochem. (2016), 64(4), 237-255, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.15-2.5:0.15-2.5. A composition comprising two triterpenes at the following molar ratio(s) may be found to be active: OA:UA is 9-12:0.33-5 or OA:BA is 9-12:0.33-5.

Example 27

Determining Efficacy of Triterpene-Based Compositions in Treating Angiogenesis-Related Condition, Disease or Disorder Compositions of the invention are evaluated for treating angiogenesis-related condition, disease or disorder according to the methods of Saraswati et al. ("Ursolic acid inhibits tumor angiogenesis and induces apoptosis through mitochondrial-dependent pathway in Ehrlich ascites carcinoma tumor" in Chem. Biol. Interact. (2013), 206(2), 153-165, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.15-2.5:0.15-2.5. A composition comprising two triterpenes at the following molar ratio(s) may be found to be active: OA:UA is 9-12:0.33-5 or OA:BA is 9-12:0.33-5.

Example 28

Determining Efficacy of Triterpene-Based Compositions in Treating Cardiovascular Condition, Disease or Disorder Compositions of the invention are evaluated for treating cardiovascular condition, disease or disorder, in particular hypertension, according to the methods of Steinkamp-Fenske et al. ("Reciprocal upregulation of endothelial nitric-oxide synthase and NADPH oxidase by betulinic acid in human endothelial cells" in J. Pharmacol. Exper. Therap. (2007), 322(2), 836-842, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.15-2.5:0.15-2.5. A composition comprising two triterpenes at the following molar ratio(s) may be found to be active: OA:UA is 9-12:0.33-5 or OA:BA is 9-12:0.33-5.

Example 29

Determining Efficacy of Triterpene-Based Compositions in Treating Hepatic Condition, Disease or Disorder Compositions of the invention are evaluated for treating hepatic condition, disease or disorder according to the methods of Yi et al. ("Betulinic acid prevents alcohol-induced liver damage by improving the antioxidant system in mice" in J. Vet. Sci. (2014), 15(1), 141-148, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.15-2.5:0.15-2.5. A composition comprising two triterpenes at the following molar ratio(s) may be found to be active: OA:UA is 9-12:0.33-5 or OA:BA is 9-12:0.33-5.

Example 30

Determining Efficacy of Triterpene-Based Compositions in Treating Bone-Related Condition, Disease or Disorder Compositions of the invention are evaluated for treating bone-related condition, disease or disorder according to the methods of Choi et al. ("Betulinic acid synergistically enhances BMP2-induced bone formation via stimulating Smad 1/5/8 and p38 pathways" in J. Biomed. Sci. (2016), 23:45, 1-9, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.15-2.5:0.15-2.5. A composition comprising two triterpenes at the following molar ratio(s) may be found to be active: OA:UA is 9-12:0.33-5 or OA:BA is 9-12:0.33-5.

Example 31

Determining Efficacy of Triterpene-Based Compositions in Treating Dermatological Condition, Disease or Disorder, in Particular Wound Compositions of the invention are evaluated for treating dermatological condition, disease or disorder according to the methods of Ebeling et al. ("From a traditional medicinal plant to a rational drug: understanding the clinically proven wound healing efficacy of birch bark extract" in PLOS ONE (2014), 9(1), e86147, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.15-2.5:0.15-2.5. A composition comprising two triterpenes at the following molar ratio(s) may be found to be active: OA:UA is 9-12:0.33-5 or OA:BA is 9-12:0.33-5.

Example 32

Determining Efficacy of Triterpene-Based Compositions in Treating Renal Condition, Disease or Disorder Compositions of the invention are evaluated for treating renal condition, disease or disorder according to the methods of Madlala et al. ("Changes in renal and oxidative status associated with hypotensive effects of oleanolic acid and related synthetic derivatives in experimental animals" in PLOS ONE DOI:10.1371/journal.pone.0128192, (2015), 1-20, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.15-2.5:0.15-2.5. A composition comprising two triterpenes at the following molar ratio(s) may be found to be active: OA:UA is 9-12:0.33-5 or OA:BA is 9-12:0.33-5.

Example 33

Determining Efficacy of Triterpene-Based Compositions in Treating Metabolic Condition, Disease or Disorder Compositions of the invention are evaluated for treating metabolic condition, disease or disorder according to the methods of Kunkel et al. ("mRNA expression signatures of human skeletal muscle atrophy identify a natural compound that increases muscle mass" in Cell Metab. (2011), 13(6), 627-638, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.15-2.5:0.15-2.5. A composition comprising two triterpenes at the following molar ratio(s) may be found to be active: OA:UA is 9-12:0.33-5 or OA:BA is 9-12:0.33-5.

Example 34

Determining Efficacy of Triterpene-Based Compositions in Treating Pulmonary Condition, Disease or Disorder Compositions of the invention are evaluated for treating pulmonary condition, disease or disorder according to the methods of Feng et al. ("Inhibition of human neutrophil elastase by pentacyclic triterpenes" in PLOS ONE (2013), 8(12), e82794, the entire disclosure of which is hereby incorporated by reference) except that compositions of the invention comprising at least two or at least three triterpenes are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.15-2.5:0.15-2.5. A composition comprising two triterpenes at the following molar ratio(s) may be found to be active: OA:UA is 9-12:0.33-5 or OA:BA is 9-12:0.33-5.

Example 35

Determining Efficacy of Triterpene-Based Compositions in Treating Viral Infection Compositions of the invention are evaluated for treating viral infection, in particular Flaviviriade infection, Togaviridae infection, Paramyxoviridae infection, and Filoviridae infection, according to the methods of Phoenix Biotechnology, Inc. (WO 2018/053123A1, the entire disclosure of which is hereby incorporated by reference) except that compositions of the invention comprising at least two or at least three triterpenes and excluding cardiac glycoside are evaluated.

Triterpene-based compositions containing oleanolic acid as the primary triterpene and ursolic acid and betulinic acid as secondary triterpenes may be found to be active. A composition comprising the three triterpenes at the following molar ratio(s) may be found to be active: OA:UA:BA is 9-12:0.15-2.5:0.15-2.5. A composition comprising two triterpenes at the following molar ratio(s) may be found to be active: OA:UA is 9-12:0.33-5 or OA:BA is 9-12:0.33-5.

Example 36

Preparation of Mixtures of Triterpene Forms

The following compositions are made by mixing the specified forms of a triterpene. No specific order of mixing is required. The forms can be mixed in any form in the presence or absence of liquid.

| Sample | Triterpene Form Present (Y/N) | | | |
| --- | --- | --- | --- | --- |
| | Free acid | Salt | Derivative | Prodrug |
| Combination 1 | Y | Y | N | N |
| Combination 2 | Y | N | Y | N |
| Combination 3 | Y | N | N | Y |
| Combination 4 | N | Y | Y | N |
| Combination 5 | N | Y | N | Y |
| Combination 6 | N | N | Y | Y |
| Combination 7 | N | Y | N | Y |
| Combination 8 | Y | Y | Y | N |
| Combination 9 | Y | N | Y | Y |
| Combination 10 | Y | Y | N | Y |
| Combination 11 | N | Y | Y | Y |
| Combination 12 | Y | Y | Y | Y. |

Each form of triterpene to be included in a combination is provided. The forms are then mixed to provide the respective combination-based triterpene.

For example, triterpene free acid form and triterpene salt form(s) are mixed. Alternatively, triterpene free acid form and triterpene derivative form(s) are mixed. Still, triterpene free acid form and triterpene prodrug form(s) are mixed.

Example 37

Treatment of Zika Virus Infection in a Subject

Method A. Antiviral Composition Therapy

A subject presenting with Zika virus infection is prescribed antiviral composition, and therapeutically relevant doses are administered to the subject according to a prescribed dosing regimen for a period of time. The subject's level of therapeutic response is determined periodically. The level of therapeutic response can be determined by determining the subject's Zika virus titre in blood or plasma. If the level of therapeutic response is too low at one dose, then the dose is escalated according to a predetermined dose escalation schedule until the desired level of therapeutic response in the subject is achieved. Treatment of the subject with antiviral composition is continued as needed and the dose or dosing regimen can be adjusted as needed until the patient reaches the desired clinical endpoint.

Method B. Combination Therapy: Antiviral Composition with Another Agent

Method A, above, is followed except that the subject is prescribed and administered one or more other therapeutic agents for the treatment of Zika virus infection or symptoms thereof. Then one or more other therapeutic agents can be administered before, after or with the antiviral composition. Dose escalation (or de-escalation) of the one or more other therapeutic agents can also be done.

Example 38

In Vitro Evaluation of Antiviral Activity Against Zika Virus Infection

Method A. Pure Compound

Vero E6 cells (aso known as Vero C1008 cells, ATTC No. CRL-1586; https://www.atcc.org/Products/All/CRL-1586.aspx were infected with ZIKV (Zika virus strain PRV-ABC59; ATCC VR-1843; https://www.atcc.org/Products/All/VR-1843.aspx) at an MOI (multiplicity of infection) of 0.2 in the presence of cardiac glycoside. Cells were incubated with virus and compound for 1 hr, after which the inoculum and compound were discarded. Cells were given fresh medium and incubated for 48 hr, after which they were fixed with formalin and stained for ZIKV infection. Other compounds are evaluated under the same conditions and exhibit very varying levels of antiviral activity against Zika virus.

Method B. Compound in Extract Form

An extract containing a target compound being tested is evaluated as detailed in Method A, except that the amount of extract is normalized to the amount of target compound in the extract. For example, an extract containing 2% wt of oleandrin contains 20 microg of oleandrin per 1 mg of extract. Accordingly, if the intended amount of oleandrin for evaluation is 20 microg, then 1 mg of extract would be used in the assay.

Example 39

Treatment of Filovirus Infection in a Subject

Exemplary Filovirus infections include Ebolavirus and Marburgvirus.

Method A. Antiviral Composition Therapy

A subject presenting with Filovirus infection is prescribed antiviral composition, and therapeutically relevant doses are administered to the subject according to a prescribed dosing regimen for a period of time. The subject's level of therapeutic response is determined periodically. The level of therapeutic response can be determined by determining the subject's Filovirus titre in blood or plasma. If the level of therapeutic response is too low at one dose, then the dose is escalated according to a predetermined dose escalation schedule until the desired level of therapeutic response in the subject is achieved. Treatment of the subject with antiviral composition is continued as needed and the dose or dosing regimen can be adjusted as needed until the patient reaches the desired clinical endpoint.

Method B. Combination Therapy: Antiviral Composition with Another Agent

Method A, above, is followed except that the subject is prescribed and administered one or more other therapeutic agents for the treatment of Filovirus infection or symptoms thereof. Then one or more other therapeutic agents can be administered before, after or with the antiviral composition. Dose escalation (or de-escalation) of the one or more other therapeutic agents can also be done.

Example 40

Treatment of Flavivirus Infection in a Subject

Exemplary Flavivirus infections include Yellow Fever, Dengue Fever, Japanese Enchephalitis, West Nile Viruses, Zikavirus, Tick-borne Encephalitis, Kyasanur Forest Disease, Alkhurma Disease, Chikungunya virus, Omsk Hemorrhagic Fever, Powassan virus infection.

Method A. Antiviral Composition Therapy

A subject presenting with Flavivirus infection is prescribed antiviral composition, and therapeutically relevant doses are administered to the subject according to a prescribed dosing regimen for a period of time. The subject's level of therapeutic response is determined periodically. The level of therapeutic response can be determined by determining the subject's Flavivirus titre in blood or plasma. If the level of therapeutic response is too low at one dose, then the dose is escalated according to a predetermined dose escalation schedule until the desired level of therapeutic response in the subject is achieved. Treatment of the subject with antiviral composition is continued as needed and the dose or dosing regimen can be adjusted as needed until the patient reaches the desired clinical endpoint.

Method B. Combination Therapy: Antiviral Composition with Another Agent

Method A, above, is followed except that the subject is prescribed and administered one or more other therapeutic agents for the treatment of Flavivirus infection or symptoms thereof. Then one or more other therapeutic agents can be administered before, after or with the antiviral composition. Dose escalation (or de-escalation) of the one or more other therapeutic agents can also be done.

Example 41

Evaluation of Antiviral Activity Against Zikavirus and Dengue Virus

A CPE-based antiviral assay was performed by infecting target cells in the presence or absence of test compositions, at a range of concentrations. Infection of target cells by results in cytopathic effects and cell death. In this type of assay, reduction of CPE in the presence of test composition, and the corresponding increase in cell viability, is used as an indicator of antiviral activity. For CPE-based assays, cell viability was determined with a neutral red readout. Viable cells incorporate neutral red in their lysosomes. Uptake of neutral red relies on the ability of live cells to maintain a lower pH inside their lysosomes than in the cytoplasm, and this active process requires ATP. Once inside the lysosome, the neutral red dye becomes charged and is retained intracellularly. After a 3-hour incubation with neutral red (0.033%), the extracellular dye was removed, cells were washed with PBS, and the intracellular neutral red was solubilized with a solution of 50% ethanol+1% acetic acid. The amount of neutral red in solution was quantified by reading the absorbance (optical density) of each well at 490 nm Adherent cell lines were used to evaluate the antiviral activity of compositions against a panel of viruses. Compositions were pre-incubated with the target cells for 30 min before the addition of virus to the cells. The compositions were present in the cell culture medium for the duration of the infection incubation period. For each infection assay, a viability assay was set up in parallel using the same concentrations of compositions (duplicates) to determine cytotoxicity effects of the compositions in the absence of virus.

The antiviral activity of test compositions was determined by comparing infection levels (for immunostaining-based assay) or viability (for CPE-based assays) of cells under test conditions to the infection level or viability of uninfected cells. Cytotoxic effects were evaluated in uninfected cells by comparing viability in the presence of inhibitors to the viability of mock-treated cells. Cytotoxicity was determined by an XTT viability assay, which was conducted at the same timepoint as the readout for the corresponding infection assay.

Test compositions were dissolved in 100% methanol. Eight concentrations of the compositions were generated (in duplicate) by performing 8-fold dilutions, starting with 50 µM as the highest concentration tested. The highest test concentration of composition (50 µM) resulted in a 0.25% final concentration of methanol (v/v %) in the culture medium. An 8-fold dilution series of methanol vehicle was included in each assay plate, with concentrations mirroring the final concentration of methanol in each composition test condition. When possible, the EC50 and CC50 of the composition was determined for each assay using GraphPad Prism software.

Antiviral activity was evaluated by the degree of protection against virus-induced cytopathic effects (CPE). Cells were challenged with virus in the presence of different concentrations of control or compositions. The extent of protection against CPE was monitored after 6 days (ZIKV, Zikavirus) or 7 days (DENY, Dengue virus) post infection by quantifying cell viability in different test conditions and comparing values with that of untreated cells and cells treated with vehicle alone (infection medium).

Quality controls for the neutralization assay were performed on every plate to determine: i) signal to background (S/B) values; ii) inhibition by the known inhibitors, and iii) variation of the assay, as measured by the coefficient of variation (C.V.) of all data points. Overall variation in the infection assays ranged from 3.4% to 9.5%, and overall variation in the viability assays ranged from 1.4% to 3.2%, calculated as the average of all C.V. values. The signal-to-background (S/B) for the infection assays ranged from 2.9 to 11.0, while the signal-to-background (S/B) for the viability assays ranged from 6.5 to 29.9.

Protection of DENV2-induced cytopathic effect (CPE) with Neutral Red readout: For the DENV2 antiviral assay, the 08-10381 Montserrat strain was used. Viral stocks were generated in C6/36 insect cells. Vero cells (epithelial kidney cells derived from *Cercopithecus aethiops*) were maintained in MEM with 5% FBS (MEMS). For both the infection and the viability assays, cells were seeded at 10,000 cells per well in 96-well clear flat bottom plates and maintained in MEMS at 37° C. for 24 hours. The day of infection, samples were diluted 8-fold in U-bottom plates using MEM with 1% bovine serum albumin (BSA). Test material dilutions were prepared at 1.25× the final concentration and 40 µl were incubated with the target cells at 37° C. for 30 minutes. Following the test material pre-incubation, 10 µl of virus dilutions prepared in MEM with 1% BSA was added to each well (50 µl final volume per well) and plates were incubated at 37° C. in a humidified incubator with 5% CO2 for 3 hours. The volume of virus used in the assay was previously determined to produce a signal in the linear range inhibited by Ribavirin and compound A3, known inhibitors of DENV2. After the infection incubation, cells were washed with PBS, then MEM containing 2% FBS (MEM2) to remove unbound virus. Subsequently, 50 µl of medium containing inhibitor dilutions prepared at a 1× concentration in MEM2 was added to each well. The plate was incubated at 37° C. in the incubator (5% CO2) for 7 days. Controls with no virus ("mock-infected"), infected cells incubated with medium alone, infected cells incubated with vehicle alone (methanol), and wells without cells (to determine background) were included in the assay plate. Control wells containing 50 µM Ribavirin and 0.50 µM compound A3 were also included on the assay plate. After 7 days of infection, cells were stained with neutral red to monitor cell viability. Test materials were evaluated in duplicates using serial 8-fold dilutions in infection medium. Controls included cells incubated with no virus ("mock-infected"), infected cells incubated with medium alone, or infected cells in the presence of Ribavirin (0.5 µM) or A3 (0.5 µM). A full duplicate inhibition curve with methanol vehicle only was included on the same assay plate.

Protection of ZIKV-induced cytopathic effect (CPE) with Neutral Red readout: For the ZIKV antiviral assay, the PLCal ZV strain was used. Vero cells (epithelial kidney cells derived from *Cercopithecus aethiops*) were maintained in MEM with 5% FBS (MEMS). For both the infection and the viability assays, cells were seeded at 10,000 cells per well in 96-well clear flat bottom plates and maintained in MEMS at 37° C. for 24 hours. The day of infection, samples were diluted 8-fold in U-bottom plates using MEM with 1% bovine serum albumin (BSA). Test material dilutions were prepared at 1.25× the final concentration and 40 µl were incubated with the target cells at 37° C. for 30 minutes. Following the test material pre-incubation, 10 µl of virus dilutions prepared in MEM with 1% BSA was added to each well (50 µl final volume per well) and plates were incubated at 37° C. in a humidified incubator with 5% CO2 for 3 hours. After the infection incubation, cells were washed with PBS, then MEM containing 2% FBS (MEM2) to remove unbound virus. Subsequently, 50 µl of medium containing inhibitor dilutions prepared at a 1× concentration in MEM2 was added to each well. The plate was incubated at 37° C. in the incubator (5% CO2) for 6 days. Controls with no virus ("mock-infected"), infected cells incubated with medium alone, infected cells incubated with vehicle alone (methanol), and wells without cells (to determine background) were included in the assay plate. After 6 days of infection, cells were stained with neutral red to monitor cell viability. Test materials were evaluated in duplicates using serial 8-fold dilutions in infection medium. Controls included cells incubated with no virus ("mock-infected"), infected cells incubated with medium alone, or infected cells in the presence of A3 (0.5 µM). A full duplicate inhibition curve with methanol vehicle only was included on the same assay plate.

Analysis of CPE-based viability data: for the neutral red assays, cell viability was determined by monitoring the absorbance at 490 nm. The average signal obtained in wells with no cells was subtracted from all samples. Then, all data points were calculated as a percentage of the average signal observed in the 8 wells of mock (uninfected) cells on the same assay plate. Infected cells treated with medium alone reduced the signal to an average of 4.2% (for HRV), 26.9% (for DENY), and 5.1% (for ZIKV) of that observed in uninfected cells. The signal-to-background (S/B) for this assay was 2.9 (for DENV), and 7.2 (for ZIKV), determined as the viability percentage in "mock-infected" cells compared to that of infected cells treated with vehicle only.

Viability assay (XTT) to assess compound-induced cytotoxicity: Mock-infected cells were incubated with inhibitor dilutions (or medium only) using the same experimental setup and inhibitor concentrations as was used in the corresponding infection assay. The incubation temperature and duration of the incubation period mirrored the conditions of the corresponding infection assay. Cell viability was evaluated with an XTT method. The XTT assay measures mitochondrial activity and is based on the cleavage of yellow tetrazolium salt (XTT), which forms an orange formazan dye. The reaction only occurs in viable cells with active mitochondria. The formazan dye is directly quantified using a scanning multi-well spectrophotometer. Background levels obtained from wells with no cells were subtracted from all data-points. Controls with methanol vehicle alone (at 7 concentrations mirroring the final percent methanol of each Oleandrin test wells) were included in the viability assay plate. The extent of viability was monitored by measuring absorbance at 490 nm.

Analysis of cytotoxicity data: For the XTT assays, cell viability was determined by monitoring the absorbance at 490 nm. The average signal obtained in wells with no cells was subtracted from all samples. Then, all data points were calculated as a percentage of the average signal observed in the 8 wells of mock (uninfected) cells on the same assay plate. The signal-to-background (S/B) for this assay was 29.9 (for IVA), 8.7 (for HRV), 6.5 (for DENV), and 6.7 (for ZIKV), determined as the viability percentage in "mock-infected" cells compared to the signal observed for wells without cells.

Example 42

Evaluation of Antiviral Activity Against Filovirus (Ebolavirus and Marburgvirus)

Method A.
Vero E6 cells were infected with EBOV/Kik (A, MOI=1) or MARV/Ci67 (B, MOI=1) in the presence of oleandrin, digoxin or PBI-05204, an oleandrin-containing plant extract. After 1 hr, inoculum and compounds were removed and fresh medium added to cells. 48 hr later, cells were fixed and immunostained to detect cells infected with EBOV or MARV. Infected cells were enumerated using an Operetta. C) Vero E6 were treated with compound as above. ATP levels were measured by CellTiter-Glo as a measurement of cell viability.
Method B.
Vero E6 cells were infected with EBOV (A,B) or MARV (C,D). At 2 hr post-infection (A,C) or 24 hr post-infection (B,D), oleandrin or PBI-05204 was added to cells for 1 hr, then discarded and cells were returned to culture medium. At 48 hr post-infection, infected cells were analyzed.
Method C.
Vero E6 cells were infected with EBOV or MARV in the presence of oleandrin or PBI-05204 and incubated for 48 hr. Supernatants from infected cell cultures were passaged onto fresh Vero E6 cells, incubated for 1 hr, then discarded (as depicted in A). Cells containing passaged supernatant were incubated for 48 hr. Cells infected with EBOV (B) or MARV (C) were detected as described previously. Control infection rates were 66% for EBOV and 67% for MARV.

Example 43

Evaluation of Antiviral Activity Against Togaviridae Virus (Alphavirus: VEEV and WEEV)

Vero E6 cells were infected with Venezuelan equine encephalitis virus (A, MOI=0.01) or Western equine encephalitis virus (B, MOI=0.1) for 18 hr in the presence or absence of indicated compounds. Infected cells were detected as described herein and enumerated on an Operetta.

Example 44

Treatment of Paramyxoviridae Infection in a Subject

Exemplary Paramyxoviridae family viral infections include Henipavirus genus infection, Nipah virus infection, or Hendra virus infection.
Method A. Antiviral Composition Therapy
A subject presenting with Paramyxoviridae family infection is prescribed antiviral composition, and therapeutically relevant doses are administered to the subject according to a prescribed dosing regimen for a period of time. The subject's level of therapeutic response is determined periodically. The level of therapeutic response can be determined by determining the subject's virus titre in blood or plasma. If the level of therapeutic response is too low at one dose, then the dose is escalated according to a predetermined dose escalation schedule until the desired level of therapeutic response in the subject is achieved. Treatment of the subject with antiviral composition is continued as needed and the dose or dosing regimen can be adjusted as needed until the patient reaches the desired clinical endpoint.
Method B. Combination Therapy: Antiviral Composition with Another Agent
Method A, above, is followed except that the subject is prescribed and administered one or more other therapeutic agents for the treatment of Paramyxoviridae family infection or symptoms thereof. Then one or more other therapeutic agents can be administered before, after or with the antiviral composition. Dose escalation (or de-escalation) of the one or more other therapeutic agents can also be done.

As used herein and unless otherwise specified, the term "about" or "approximately" are taken to mean±10%, ±5%, ±2.5% or ±1% of a specified valued. As used herein and unless otherwise specified, the term "substantially" is taken to mean "to a large degree", "at least a majority of", greater than 70%, greater than 85%, greater than 90%, greater than 95%, greater than 98% or greater than 99%.

When a range is specified herein, the range includes all whole and fractional numbers of said range.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:
1. A triterpene-based composition comprising a combination of a first triterpene oleanolic acid (OA), a second triterpene ursolic acid (UA), and a third triterpene betulinic acid (BA), wherein each triterpene is independently selected at each occurrence from the free acid form thereof, salt(s) form thereof, derivative(s) thereof, prodrug(s) thereof and/or combination thereof, and wherein the molar ratio of OA:UA:BA is selected from the group consisting of about 10:about 1:about 1, about 9-11:about 0.5-1.5:about 0.5-1.5, about 9.5-10.5:about 0.75-1.25:about 0.75-1.25, about 9.5-10.5:about 0.8-1.2:about 0.8-1.2, about 9.75-10.5:about 0.9-1.1:about 0.9-1.1, about 9-12:about 0.15-2.5:about 0.15-2.5, about 9-12:about 0.2-2.5:about 0.2-2.5, about 9-12:about 0.25-2.5:about 0.25-2.5, about 9-12:about 0.35-2.5:about 0.35-2.5, about 9-12:about 0.45-2.5:about 0.45-2.5, about 9-12:about 0.5-2.5:about 0.5-2.5, about 9-12:about 0.16-2: about 0.16-2, about 9-12:about 0.2-2:about 0.2-2, about 9-12:about 0.25-2:about 0.25-2, about 9-12:about 0.25-2: about 0.25-2, about 9-12:about 0.45-2:about 0.45-2, about 9-12:about 0.5-2:about 0.5-2, about 9-12:about 0.16-1.5: about 0.16-1.5, about 9-12:about 0.2-1.5:about 0.2-1.5, about 9-12:about 0.25-1.5:about 0.25-1.5, about 9-12:about 0.7-1.5:about 0.35-1.5, about 9-12:about 0.45-1.5:about 0.45-1.5, about 9-12:about 0.5-1.5:about 0.5-1.5, about 9-12:about 0.16-1:about 0.16-1, about 9-12:about 0.2-1: about 0.2-1, about 9-12:about 0.25-1:about 0.25-1, about 9-12:about 0.35-1:about 0.35-1, about 9-12:about 0.45-1: about 0.45-1, about 9-12:about 0.5-1:about 0.5-1, about 10:about 0.5-2.5:about 0.5-2.5, about 10:about 0.1-1.5:about 0.1-1.5, about 9-12:about 0.25-0.75:about 0.25-0.75, about

9.5-10.5:about 0.35-0.7:about 0.35-0.7, about 9.5-10.5: about 0.4-0.6:about 0.4-0.6, and about 9.75-10.5:about 0.45-0.6:about 0.45-0.6.

2. The composition of claim 1, wherein said composition: a) provides a balanced expression of ARE genes to provide clinical benefit over a wide dosing range without resulting in excessive cellular toxicity; b) provides a substantially expanded therapeutic window as compared to the individual triterpenes thereof administered on a total-triterpene equimolar basis and/or as compared to closely related combinations of the triterpenes; c) provides a substantially improved efficacy as compared to the individual triterpenes thereof administered on a total-triterpene equimolar basis and/or as compared to closely related combinations of the triterpenes; or d) provides substantially reduced incidence or severity of adverse events as compared to the individual triterpenes thereof administered on a total-triterpene equimolar basis and/or as compared to closely related combinations of the triterpenes.

3. The composition of claim 1, wherein at least one of said triterpenes is present as a mixture of two or more different forms thereof.

4. The composition of claim 3, wherein at least one of said triterpenes is present as a mixture of two or more forms defined as follows:

| Sample | Triterpene Form Present (Y/N) | | | |
|---|---|---|---|---|
| | Free acid | Salt | Derivative | Prodrug |
| Combination 1 | Y | Y | N | N |
| Combination 2 | Y | N | Y | N |
| Combination 3 | Y | N | N | Y |
| Combination 4 | N | Y | Y | N |
| Combination 5 | N | Y | N | Y |
| Combination 6 | N | N | Y | Y |
| Combination 7 | N | Y | N | Y |
| Combination 8 | Y | Y | Y | N |
| Combination 9 | Y | N | Y | Y |
| Combination 10 | Y | Y | N | Y |
| Combination 11 | N | Y | Y | Y |
| Combination 12 | Y | Y | Y | Y. |

5. The composition of claim 1, wherein: a) oleanolic acid is present in molar excess over the combined total moles of ursolic acid and betulinic acid, and ursolic acid and betulinic acid are present at about the same molar content; b) oleanolic acid is present in molar excess over the combined total moles of ursolic acid and betulinic acid, and ursolic acid can be present in molar excess over betulinic acid; c) oleanolic acid is present in molar excess over the combined total moles of ursolic acid and betulinic acid, and betulinic acid can be present in molar excess over ursolic acid; d) oleanolic acid is present in molar excess over ursolic acid, and ursolic acid can be present in molar excess over betulinic acid; or e) oleanolic acid is present in molar excess over betulinic acid, and betulinic acid can be present in molar excess over ursolic acid.

6. The composition of claim 1 wherein the molar ratio of OA:UA:BA is about 9-12:about 0.2-2.5:about 0.2-2.5.

7. The composition of claim 1 comprising, as the primary pharmacologically active components
oleanolic acid and/or salt thereof;
ursolic acid and/or salt thereof; and
betulinic acid and/or salt thereof.

8. The composition of claim 1, wherein said composition excludes a cardiac glycoside, steroid, and pharmacologically active polysaccharide.

9. The composition of claim 1 further comprising one or more other therapeutically effective agents.

10. The composition of claim 9, wherein the one or more other therapeutically effective agents is selected from the group consisting of BACE inhibitor, beta-secretase 1, beta-site amyloid precursor protein cleaving enzyme 1, beta-site APP cleaving enzyme 1, membrane-associated aspartic protease 2, memapsin-2, aspartyl protease 2, ASP2, AZD3293, acetylcholinesterase inhibitors, memantine HCl, donepezil, galantamine, rivastigmine, tacrine, anticonvulsants, NMDA (n-methyl d-aspartate) receptor antagonists, sodium channel blockers, Vitamin E, Baclofen, derivative of CoQ10, Lamotrigine, anticonvulsant, remacemide, anesthetic, riluzole, Na channel blocker, Alteplase, thrombolytic agent, levodopa, carbidopa, amantadine, COMT (catechol O-methyl transferase) inhibitor, tolcapone, entacapone, opicapone, dopamine agonist, bromocriptine, pergolide, pramipexole, ropinirole, piribedil, cabergoline, apomorphine, lisuride, selective MAO-B (monoamine oxidase-B) inhibitor, non-selective MAO-B inhibitor, anticholinergic, cholinesterase inhibitor, isocarboxazid, nialamide, phenelzine, hydracarbazine, rasagiline, selegiline, linezolid, and a combination thereof.

11. A pharmaceutical composition comprising one or more pharmaceutical excipients and the triterpene-based composition of claim 1.

12. A pharmaceutical dosage form comprising at least one pharmaceutical excipient and the composition of claim 1.

13. The composition of claim 1, wherein oleanolic acid is present in at least four-fold molar excess over each ursolic acid and betulinic acid individually.

14. The composition of claim 1, wherein the molar content of ursolic acid approximates that of betulinic acid.

15. A triterpene-based composition comprising as the primary pharmacologically active components
oleanolic acid and/or salt thereof (OA);
ursolic acid and/or salt thereof (UA); and
betulinic acid and/or salt thereof (BA),
wherein the molar ratio of OA:UA:BA is about 9-12: about 0.2-2.5:about 0.2-2.5.

* * * * *